(12) United States Patent
Hogg et al.

(10) Patent No.: US 7,674,775 B2
(45) Date of Patent: Mar. 9, 2010

(54) SUBSTANTIALLY CELL MEMBRANE IMPERMEABLE COMPOUND AND USE THEREOF

(75) Inventors: Philip John Hogg, Randwick (AU); Neil Donoghue, Kensington (AU)

(73) Assignee: New South Innovations Pty Limited, UNSW Sydney (AU)

( * ) Notice: Subject to any disclaimer, the term of this patent is extended or adjusted under 35 U.S.C. 154(b) by 389 days.

(21) Appl. No.: 11/419,651

(22) Filed: May 22, 2006

(65) Prior Publication Data

US 2007/0037996 A1  Feb. 15, 2007

Related U.S. Application Data

(63) Continuation of application No. 10/088,540, filed as application No. PCT/AU00/01143 on Sep. 20, 2000, now Pat. No. 7,074,766.

(30) Foreign Application Priority Data

Sep. 20, 1999  (AU)  .................................... PQ2967

(51) Int. Cl.
| | |
|---|---|
| A61K 38/00 | (2006.01) |
| A61K 38/02 | (2006.01) |
| A61K 38/06 | (2006.01) |
| C07K 2/00 | (2006.01) |
| C07K 5/02 | (2006.01) |
| C07K 5/08 | (2006.01) |
| C07K 1/107 | (2006.01) |
| A61K 31/555 | (2006.01) |

(52) U.S. Cl. ............... 514/18; 514/22; 514/6; 514/8; 514/19; 514/184; 530/300; 530/331; 530/332; 530/345; 544/180; 544/181; 544/187

(58) Field of Classification Search ........................ None
See application file for complete search history.

(56) References Cited

U.S. PATENT DOCUMENTS

| | | | |
|---|---|---|---|
| 2,370,092 A | 2/1945 | Tillitson | |
| 2,409,291 A * | 10/1946 | Lott et al. .................... | 556/67 |
| 2,465,308 A * | 3/1949 | Fox et al. .................... | 556/69 |
| 2,553,515 A | 5/1951 | Herman et al. | |
| 2,664,432 A | 12/1953 | Friedheim | |
| 2,951,766 A | 7/1960 | White | |
| 3,883,650 A | 5/1975 | Friedheim, et al. | |
| 5,270,196 A | 12/1993 | Sawada et al. | |
| 5,281,588 A | 1/1994 | Maes et al. | |
| 5,459,263 A | 10/1995 | Floc'H et al. | |
| 7,074,766 B1 | 7/2006 | Hogg et al. | |
| 7,186,695 B2 * | 3/2007 | Hogg ........................... | 514/18 |
| 2001/0044144 A1 | 11/2001 | Anderson et al. | |
| 2005/0101524 A1 | 5/2005 | Hogg | |
| 2007/0037995 A1 | 2/2007 | Hogg et al. | |

FOREIGN PATENT DOCUMENTS

| | | |
|---|---|---|
| FR | 2781674 A1 | 7/1998 |
| WO | 98/51297 A1 | 11/1998 |
| WO | 99/18798 A1 | 4/1999 |
| WO | 99/55344 A1 | 11/1999 |
| WO | 00/56742 A1 | 9/2000 |
| WO | 00/79274 A | 12/2000 |

OTHER PUBLICATIONS

C Gorman, et al. The Hype and the Hope. Time (1998) 151(19). pp. 40-44. Included HTML copy referenced pp. 1-9.*
T Gura. Systems for Identifying New Drugs are Often Faulty. Science (1997) 278 (Nov. 7). pp. 1041-1042.*
GB Dermer. Another Anniversary for the War on Cancer. Bio/Technology (Mar. 12, 1994) p. 320*
R McKie. Cancer Research Set Back a Decade. The Observer (Jun. 10, 2001). pp. 1-4 (HTML text).*
Definition of Cancer. Internet document <<http://www.medterms.com>> 1 page, accessed Sep. 16, 2005, last reviewed Sep. 18, 2004.*
Beilstein Registry No. 21688, 1988-2003 Beilstein Institut zur Foerderung der Chemischen Wissenschaften.
Beilstein Registry No. 22377, 1988-2003 Beilstein Institut zur Foerderung der Chemischen Wissenschaften.
Beilstein Registry No. 51552, 1988-2003 Beilstein Institut zur Foerderung der Chemischen Wissenschaften.
Beilstein Registry No. 111664, 1988-2003 Beilstein Institut zur Foerderung der Chemischen Wissenschaften.
Beilstein Registry No. 116874, 1988-2003 Beilstein Institut zur Foerderung der Chemischen Wissenschaften.
Beilstein Registry No. 273946, 1988-2003 Beilstein Institut zur Foerderung der Chemischen Wissenschaften.
Beilstein Registry No. 358898, 1988-2003 Beilstein Institut zur Foerderung der Chemischen Wissenschaften.
Beilstein Registry No. 3126376, 1988-2003 Beilstein Institut zur Foerderung der Chemischen Wissenschaften.
Beilstein Registry No. 3129248, 1988-2003 Beilstein Institut zur Foerderung der Chemischen Wissenschaften.
Beilstein Registry No. 3135458, 1988-2003 Beilstein Institut zur Foerderung der Chemischen Wissenschaften.
Beilstein Registry No. 3139905, 1988-2003 Beilstein Institut zur Foerderung der Chemischen Wissenschaften.
Beilstein Registry No. 3141604, 1988-2003 Beilstein Institut zur Foerderung der Chemischen Wissenschaften.

(Continued)

*Primary Examiner*—Andrew D Kosar
(74) *Attorney, Agent, or Firm*—McDonnell Boehnen Hulbert & Berghoff LLP

(57) ABSTRACT

The present invention relates to a compound according to Formula (I): $A-(L-Y)_p$, wherein A comprises at least one substantially cell-membrane impermeable pendant group; L comprises any suitable linker and/or spacer group; Y comprises at least one arsenoxide or arsenoxide equivalent; p is an integer from 1 to 10; and the sum total of carbon atoms in A and L together, is greater than 6.

22 Claims, 35 Drawing Sheets

OTHER PUBLICATIONS

Beilstein Registry No. 3152231, 1988-2003 Beilstein Institut zur Foerderung der Chemischen Wissenschaften.
Beilstein Registry No. 3233826, 1988-2003 Beilstein Institut zur Foerderung der Chemischen Wissenschaften.
Beilstein Registry No. 3235693, 1988-2003 Beilstein Institut zur Foerderung der Chemischen Wissenschaften.
Beilstein Registry No. 3254079, 1988-2003 Beilstein Institut zur Foerderung der Chemischen Wissenschaften.
Beilstein Registry No. 3273842, 1988-2003 Beilstein Institut zur Foerderung der Chemischen Wissenschaften.
Beilstein Registry No. 3275319, 1988-2003 Beilstein Institut zur Foerderung der Chemischen Wissenschaften.
Beilstein Registry No. 3285106, 1988-2003 Beilstein Institut zur Foerderung der Chemischen Wissenschaften.
Beilstein Registry No. 3293148, 1988-2003 Beilstein Institut zur Foerderung der Chemischen Wissenschaften.
Beilstein Registry No. 3296676, 1988-2003 Beilstein Institut zur Foerderung der Chemischen Wissenschaften.
Beilstein Registry No. 3298747, 1988-2003 Beilstein Institut zur Foerderung der Chemischen Wissenschaften.
Beilstein Registry No. 3319010, 1988-2003 Beilstein Institut zur Foerderung der Chemischen Wissenschaften.
Beilstein Registry No. 3341328, 1988-2003 Beilstein Institut zur Foerderung der Chemischen Wissenschaften.
Beilstein Registry No. 3344707, 1988-2003 Beilstein Institut zur Foerderung der Chemischen Wissenschaften.
Beilstein Registry No. 3531489, 1988-2003 Beilstein Institut zur Foerderung der Chemischen Wissenschaften.
Fairlamb, et al. "Trypanothione is the Primary Target for Arsenical Drugs against African Trypanosomes" Proc. Natl. Acad. Sci., vol. 26, pp. 2607-2611 (1989).
Fairlamb, A., "Metabolism and Functions of Trypamothione in the Kenetoplastida", Ann. Rev. Microbiol., vol. 46, pp. 695-729 (1992).
Cunningham, et al. "Mechanism of Inhibition of Trypanothione Reductase and Glutathione Reductase by Trivalent Organic Arsenicals" Eur. J. Biochem., vol. 221, pp. 285-295 (1994).
Bhargava, et al. "Effect of arsenical drugs on Glutathione Metabolism of Litomosoides carinii" Mol. Biochem. Parasitol, vol. 9, 99 29-35 (1983).
Carter, et al. "Arsenical-resistant Trypanosomes Lack an Unusual Adenosine Transporter" Nature, vol. 36, No. 6408, pp. 173-176 (1993).
Pisciotto, P., et al. "Induction of Mucosal Glutathione Synthesis by Arsenic" Biochimica et Biophysica Acta, vol. 628, pp. 241-243 (1980).
Chemical Abstracts Registry No. 1112-90-3. p-amino phenyl arsenoxide 2000.
Chemical Abstracts Registry No. 637-03-6. Arsenosobenzene. 2000.
Happersberger, (1998) Eur. Mass Spectrom—4:209-214.
Rudinger, In: Peptide Hormones, JA Parsons, Ed. (1976), 1-7.
Voet et al., Biochemistry, 2nd Edition, (1995), 235-241.
Smilek et al., Proc. Natl. Acad. Sci. USA, (1991), 88, 9633-9637.
Banks et al., J. Med. Chem., (1979), 22(5), 572-575.
Evtodienko, Y. et al., "Mechanisms of the Resistance to the Mitochondrial Permeability Transition in Tumor Cells", Pathophysiology, 1999, 171-178.
Ramachandran, A. et al., "Apoptosis in the Intestinal Epitheliam: Its Relevance in Normal and Pathophysiological Conditions," Journal of Gastroenterology and Hepatology, vol. 15 (2000) pp. 109-120.
Riddles, P. et al., "Reassessment of Ellman's Reagent," Methods in Enzymology, vol. 91 (1983) pp. 50-61.
Rimon, G. et al., "Rapid Communication: Increased Surface Phosphatidylserine Is an Early Marker of Neuronal Apoptosis," Journal of Neuroscience Research, vol. 48 (1997) pp. 563-570.
Rupnow, B. et al., "The Role of Radiation-Induced Apoptosis as a determinant of tumor Responses to radiation Therapy," Apoptosis, vol. 4, No. 2 (1999) pp. 115-143.
Stefanec, "Endothelial Apoptosis, Could it Have a Role in the pathogenesis and Treatment of a Disease?," Chest, vol. 117, No. 3 (2000) pp. 841-854.
Stone, M. et al., "Recombinant Soluble Human Tissue Factor Secreted by Saccharomyces Cerevisiae and Refolded from *Escherichia coli* Inclusion Bodies: Glycosylation of Mutants, Activity and Physical Characterization," Biochem J., vol. 310 (1995) pp. 605-614.
Thompson, "Apoptosis in the pathogenesis and Treatment of Disease," Science, vol. 267 (1995) pp. 1456-1462.
Vermes, I. et al., "A Novel Assay for Apoptosis Flow Cytomertic Detection of Physphatidylserine Expression on Early Apoptoic Cells Using Fluorescein labeled Annexin V," Journal of Immunological Methods, vol. 184 (1995) pp. 39-51.
Virginio, C. et al., "Kinetics of Cell Lysis, Dye Uptake and Permeability Changes in Cells Expressing the Rat P2X7 Receptor," Journal of Physiology, vol. 519 (1999) pp. 335-346.
Weissleder, R. et al., "In Vivo Imaging of Tumors with Protease-Activated Near-Infrared Fluorescent Probes," Nature Biotechnology, vol. 17 (1999) pp. 375-378.
Adams, E. et al., "Chemistry of Organometalloid Complexes with potential Antidotes: Structure of an Organoarsenic (III) Dithiolate Ring," Inorg. Chem., vol. 29 (1990) pp. 1500-1503.
Greenberg, H. et al., "Prostate Cancer in a Transgenic Mouse," PNAS, vol. 92 (1995) pp. 3439-3443.
Hofstra, L. et al., "In Vivo Detection of Apoptosis in an Intracardiac Tumor," JAMA, vol. 285, No. 14 (2001) pp. 1841-1842.
Kaufmann, "Cell Death Induced by Topoisomerase-Targeted Drugs: More Questions Than Answers," Biochimica et Biophysica Acta, vol. 1400 (1998) pp. 195-211.
Mattson, "Apoptosis in Neurodegenerative Disorders," National Review/Molecular Cell Biology, vol. 1 (2000) pp. 120-129.
Novia, "Protein Disulfide Isomerase: The Multifunctional Redox Chaperone of the Endoplasmic Reticulum," Cell & Developmental Biology, vol. 10 (1999) pp. 481-493.
Pronk, G. et al., "Requirement of an Ice-Like Protease for Induction of Apoptosis and Ceramide Generation by Reaper," Science, vol. 271 (1996) pp. 80-810.
Thornberry, N. et al., Caspases: Enemies Within, Science, vol. 281 (1998) pp. 1312-1316.
Zhu, H. et al., "An Ice-Like Protease is a Common Mediator of Apoptosis Induced by Diverse Stimuli in Human Monocytic THP.1 Cells," FEBS Letters, vol. 374 (1995) pp. 303-308.
Gitler, C. et al., "General Method to Identify and Enrich Vicinal Thiol Proteins Present in Intact Cells in the Oxidized, Disulfide State," Analytical Biochemistry, vol. 252 (1997) pp. 48-55.
Korge et al., "Phenylarsine oxide induces mitochondrial permeability transition, hypercontracture, and cardiac cell death", Am. J. Physiol. Hearth Circ. Physiol., 2001, vol. 280, H2203-H2213.
Costantini et al., "Modulation of the mitochondrial permeability transition pore by pyridine nucleotides and dithiol oxidation at two separate sites", The Journal of Biological Chemistry, 1996, 271(12), 6746-6751.
McStay, et al., "Role of critical thiol groups on the matrix surface of the adenine nucleotide translocase in the mechanism of the mitochondrial permeability transition pore", Biochem. J., 2002, 367, 541-548.
Hortelano et al "Nitric oxide induces apoptosis via triggering mitochondrial permeability transition", FEBS Letters, 1997, vol. 410, 373-377.
Balakirev et al., "Gradual changes in permeability of inner mitochondrial membrane precede the mitochondrial permeability transition", Archives of Biochemistry and Biophysics, 1998, 356(1), 46-54.
Constantini et al., "Oxidation of a critical thiol residue of the adenine nucleotide translocator enforces Bcl-2-independent permeability transition core opening and apoptosis", Oncogene, 2000, vol. 19, 307-314.
Don et al., "A peptide trivalent arsenical inhibits tumor angiogenesis by perturbing mitochondrial function in angiogenic endothelial cells", Cancer Cell, 2003, vol. 3, 497-509.
Al-Nasser, "In vivo prevention of adriamycin cardiotoxicity by cyclosporin A or FK506", Toxicology, 1998, vol. 131, 175-181.
Sieburg, "Aus dem Institut fur Pharmakologie und physiologische Chemie der Universitat zu Rostock. Ueber Ester aromatischer Arsenverbindungen (der p-Benzarsinsaure) mit Aminosauren und hoheren Alkoholen", Zur Biologie aromatischer Arsenverbindungen, Ztschr. f. physiol. Chem., 1916, 97 Heft 2/3, 224-245.

Hummel et al., "Modification of Bovine Pancreatic Ribonuclease A with the Site-Specific Reagent 4-Arsono-2-nitrofluorobenzene. Spectrophotometric Titration of Arsononitrophenyl Ribonuclease A Derivatives", Biochemistry, 1981, vol. 20, 4843-4852.

Hummel et al., "Chemical modification of ribonuclease A with 4-arsono-2-nitrofluorobenzene", Int. J. Peptide Protein Res., 1984, vol. 24, 1-13.

Delnomdedieu et al., "Reduction and binding of arsenate and dimethylarsinate by glutathione: a magnetic resonance study", Chemico Biological Interactions, 1994, vol. 90, 139-155.

Donoghue, N. et al., "Characterization of Redox-Active Proteins on Cell Surface", Methods in Enzymology, 2002, vol. 348, 76-86.

Hnatowich, DJ et al., "Investigations of Avidin and Biotin for Imaging Applications", 1987, The Journal of Nuclear Medicine, vol. 8, 1294-1302.

Gill, B.S., "Chemotherapeutic Susceptibility of Trypanosoma to some Arsenicals and Suramin-Tryparsamid Complex", Acta Vet., 1971, 40(2), 209-14. (English Abstract only).

Yuki, H. et al., "Synthesis of Purine and Pyrmidine Derivatives of Arsonic Acid", Chem. Pharm. Bull., 1967, 15(7), 1052-1055.

Donahue, N. et al., [9] Identification of Redox-Active Proteins on Cell Surface, Methods of Enzymology, vol. 352, 101-112, 2002.

Namgung et al., The Journal of Neuroscience 2000, 20(7), 6442-6451.

Loiseau et al., Antimicrobial Agents and Chemotherapy, 2000, 44(11) 2954-2961.

Cai et al., "Mitochondrial Control of Apoptosis: the role of cytochrome c", Biochimica et Biophysica Acta, 1998, vol. 1366, 139-148.

Lawrence, D et al., "Surface Thiols of Human Lymphocytes and Their Changes after in Vitro and in Vivo Activation," Journal of Leukocyte Biology, vol. 60, (1996), pp. 611-618.

Ryser et al., "Cell Surface Sulfhydryls are Required for the Cytotoxicity of Diphtheria Toxin but not of Ricin in Chinese Hamster Ovary Cells," Journal of Biological Chemistry, vol. 266, No. 28 (1991) pp. 18439-18442.

Mandel, R. et al., "Inhibition of a Reductive Function of the Plasma Membrane by Bacitracin and Antibodies Against Protein Disulfide-Isomerase," PNAS, vol. 90 (1993) pp. 4112-4116.

Couet, J. et al., "Cell Surface Protein Disulfide-Isomerase is Involved in the Shedding of Human Thyrotropin Receptor Ectodomain," Biochemistry, vol. 35 (1996) pp. 14800-14805.

Krishna, R. et al., "cDNA for R-Cognin: Homology with a Multifunctional Protein," PNAS, vol. 90 (1993) pp. 2950-2954.

Zai, A. et al., "Cell-Surface Protein Disulfide Isomerase Catalyzes Transnitrosation and Regulates Intracellular Transfer of Nitric Oxide," The Journal of Clinical Investigation, vol. 103, No. 3 (1999) pp. 393-399.

Essex, D. et al., "Localization of Protein Disulfide Isomerase to the External Surface of the Platelet Plasma Membrane," Blood, vol. 86, No. 6 (1995) pp. 2168-2173.

Essex, D. et al., "Protein Disulphide Isomerase Mediates Platelet Aggregation and Secretion," British Journal of Haematology, vol. 104 (1999) pp. 448-454.

Tager, M. et al., "Membrane-Bound Proteindisulfide Isomerase (PDI) is Involved in Regulation of Surface Expression of Thiols and Drug Sensitivity B-CLL Cells," Experimental Hematology, vol. 25 (1997) pp. 601-607.

Stathakis, P. et al., "Generation of Angiostatin by Reduction and Proteolysis of Plasmin: Catalysis by a Plasmin Reductase Secreted by Cultured Cells," J. Bio. Chem., vol. 272, No. 33 (1997) pp. 20641-20645.

Stathakis, P. et al., "Angiostatin Formation Involves Disulfide Bond Reduction and Proteolysis in Kringle 5 of Plasmin," J. Bio. Chem., vol. 274, No. 13 (1999) pp. 8910-8916.

Bannai, S. et al., "The Export of Glutathione from Human Diploid Cells in Culture," J. Bio. Chem., vol. 254, No. 9 (1979) pp. 3444-3450.

Holmgren, "Thioredoxin and Glutaredoxin Systems," J. Bio. Chem., vol. 264, No. 24 (1989) pp. 13963-13966.

Rosen, A. et al., "A CD4+ T Cell Line-Secreted Factor, Growth, Promoting for Normal and Leukemic B Cells, Identified as Thioredoxin," International Immunology, vol. 7, No. 4 (1995) pp. 625-633.

Halestrap, A. et al., "The Permeability Transition Pore Complex: Another View," Biochimie, vol. 84 (2002) pp. 153-166.

Desagher, S. et al., "Mitochondria as the Central Control Point of Apoptosis," Trends in Cell Biology, vol. 10 (2000) pp. 369-377.

Fantin, V. et al., "A Novel Mitochondriotoxic Small Molecule that Selectively Inhibits Tumor Cell Growth," Cancer Cell, vol. 2 (2002) pp. 29-42.

Belzacq, A. et al., "The Adenine Nucleotide Translocator in Apoptosis," Biochimie, vol. 84 (2002) pp. 167-176.

McStay, G. et al., "Role of Critical Thiol Groups on the Matrix Surface of the Adenine Nucleotide Translocase in the Mechanism of the Mitochondrial Permeability Transition Pore," Biochem. J., vol. 367 (2002) pp. 541-548.

Koch, "The Role of Angiogensis in Rheumatoid Arthritis: Recent Developments," Ann. Rheum. Dis., vol. 59 (2000) pp. 65-71.

Hayes, "Angioneogenesis in Rheumatoid Arthritis," The Lancet, vol. 354 (1999) pp. 423-424.

Anonymous, "Arthritis: The Aging Populations of Developed Countries are Likely to present a Growing market for Arthritis Therapies," Nature Biotechnology, vol. 18 (2000) pp. IT12-1T14.

Ades, E. et al., "HMEC-1: Establishment of an Immortalized Human Microvascular Endothelial Cell Line," The Journal of Investigative Dermatology, vol. 99, No. 6 (1992) pp. 683-690.

Andree, H. et al., "Binding of Vascular Anticoagulant α (VACα) to Planar Phospholipid Bilayers," J. Bio. Chem., vol. 265, No. 9 (1990) pp. 4923-4926.

Blankenberg, F. G. et al., "Will Imaging of Apoptosis Play a Role in clinical Care? A tale of Mice and Men," Apoptosis, vol. 6 (2001) pp. 117-123.

Dahmoun, M. et al., "Apoptosis, Proliferatioin, and Sex Hormone Receptors in Superficial Parts of Human Endometrium at the End of the Secretory Phase," The Journal of Clinical Endocrinology & Metabolism, vol. 84, No. 5 (1999) pp. 1737-1743.

Daly, J. et al., "New Differentiation Factor Induces ErbB2 Down-Regulation and Apoptosis of ErbB2-Overexpressing Breast Tumor Cells," Cancer Research, vol. 57 (1997) pp. 3804-3811.

Donoghue, N. et al., "Presence of Closely Spaced Protein Thiols on the Surface of Mammalian Cells," Protein Science, vol. 9, (2000) pp. 2436-2445.

Fisher, K. et al., "Cloning and Expression of Human Tissue Factor cDNA," Thrombosis Research, vol. 48 (1987) pp. 89-99.

Gottlieb, R. et al., "Apoptosis in Myocardial Ischemia-Reperfusion," Ann. N. Y. Acad. Sci., vol. 874 (1999) pp. 412-426.

Hofstra, L. et al., "Visualisation of Cell Death in vivo in Patients with Acute Myocardial Infarction," The Lancet, vol. 356 (2000) pp. 209-212.

Huang, X. et al., "Tumor Infraction in Mice by Antibody-Directed Targeting of Tissue Factor to Tumor Vasculature," Science, vol. 275 (1997) pp. 547-550.

Jiang, X. et al., "Redox Control of Exofacial protein Thiols/Disulfides by protein Disulfide Isomerase," J. Bio. Chem., vol. 274, No. 4 (1999) pp. 2416-2423.

Ju, S. et al., "Molecular and Cellular Mech Regulating T and B Cell Apop Through Fax/FasL Interaction," Intern, Rev. Immunol., vol. 18 (1999) pp. 485-513.

Krams, S. et al., "Apoptosis as a Mechanism of Tissue Injury in Liver Allograft Rejection," Seminars in Liver Disease, vol. 18, No. 2 (1998) pp. 153-167.

Nihei, O. et al., "Pharmacologic Properties of P2Z/P2X7 Receptor Characterized in Murine Dendritic Cells: Role on the Induction of Apoptosis," Blood, vol. 96, No. 3 (2000) pp. 996-1004.

O'Reilly, M. et al., "Angiostatin: A Novel Angiogensis Inhibitor That Mediates the Suppression of Metastases by a Lewis Lung Carcinoma," Cell, vol. 79 (1994) pp. 315-328.

Parker, J. et al., "The Role of Apoptosis in the Pathogenesis of the Myelodysplastic Syndromes," Int. J. Hematol., vol. 73 (2001) pp. 416-428.

* cited by examiner

A

GSAO-B

B

A

GSAO-Cy5.5

B

SUBSTANTIALLY CELL MEMBRANE IMPERMEABLE COMPOUND AND USE THEREOF

CROSS-REFERENCE TO RELATED APPLICATIONS

This application is a continuation of U.S. patent application Ser. No. 10/088,540, filed 4 Sep. 2002, now U.S. Pat. No. 7,074,766, which was the National Stage of International Application No. PCT/AU00/01143, filed 20 Sep. 2000.

TECHNICAL FIELD

The present invention relates to substantially cell-membrane impermeable compounds having the ability to inhibit redox active proteins and to methods for their synthesis, in particular, the invention relates to substantially cell-membrane impermeable trivalent organoarsenical compounds and to methods for their synthesis. The invention also relates to pharmaceutical compositions comprising these compounds and to methods of treatment of inflammatory disorders, autoimmune diseases, blood vessel diseases, thrombosis, viral infections, and haematological and solid tumours.

BACKGROUND OF THE INVENTION

Some secreted proteins undergo redox reactions, that is, transfer or shuffling of hydrogens and electrons between amino acids. The amino acid most often involved is cysteine, the redox reaction involving in particular, the cysteine thiol Redox changes in cysteine residues can lead to net reduction, net formation or net interchange of disulfide bonds.

Recent evidence suggests that cell surface proteins are under redox control, not unlike that of intracellular proteins. The reducing nature of the intracellular environment facilitates interchange between the reduced and oxidised form of closely spaced dithiols (for review see Huppa and Ploegh, 1998). In contrast, the oxidising nature of the extracellular environment is generally considered to preclude the existence of closely spaced dithiols, which are thought to exist instead as disulfide bonds or as mixed disulfides with other thiol compounds. Closely spaced thiols have the capability to interchange between the reduced dithiol and oxidised disulfide bond and are therefore likely to be important for the function of redox active proteins.

Trivalent arsenicals form high affinity ring structures with closely spaced thiols. Closely spaced dithiols include thiols that are chemically vicinal, as in 2,3-dimercaptopropanol (DMP), for example, as well as thiols brought into spatial apposition by folding (Jauhianinen et al., 1988). Due to entropic factors, the resultant cyclic dithioarsinites are markedly more stable than the noncyclic products formed from trivalent arsenicals and monothiols (Stockten and Thompson, 1946). Arsenical derivatives have been used in the past as therapeutic agents for the treatment of disease. However, the inherent toxicities of arsenical compounds and their generally unfavourable therapeutic index have essentially precluded their use as pharmaceutical agents.

Consequently, there is a need for the development of therapeutically active arsenical compounds that are relatively non-toxic and which are effective in the treatment of mammalian disease, particularly those diseases related to rapidly proliferating cells.

The present invention provides compounds wherein a chemical moiety having the ability to disrupt cell function by inhibition of redox active proteins, such as a trivalent arsenical, is linked to a substantially cell membrane impermeable pendant group. The present invention further provides for pharmaceutical compositions comprising these compounds and to methods of treatment of inflammatory disorders, autoimmune diseases, blood vessel diseases, thrombosis, viral infections, and haematological and solid tumours.

DISCLOSURE OF THE INVENTION

1. Trivalent Organoarsenical Derivatives

According to a first embodiment of the invention, there is provided a compound according to Formula I:

$$A\text{-}(L\text{-}Y)_p \quad (I)$$

wherein
A comprises at least one substantially cell-membrane impermeable pendant group;
L comprises any suitable linker and/or sparer group;
Y comprises at least one arsenoxide or arsenoxide equivalent;
p is an integer from 1 to 10; and
the sum total of carbon atoms in A and L together, is greater than 6.

The following features relate to the first embodiment of the invention.

Typically, A is hydrophilic. More typically, A may be charged, uncharged or neutral at physiological pH.

Typically, A is selected from the group consisting of natural, unnatural and synthetic amino acids, hydrophilic amines, peptides, polypeptides, oligosacchardes, detectable groups, thiol containing proteins, or a combination thereof. More typically, A is selected from the group consisting of glutathione, glucosamine, cysteinylglycine, cysteic acid, aspartic acid, glutamic acid, lysine, arginine, wherein the sulfur atom of each sulfur containing compound may be optionally oxidised to form a sulfoxide or sulfone.

Amino acid side chains are known to those of skill in the art and are listed, for instance in standard reference texts, such as King and Stansfield, A Dictionary of Genetics, $4^{th}$ Edition, Oxford University Press, 1990, the contents of which are incorporated herein by reference, Still typically, pendant group A is a detectable group, such as biotin, cy™5.5 or fluorescein.

Even more typically, A is glutathione and in one form of the invention the compound is as represented in the following Formula (II);

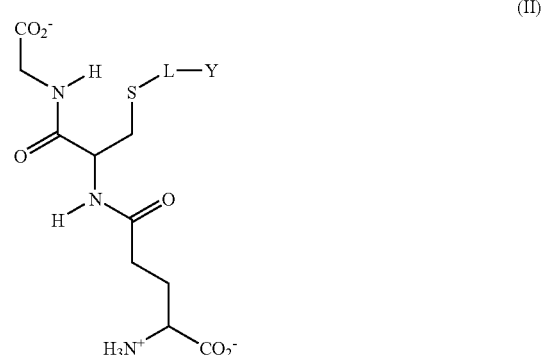

wherein L comprises any suitable linker and/or spacer group and wherein Y comprises an arsenoxide or an arsenoxide equivalent.

Typically, Y is an arsenoxide group, and can be represented by —As═O.

Typically, p is an integer from 1 to 8 More typically, p is an integer from 1 to 5. Even more typically p is an integer from 1 to 3. Yet still more typically, p is 1.

Typically, L corresponds to $(XBX')_nB'$. Typically, n is an integer from 0 to 20, more typically 0 to 15, even more typically 0 to 10, still more typically 0 to 5.

Still in accordance with the first embodiment of the invention, the following relates to $(XBX')_nB'$.

Typically, X is selected from the group consisting of —NR, —S(O)—, —S(O)O—, —S(O)$_2$—, —S(O)$_2$O—, —C(O)—, —C(S)—, —C(O)O—, C(S)O—, —C(S)S—, —P(O)(R$_1$)—, and P(O)(R$_1$)O—, or is absent;

B is selected from the group consisting of $C_1$-$C_{10}$ alkylene, $C_2$-$C_{10}$ alkenylene, $C_2$-$C_{10}$ alkynylene, $C_3$-$C_{10}$ cycloalkylene, $C_5$-$C_{10}$ cycloalkenylene, $C_3$-$C_{10}$ heterocycloalkylene, $C_5$-$C_{10}$ heterocycloalkenylene, $C_6$-$C_{12}$ arylene, heteroarlene and $C_2$-$C_{10}$ acyl;

X' is selected from the group consisting of —NR—, —O—, —S—, —Se—, —S—S—, S(O)—, —OS(O)—, OS(O)O—, —OS(O)$_2$, —OS(O)$_2$O—, —S(O)O—, —S(O)$_2$—, —S(O)$_2$O—, —OP(O)(R$_1$)—, —OP(O)(R$_1$)O—, —OP(O)(R$_1$)OP(O)(R$_1$)O—, —C(O)—, —C(S)—, —C(O)O—, C(S)O—, —C(S)S—, —P(O)(R$_1$)—, —P(O) (R$_1$)O—, and

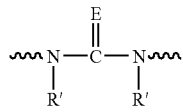

or is absent; wherein E is O, S, Se, NR or $N(R)_2^+$;

n is 0, 1 or 2; and

B' is selected from the group consisting of $C_1$-$C_{10}$ alkylene, $C_2$-$C_{10}$ alkenylene, $C_2$-$C_{10}$ alkynylene, $C_3$-$C_{10}$ cycloalkylene, $C_5$-$C_{10}$ cycloalkenylene, $C_3$-$C_{10}$ heterocycloalkylene, $C_5$-$C_{10}$ heterocycloalkenylene, $C_6$-$C_{12}$ arylene, and heteroarylene or is absent; and wherein each R is independently selected from the group consisting of hydrogen, $C_1$-$C_{10}$ alkyl, $C_2$-$C_{10}$ alkenyl, $C_2$-$C_{10}$ alkynyl, $C_3$-$C_{10}$ cycloalkyl, $C_5$-$C_{10}$ cycloalkenyl, $C_3$-$C_{10}$ heterocycloalkyl, $C_6$-$C_{10}$ heterocycloalkenyl, $C_6$-$C_{12}$ aryl, heteroaryl OR$_2$ and $C_2$-$C_{10}$ acyl;

R' is the same as R or two R' may be taken together with the nitrogen atoms to which they are attached to form a 5 or 6-membered saturated or unsaturated heterocyclic ring;

each $R_1$ is independently selected from the group consisting of hydrogen, $C_1$-$C_{10}$ alkyl, $C_2$-$C_{10}$ alkenyl, $C_2$-$C_{10}$ alkynyl, $C_3$-$C_{10}$ cycloalkyl, $C_5$-$C_{10}$ cycloalkenyl, $C_3$-$C_{10}$ heterocycloalkyl, $C_5$-$C_{10}$ heterocycloalkenyl $C_6$-$C_{12}$ aryl, heteroaryl, halo, OR2 and $N(R)_2$;

each $R_2$ is independently selected from the group consisting of hydrogen, $C_1$-$C_{10}$ alkyl, $C_1$-$C_{10}$ alkenyl, $C_2$-$C_{10}$ alkynyl, $C_3$-$C_{10}$ cycloalkyl $C_3$-$C_{10}$ cycloalkenyl, $C_3$-$C_{10}$ heterocycloalkyl, $C_5$-$C_{10}$ heterocycloalkenyl, $C_6$-$C_{12}$ aryl, heteroaryl and $C(O)R_5$;

each $R_5$ is independently selected from the group consisting of hydrogen, $C_1$-$C_{10}$ alkyl, $C_2$-$C_{10}$ alkenyl, $C_2$-$C_{10}$ alkynyl, $C_3$-$C_{10}$ cycloalkyl, $C_3$-$C_{10}$ cycloalkenyl, $C_3$-$C_{10}$ heterocioalkyl, $C_5$-$C_{10}$ heterocycloalkenyl, $C_6$-$C_{12}$ aryl, heteroaryl, $C_1$-$C_{10}$ alkoxy, $C_3$-$C_{10}$ alkenyloxy, $C_3$-$C_{10}$ alkynyloxy, $C_3$-$C_{10}$ cycloalkyloxy, $C_5$-$C_{10}$ cycloalkenyloxy, $C_3$-$C_{10}$ heterocycloalkyloxy) $C_5$-$C_{10}$ heterocycloalkenyloxy, $C_6$-$C_{12}$ aryloxy, heteroaryloxy, $C_1$-$C_{10}$ alkylthio, $C_3$-$C_{10}$ alkenylthio, $C_3$-$C_{10}$ alkynylthio, $C_3$-$C_{10}$ cycloalkylthio, $C_5$-$C_{10}$ cycloalkenylihio, $C_3$-$C_{10}$ heterocycloalkylthio, $C_5$-$C_{10}$ heterocycloalkenylthio, $C_6$-$C_{12}$ arylthio, heteroarylthio, OH, SH and $N(R)_2$;

wherein for each instance that B and/or B' is arylene, the substituents directly attached to the respective arylene rings (including arsenoxide or arsenoxide equivalent) may be in a para-, meta- or ortho-relationship; and wherein each alkylene, alkenylene, alkynylene, cycloalkylene, cycloalkenylene, heterocycloalkylene, heterocycloalkenylene, arylene, heteroarylene and acyl may be independently substituted with hydrogen, $C_1$-$C_{10}$ alkyl, $C_2$-$C_{10}$ alkenyl, $C_2$-$C_{10}$ alkynyl, $C_3$-$C_{10}$ cycloalkyl, $C_5$-$C_{10}$ cycloalkenyl, $C_3$-$C_{10}$ heterocycloalkyl, $C_5$-$C_{10}$ heterocycloalkenyl, $C_6$-$C_{12}$ aryl, heteroaryl, cyano, cyanate, isocyanate, $OR_{2a}$, $SR_6$, nitro, arsenoxide, —S(O)R$_3$, —OS(O)R$_3$, —S(O)$_2$R$_3$, —OS(O)$_2$R$_3$, —P(O)R$_4$R$_4$, —OP(O)R$_4$R$_4$, —N(R")$_2$, —NRC(O)(CH$_2$)$_m$Q, —C(O)R$_5$;

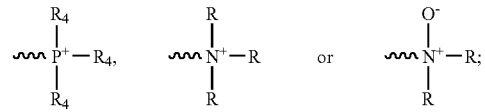

wherein R, $R_1$ and $R_5$ are as defined above; and $R_{2a}$ is selected from the group consisting of hydrogen, $C_1$-$C_5$ alkyl, $C_2$-$C_5$ alkenyl, $C_2$-$C_5$ alkynyl, $C_3$-$C_{10}$ cycloalkyl, $C_5$-$C_{10}$ cycloalkenyl, $C_6$-$C_{12}$ aryl —S(O)R$_3$, —S(O)$_2$R$_3$, —P(O)(R$_4$)$_2$, $N(R)_2$ and —C(O)R$_5$;

each $R_3$ is independently selected from the group consisting of hydrogen, $C_1$-$C_{10}$ alkyl, $C_2$-$C_{10}$ alkenyl, $C_2$-$C_{10}$ alkynyl, $C_3$-$C_{10}$ cycloalkyl, $C_5$-$C_{10}$ cycloalkenyl, $C_3$-$C_{10}$ heterocycloalkyl, $C_5$-$C_{10}$ heterocycloalkenyl, $C_6$-$C_{12}$ aryl, heteroaryl, $C_1$-$C_{10}$ alkoxy, $C_3$-$C_{10}$ alkenyloxy, $C_3$-$C_{10}$ alkynyloxy, $C_3$-$C_{10}$ cycloalkyloxy, $C_5$-$C_{10}$ cycloalkenyloxy, $C_3$-$C_{10}$ heterocycloalkyloxy, $C_5$-$C_{10}$ heterocycloalkenyloxy, $C_6$-$C_{12}$ aryloxy, heteroaryloxy, $C_1$-$C_{10}$ alkylthio, $C_3$-$C_{10}$ alkenylthio, $C_3$-$C_{10}$ alkynylthio, $C_3$-$C_{10}$ cycloalkylthio, $C_5$-$C_{10}$ cycioalkenylthio, $C_3$-$C_{10}$ heterocycloalkylthio, $C_5$-$C_{10}$ heterocycloalkenylthio, $C_6$-$C_{12}$ arylthio, heteroarylthio and $N(R)_2$;

each $R_4$ is independently selected from the group consisting of hydrogen, $C_1$-$C_{10}$ alkyl, $C_2$-$C_{10}$ alkenyl, $C_2$-$C_{10}$ alkynyl, $C_3$-$C_{10}$ cycloalkyl, $C_5$-$C_{10}$ cycloalkenyl, $C_3$-$C_{10}$ heterocyctoalkyl, $C_5$-$C_{10}$ heterocycloalkenyl, $C_6$-$C_{12}$ aryl, heteroaryl, $C_1$-$C_{10}$ alkoxy, $C_3$-$C_{10}$ alkenyloxy, $C_3$-$C_{10}$ alkynyloxy, $C_3$-$C_{10}$ cycloalkyloxy, $C_5$-$C_{10}$ cycloalkenyloxy, $C_3$-$C_{10}$ heterocycloalkyloxy, $C_5$-$C_{10}$ heterocycloalkenyloxy, $C_6$-$C_{12}$ aryloxy, heteroaryloxy, $C_1$-$C_{10}$ alkylthio, $C_3$-$C_{10}$ alkenylthio, $C_3$-$C_{10}$ alkynylthio, $C_3$-$C_{10}$ cycloalkylthio, $C_5$-$C_{10}$ cycloalkenylthio, $C_3$-$C_{10}$ heterocycloalkylthio, $C_5$-$C_{10}$ heterocycloalkenylthio, $C_6$-$C_{12}$ arylthio, heteroaryithior halo and $N(R)_2$;

$R_6$ is selected from the group consisting of $C_1$-$C_{10}$ alkyl, $C_2$-$C_{10}$ alkenyl, $C_2$-$C_{10}$ alkynyl, $C_3$-$C_{10}$ cycloalkyl, $C_5$-$C_{10}$ cycloalkenyl, $C_3$-$C_{10}$ heterocycloalkyl, $C_5$-$C_{10}$ heterocycloalkenyl, $C_6$-$C_{12}$ aryl, heteroaryl, $C_1$-$C_{10}$ alkylthio, $C_3$-$C_{10}$ alkenylthio, $C_3$-$C_{10}$ alkynylthio, $C_3$-$C_{10}$ cycloalkylthio, $C_5$-$C_{10}$ cycloalkenylthio, $C_3$-$C_{10}$ heterocycloalkylthio, $C_5$-$C_{10}$ heterocycloalkenylthio, $C_6$-$C_{12}$ arylthio, heteroarylthio, —S(O)R$_3$, —S(O)$_2$R$_3$ and —C(O)$_5$, R" is the same as R or two R" taken together with the N atom to which they are attached may form a saturated, unsaturated or aromatic heterocyclic ring system;

Q is selected from halogen and —OS(O)₂Q₁; wherein Q₁ is selected from $C_1$-$C_4$ alkyl $C_1$-$C_4$ perfluoroalkyl, phenyl, p-methylphenyl; and m is 1 to 5.

More typically, X is selected from the group consisting of —C(O)—, —C(S)—, —C(O)O—, C(S)O—, and —C(S)S—, or is absent;

B is selected from the group consisting of $C_1$-$C_5$ alkylene, $C_2$-$C_5$ alkenylene, $C_2$-$C_5$ alkynylene, $C_3$-$C_{10}$ cycloalkylene, $C_5$-$C_{10}$ cycloalkenylene, $C_6$-$C_{12}$ arylene and $C_2$-$C_5$ acyl;

X' is selected from the group consisting of —O—, —S—, —NR—, —S—S—, —S(O)—, —S(O)₂—, —P(O)(R₁)—, —OP(O)(R₁)—, OP(O)(R₁)O—, —OP(O)(R₁)OP(O)(R₁)O—, —C(O)—, —C(S)—, —O(O)O—, C(S)O—, —C(S)S—, —Se—,

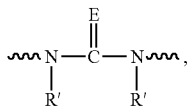

or is absent, wherein E is O, S or N(R)₂⁺;

n is 0, 1 or 2; and

B' is $C_1$-$C_5$ selected from the group consisting of alkylene, $C_2$-$C_5$ alkenylene, $C_2$-$C_5$ alkynylene, $C_3$-$C_{10}$ cycloalkylene, $C_5$-$C_{10}$ cycloalkenylene, and $C_6$-$C_{12}$ arylene, or is absent; and wherein each R is independently selected from the group consisting of hydrogen, $C_1$-$C_5$ alkyl, $C_2$-$C_5$ alkenyl, $C_2$-$C_5$ alkynyl, $C_3$-$C_{10}$ cycloalkyl, $C_5$-$C_{10}$ cycloalkenyl, $C_6$-$C_{12}$ aryl, OR₂ and $C_2$-$C_{10}$ acyl;

R' is the same as R;

each R₁ is independently selected from the group consisting of hydrogen, $C_1$-$C_5$ alkyl, $C_2$-$C_5$ alkenyl, $C_2$-$C_5$ alkynyl, $C_3$-$C_{10}$ cycloalkyl, $C_5$-$C_{10}$ cycloalkenyl, $C_6$-$C_{12}$ aryl, halo, OR₂ and N(R)₂;

each R₂ is independently selected from the group consisting of hydrogen, $C_1$-$C_5$ alkyl, $C_2$-$C_5$ alkenyl, $C_2$-$C_5$ alkynyl, $C_3$-$C_{10}$ cycloalkyl, $C_5$-$C_{10}$ cycloalkenyl, $C_6$-$C_{12}$ aryl, and —C(O)R₅;

each R₅ is independently selected from the group consisting of hydrogen, $C_1$-$C_5$ alkyl, $C_2$-$C_5$ alkenyl, $C_2$-$C_5$ alkynyl, $C_3$-$C_{10}$ cycloalkyl, $C_5$-$C_{12}$ cycloalkenyl, $C_6$-$C_{12}$ aryl, $C_1$-$C_5$ alkoxy, $C_3$-$C_5$ alkenyloxy, $C_3$-$C_5$ alkynyloxy, $C_3$-$C_{10}$ cycloalkyloxy, $C_5$-$C_{10}$ cycloalkenyloxy, $C_6$-$C_{12}$ aryloxy, $C_1$-$C_5$ alkylthio, $C_3$-$C_5$ alkenylthio, $C_3$-$C_5$ alkynylthio, $C_3$-$C_{10}$ cycloalkylthio, $C_5$-$C_{10}$ cycloalkenylthio, $C_6$-$C_{12}$ arylthio, OH, SH, and N(R)₂;

wherein for each instance that B and/or B' is arylene, the substituents directly attached to the respective arylene rings (including arsenoxide or arsenoxide equivalent), may be in a para-, meta- or ortho-relationship, and wherein each alkylene, alkenylene, alkynylene, cycloalkylene, cycloalkenylene, arylene, and acyl may be independently substituted with hydrogen, $C_1$-$C_5$ alkyl, $C_2$-$C_5$ alkenyl, $C_2$-$C_5$ alkynyl, $C_3$-$C_{10}$ cycloalkyl, $C_5$-$C_{10}$ cycloalkenyl, $C_6$-$C_{12}$ aryl, cyano, halo, cyanate, isocyanate, OR₂ₐ, SR₆, nitro, arsenoxide, —S(O)R₃, —S(O)R₃, —S(O)₂R₃, —OS(O)₂R₃, —P(O)R₄R₄, —OP(O)R₄R₄, —N(R')₂, NRC(O)(CH₂)ₘQ, —C(O)R₅,

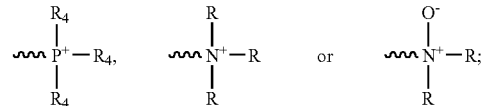

wherein R, R₁ and R₅ are as defined above; and

R₂ₐ is selected from the group consisting of hydrogen, $C_1$-$C_5$ alkyl, $C_2$-$C_5$ alkenyl, $C_2$-$C_5$ alkynyl, $C_3$-$C_{10}$ cycloalkyl, $C_5$-$C_{10}$ cycloalkenyl, $C_6$-$C_{12}$ aryl, —S(O)R₃, —S(O)₂R₃, —P(O)(R₄)₂, N(R)₂ and —C(O)R₅;

each R₃ is independently selected from the group consisting of hydrogen, $C_1$-$C_5$ alkyl, $C_2$-$C_5$ alkenyl, $C_2$-$C_5$ alkynyl, $C_3$-$C_{10}$ cycloalkyl, $C_5$-$C_{10}$ cycloalkenyl $C_6$-$C_{12}$ aryl, $C_1$-$C_5$ alkoxy, $C_3$-$C_5$ alkenyloxy, $C_3$-$C_5$ alkynyloxy, $C_3$-$C_{10}$ cycloalkyloxy, $C_5$-$C_{10}$ cycloalkenyloxy, $C_6$-$C_{12}$ aryloxy, $C_1$-$C_5$ alkylthio, $C_3$-$C_5$ alkenylthio, $C_3$-$C_5$ alkynylthio, $C_3$-$C_{10}$ cycloalkylthio, $C_5$-$C_{10}$ cycloalkenylthio, $C_6$-$C_{12}$ arylthio and N(R)₂;

each R₄ is independently selected from the group consisting of hydrogen, $C_1$-$C_5$ alkyl, $C_2$-$C_5$ alkenyl, $C_2$-$C_5$ alkynyl, $C_3$-$C_{10}$ cycloalkyl, $C_5$-$C_{10}$ cycloalkenyl, $C_6$-$C_{12}$ aryl, $C_1$-$C_5$ alkoxy, $C_3$-$C_5$ alkenyloxy, $C_3$-$C_5$ alkynyloxy, $C_3$-$C_{10}$ cycloalkyloxy, $C_5$-$C_{10}$ cycloalkenyloxy, $C_6$-$C_{12}$ aryloxy, $C_1$-$C_5$ alkylthio, $C_3$-$C_5$ alkenylthio, $C_3$-$C_5$ alkynylthio, $C_3$-$C_5$ cycloalkylthio, $C_5$-$C_5$ cycloalkenylthio $C_6$-$C_{12}$ arylthio, halo and N(R)₂;

R₆ is independently selected from the group consisting of $C_1$-$C_5$ alkyl, $C_2$-$C_5$ alkenyl, $C_2$-$C_5$ alkynyl, $C_3$-$C_{10}$ cycloalkyl, $C_5$-$C_{10}$ cycloalkenyl, $C_6$-$C_{12}$ aryl, $C_1$-$C_5$ alkylthio, $C_3$-$C_5$ alkenylthio, $C_3$-$C_5$ alkynylthio, $C_3$-$C_{10}$ cycloalkylthio, $C_5$-$C_{10}$ cycloalkenylthio, $C_6$-$C_{12}$ arylthio, —S(O)R₃, —S(O)₂R₃ and —C(O)R₅.

R" is the same as R;

Q is selected from the group consisting of halogen and —OS(O)₂Q₁; wherein Q₁ is selected from $C_1$-$C_4$ alkyl, $C_1$-$C_4$ perfluoroalkyl, phenyl, p-methylphenyl; and m is 1 to 5.

Even more typically, X is absent;

B is selected from the group consisting of $C_1$-$C_5$ alkylene, $C_6$-$C_{12}$ arylene and $C_2$-$C_5$ acyl;

X' is selected from the group consisting of —O—, —S—, —NR—, —S—S—, —S(O)—, —S(O)₂—, —P(O)(R₁)—, —C(O)—, —C(S)—, —C(O)O—, C(S)O—, —Se—, and

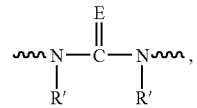

or absent; wherein E is O, S or N(R)₂⁺;

n is 0, 1 or 2; and

B' is $C_1$-$C_5$ alkylene, $C_6$-$C_{12}$ arylene or is absent; and wherein each R is independently selected from the group consisting of hydrogen, $C_1$-$C_5$ alkyl, $C_3$-$C_{10}$ cycloalkyl $C_6$-$C_{12}$ aryl, OR₂ and $C_2$-$C_5$ acyl;

R' is the same as R;

each R₁ is independently selected from the group consisting of hydrogen, $C_1$-$C_5$ alkyl, $C_3$-$C_{10}$ cycloalkyl, $C_6$-$C_{12}$ aryl, halo, OR₂ and N(R)₂;

each $R_2$ is independently selected from the group consisting of hydrogen, $C_1$-$C_5$ alkyl, $C_3$-$C_{10}$ cycloalkyl, $C_6$-$C_{12}$ aryl and —C(O)$R_5$;

each $R_5$ is independently selected from the group consisting of hydrogen, $C_1$-$C_5$ alkyl, $C_2$-$C_5$ alkenyl, $C_3$-$C_{10}$ cycloalkyl, $C_5$-$C_{10}$ cycloalkenyl, $C_6$-$C_{12}$ aryl, $C_1$-$C_5$ alkoxy, $C_3$-$C_5$ alkenyloxy, $C_3$-$C_{10}$ cycloalkyloxy, $C_5$-$C_{10}$ cycloalkenyloxy, $C_6$-$C_{12}$ aryloxy, $C_1$-$C_5$ alkylthio, $C_3$-$C_5$ alkenylthio, $C_3$-$C_{10}$ cycloalkylthio, $C_5$-$C_{10}$ cycloalkenylthio, $C_6$-$C_{12}$ arylthio, OH, SH and N(R)$_2$, wherein for each instance that B and/or B' is arylene, the substituents directly attached to the respective arylene rings (including arsenoxide or arsenoxide equivalent) may be in a para-, meta- or ortho-relationship, and wherein each alkylene, alkenylene, alkynylene, cycloalkylene, cycloalkenylene, arylene, and acyl may be independently substituted with hydrogen, $C_1$-$C_5$ alkyl, $C_2$-$C_5$ alkenyl, $C_2$-$C_5$ alkynyl, $C_3$-$C_{10}$ cycloalkyl, $C_5$-$C_{10}$ cycloalkenyl, $C_6$-$C_{12}$ aryl, halo, cyano, cyanate; isocyanate, OR$_{2a}$, SR$_6$, nitro, arsenoxide, —S(O)R$_3$, —OS(O)R$_3$, —S(O)$_2$R$_3$, —OS(O)$_2$R$_3$, —P(O)R$_4$R$_4$, —OP(O)R$_4$R$_4$, N(R")$_2$, —NRC(O)(CH$_2$)$_m$Q, —C(O)R$_5$,

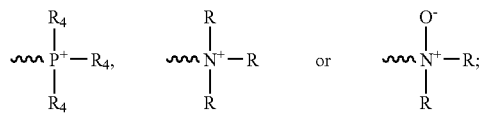

wherein R, $R_1$, and $R_5$ are as defined above; and $R_{2a}$ is selected from the group consisting of hydrogen, $C_1$-$C_5$ alkyl, $C_3$-$C_{10}$ cycloalkyl, $C_6$-$C_{12}$ aryl, —S(O)R$_3$, —S(O)$_2$R$_3$, —P(O)(R$_4$)$_2$ and —C(O)R$_5$;

each $R_3$ is independently selected from the group consisting of hydrogen, $C_1$-$C_5$ alkyl, $C_3$-$C_{10}$ cycloalkyl, $C_6$-$C_{12}$ aryl, $C_1$-$C_5$ alkoxy, $C_3$-$C_{10}$ cycloalkyloxy, $C_6$-$C_{12}$ aryloxy, $C_1$-$C_5$ alkythio, $C_3$-$C_{10}$ cycloalkylthio, $C_6$-$C_{12}$ arylthio and N(R)$_2$;

each $R_4$ is independently selected from the group consisting of hydrogen, $C_1$-$C_5$ alkyl, $C_3$-$C_{10}$ cycloalkyl, $C_6$-$C_{12}$ aryl, $C_1$-$C_5$ alkoxy, $C_3$-$C_{10}$ cycloalkyloxy, $C_6$-$C_{12}$ aryloxy, halo and N(R)$_2$;

$R_6$ is selected from the group consisting of $C_1$-$C_5$ alkyl, $C_3$-$C_{10}$ cycloalkyl, $C_6$-$C_{12}$ aryl, $C_1$-$C_5$ alkylthio, $C_3$-$C_{10}$ cycloalkylthio, $C_6$-$C_{12}$ arylthio, —S(O)R$_3$, —S(O)$_2$R$_3$ and —C(O)R$_5$, R" is the same as R;

Q is selected from halogen and —OS(O)$_2$Q$_1$; wherein Q$_1$ is selected from $C_1$-$C_4$ alkyl, $C_1$-$C_4$ perfluoroalkyl, phenyl, p-methylphenyl, and m is 1to 5.

Still more typically, X is absent;

B is selected from the group consisting of $C_1$C$_5$ alkylene, $C_6$-$C_{12}$ arylene and $C_2$-$C_5$ acyl;

X' is selected from the group consisting of —O—, —S—, —NR—, —C(O)—, and —C(O)O—, or is absent;

n is 1; and

B' is $C_1$-$C_5$ alkylene, $C_6$-$C_{12}$ arylene or is absent; and

R is selected from the group consisting of hydrogen, $C_1$-$C_5$ alkyl, $C_6$-$C_{12}$ aryl and $C_2$-$C_5$ acyl;

wherein for each instance that B and/or B' is arylene, the substituents directly attached to the respective arylene rings (including arsenoxide or arsenoxide equivalent), may be in a para-, meta- or ortho-relationship, and wherein each alkylene, arylene, and acyl may be independently substituted with hydrogen, $C_1$-$C_5$ alkyl, $C_2$-$C_5$ alkenyl, $C_2$-$C_5$ alkynyl, $C_3$-$C_{10}$ cycloalkyl, $C_6$-$C_{10}$ cycloalkenyl, $C_6$-$C_{12}$ aryl, halo, cyano, cyanate, isocyanate, OR$_{2a}$, SR$_6$, nitro, arsenoxide, —S(O)R$_3$, —S(O)$_2$R$_3$, —P(O)R$_4$R$_4$, —N(R")$_2$, —NRC(O)(CH$_2$)$_m$Q, —C(O)R$_5$,

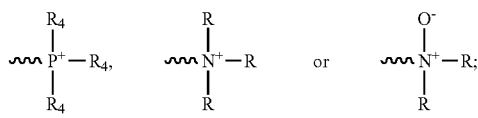

wherein each R is independently selected from the group consisting of hydrogen, $C_1$-$C_5$ to alkyl, $C_6$-$C_{12}$ aryl and $C_2$-$C_5$ acyl;

$R_{2a}$ is selected from the group consisting of hydrogen, $C_1$-$C_5$ alkyl, $C_6$-$C_{12}$ aryl, —S(O)R$_3$, —S(O)$_2$R$_3$, —P(O)(R$_4$)$_2$ and —C(O)R$_5$;

each $R_3$ is independently selected from the group consisting of hydrogen, $C_1$-$C_5$ alkyl, $C_6$-$C_{12}$ aryl, $C_1$-$C_5$ alkoxy, $C_6$-$C_{12}$ aryloxy, $C_1$-$C_5$ alkylthio, and $C_6$-$C_{12}$ arylthio;

each $R_4$ is independently selected from the group consisting of hydrogen, $C_1$-$C_5$ alkyl, $C_6$-$C_{12}$ aryl, $C_1$-$C_5$ alkoxy, $C_6$-$C_{12}$ aryloxy, $C_1$-$C_5$ alkylthio, $C_6$-$C_{12}$ arylthio, halo and N(R)$_2$;

each $R_5$ is independently selected from the group consisting of hydrogen, $C_1$-$C_5$ alkyl, $C_6$-$C_{12}$ aryl, $C_1$-$C_5$ alkoxy, $C_6$-$C_{12}$ aryloxy, $C_1$-$C_5$ alkylthio, $C_6$-$C_{12}$ arylthio, OH, SH and N(R)$_2$;

$R_6$ is selected from the group consisting of $C_1$-$C_5$ alkyl, $C_6$-$C_{12}$ aryl, $C_1$-$C_5$ alkylthio, $C_6$-$C_{12}$ arylthio, —S(O)R$_3$, —S(O)$_2$R$_3$ and —C(O)R$_5$, R" is the same as R above;

Q is selected from halogen and —OS(O)$_2$Q$_1$; wherein Q$_1$ is selected from $C_1$-$C_4$ alkyl, $C_1$-$C_4$ perfluoroalkyl, phenyl, p-methylphenyl; and m is 1to 5.

Yet still more typically, X is absent;

B is $C_2$-$C_5$ acyl;

X' is NR;

n is 1

B' is phenylene, and

R is H;

wherein the substituents directly attached to the phenylene ring may be in a para-, meta- or ortho-relationship, as exemplified by Formula (III),

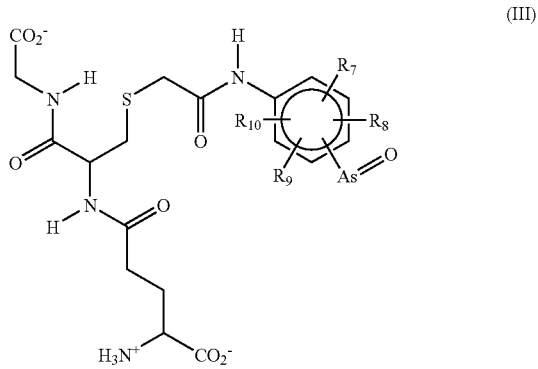

wherein $R_7$ to $R_{10}$ are independently selected from the group consisting of hydrogen, $C_1$-$C_5$ alkyl, $C_6$-$C_{12}$ aryl, halogen, hydroxy, amino, nitro, carboxy, $C_1$-$C_5$ alkoxy, —OS(O)$_2R_3$ and —NHC(O)CH$_2$Q wherein Q is halogen, —OS(O)$_2$CH$_3$, —OS(O)$_2C_6H_5$ and —OS(O)$_2$-p tolyl; and wherein, when an of $R_7$ to $R_{10}$ is $C_1$-$C_5$ alkyl, $C_6$-$C_{12}$ aryl, $C_1$-$C_5$ alkoxy, —OS(O)$_2R_3$ it is capable of forming a fused ring with the phenylene; and further wherein, at least one of $R_7$ to $R_{10}$ is $C_1$-$C_5$ alkyl, $C_6$-$C_{12}$ aryl, $C_1$-$C_5$ alkoxy, or —OS(O)$_2R_3$, in combination with at least any one other of $R_7$ to $R_{10}$, is capable of forming a fused ring with the phenylene.

More typically, $R_7$ to $R_{10}$ are independently selected from the group consisting of hydrogen, halogen, hydroxy, amino, nitro, cyano, carboxy, $C_1$-$C_5$ alkoxy, methyl, ethyl, isopropyl, tert-butyl, phenyl and —NHC(O)CH$_2$Q wherein Q is halogen, —OS(O)$_2$CH$_3$, —OS(O)$_2C_6H_5$ and —CS(O)$_2$p tolyl.

Further, when B' is arylene, the substituents attached to the arylene ring are typically in an ortho-, meta- or para-relationship to the —As═O More typically the substituents are in a meta- or para-relationship to the —As═O group.

More preferably there is provided the compound 4-(N-(S-glutathionylacetyl)amino)-phenylarsenoxide, which can be abbreviated to GSAO, according to Formula (V):

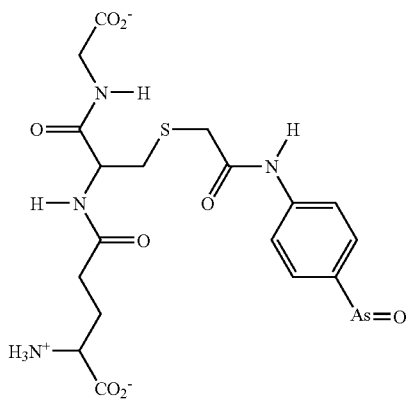

(IV)

There are also provided by the present invention compounds according to Formula (V):

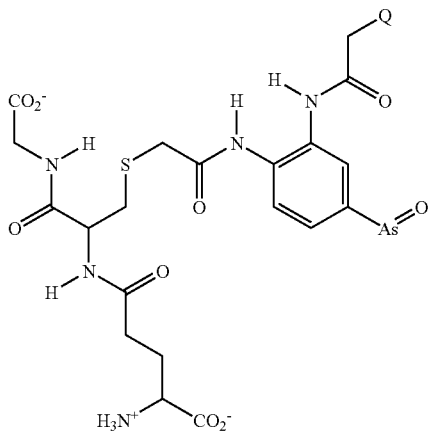

(V)

wherein Q is any halogen. For example, the invention provides the compounds 3-(N-(fluoroacetolamino)-4-(N-(S-glutathionylacetyl)amino)phenylarsenoxide, which may be abbreviated to GSFAO, 3-(N-(chloroacetyl)amino)-4-(N-(S-glutathionylacetyl)amino)phenylarsenoxide, which may be abbreviated to GSCAO, 3-(N-(bromoacetyl)amino)-4-(N-(S-glutathionylacetyl)amino)-phenylarsenoxide, which may be abbreviated to GSBAO, and 3-(N-(iodoacetyl)amino)-4-(N-(S-glutathionylacetyl)amino)phenylarsenoxide, which may be abbreviated to GSIAO.

In another preferred form of the compounds of the invention there is provided a compound according to Formula (VI):

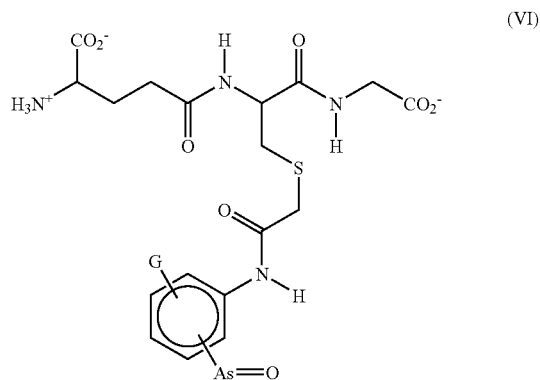

(VI)

wherein G is selected from the group consisting of hydrogen, halogen, hydroxy, amino, nitro, cyano, carboxy, $C_1$-$C_5$ alkoxy, $C_1$-$C_5$ alkyl and $C_6$-$C_{12}$ aryl and —NHC(O)CH$_2$Q, wherein Q is halogen, —OS(O)$_2$CH$_3$, —OS(O)$_2C_6H_5$ or —OS(O)$_2$-p tolyl.

Typically, G is selected from the group consisting of hydrogen, halogen, hydroxy, amino, nitro, carboxy, $C_1$-$C_5$ alkoxy, methyl, ethyl, iso-propyl, tert-butyl, phenyl, and —NHC(O)CH$_2$Q, wherein Q is the group consisting of halogen, —OS(O)$_2$CH$_3$, —OS(O)$_2C_6H_5$ and —OS(O)$_2$-p tolyl.

More typically, in a compound of Formula VI, G is hydroxy, fluorine, amino, or nitro.

Typically, group G is in an ortho-, meta- or para-relationship to the arsenoxide group, more typically an ortho- or para-relationship.

Typically the activity of the arsenic atom may be modified by the group G, when G and the arsenic atom are in an ortho or para relationship to one another. For example, when G is an electron donating group such as OH (ionised to O— at physiological pH), the arsenic atom should be deactivated towards dithiols and so become more selective, only reacting with very reactive dithiols. Alternatively, when G is an electron withdrawing group, such as NO$_2$, electron density would be drawn away from the arsenic atom, making it more reactive to all dithiols. Selective inhibition of some redox proteins and not others may be achieved by manipulation of G.

According to a second embodiment of the invention there is provided a compound as defined in accordance with the first embodiment of the invention, wherein the arsenoxide group (—As═O) is replaced by an arsenoxide equivalent.

An arsenoxide equivalent is any dithiol reactive species that shows essentially the same affinity towards dithiols as —As═O. Typically, arsenoxide equivalent includes dithiol reactive entities, such as As, Ge, Sn and Sb species. More typically an arsenoxide equivalent can be represented by -D($Z_1$)($Z_2$). Arsenoxide equivalents are expected to exhibit identical or substantially identical activity to that of the corresponding arsenoxide.

Typically, for arsenoxide equivalents of the form -D(Z$_1$)(Z$_2$), D will be, for example, As RSn, Sb, or RGe, and Z$_1$ and Z$_2$ will be labile groups (i.e. groups easily displaced under physiological conditions). Z$_1$ and Z$_2$, may be identical or different, and may either be connected or independent from each other (bound only to the arsenic atom).

Suitable arsenoxide equivalents include the following:

wherein Z$_1$ and Z$_2$ are selected from the group consisting of OH, C$_1$-C$_{10}$ alkoxy, C$_6$-C$_{10}$ aryloxy, C$_1$-C$_{10}$ alkylthio, C$_6$-C$_{10}$ arylthio, C$_1$-C$_{10}$ alkylseleno, C$_6$-C$_{10}$ arylseleno, F, Cl, Br and I;

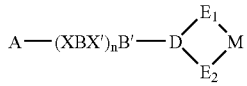

wherein E$_1$=E$_2$=O, E$_1$=O and E$_2$=S or E$_1$=E$_2$=S; M is R'" and R"" are independently selected from the group consisting of hydrogen, C$_1$-C$_{10}$ alkyl, C$_6$-C$_{12}$ aryl, halogen, C$_1$-C$_{10}$ alkoxy, C$_6$-C$_{10}$ aryloxy, hydroxy and carboxy; and n=1 to 10.

For arsenoxide equivalents of the form D(Z$_1$)(Z$_2$), when D is As and Z$_1$ and Z$_2$ are OH, the arsenoxide equivalent may be in equilibrium with polymeric species, as depicted below.

wherein X$_3$=NH, Y$_1$=O; X$_3$=Y$_1$=O or X$_3$=S, Y$_1$=O, and R' is selected from the group consisting of hydrogen, C$_1$-C$_{10}$ alkyl, C$_6$-C$_{12}$ aryl, and carboxy, or is one of the twenty amino acid side chains;

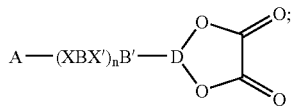

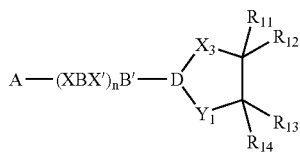

wherein X$_3$=Y$_1$=O; X$_3$=NH, Y$_1$=O; X$_3$=S, Y$_1$=O, X$_3$=Y$_1$=NH; or X$_3$=S, Y$_1$=NH and R$_{11}$ to R$_{14}$ are selected from the group consisting of hydrogen, C$_1$-C$_{10}$ alkyl, C$_6$-C$_{12}$ aryl, and CO$_2$H;

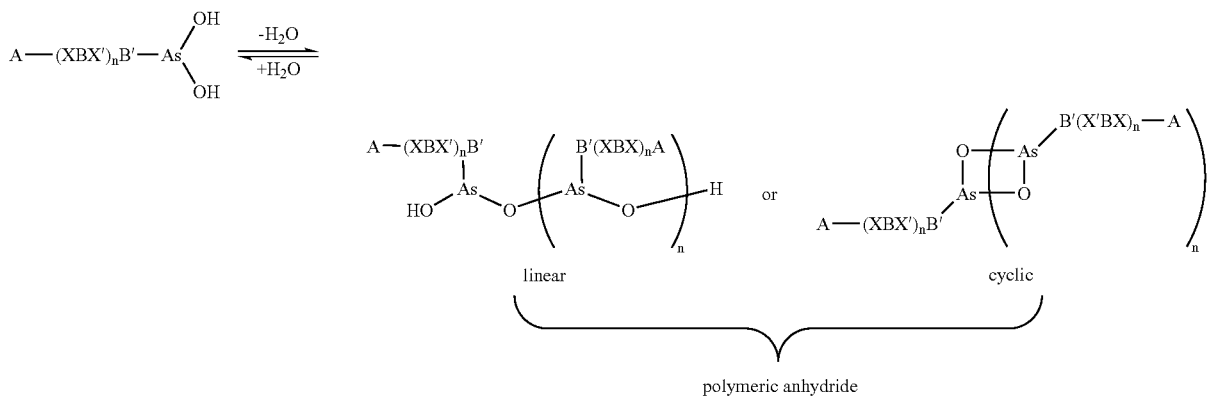

linear       cyclic polymeric anhydride

In respect of the equilibrium depicted above, arsenic is one of many elements whose hydroxy species exist in equilibrium with the corresponding polymeric anhydrides (Doak & Freedman, 1970). Therefore, arsenoxide compounds may actually exist as low or medium molecular weight polymers (e.g. n=3 to 6). However, the dehydration reaction is reversible, and therefore soluble polymeric anhydrides are expected to behave as arsenoxide equivalents, that is, they are expected to bind to closely spaced dithiols in substantially the same-way as the monomeric —As(OH)$_2$ species.

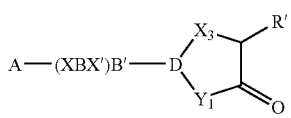

wherein X$_3$=Y$_1$=O, or X$_3$=NH, Y$_1$=O; and R$_{11}$ to R$_{14}$ are selected from the group consisting of hydrogen, C$_1$-C$_{10}$ alkyl, C$_6$-C$_{12}$aryl, halogen, C$_1$-C$_{10}$ alkoxy, and CO$_2$H.

Typically, (XBX·˙)$_n$B' is as defined above in accordance with the first embodiment of the Invention.

The compounds of the invention may be linked to detector groups.

Typically, the detector group may be a chemical group, for example, biotin, fluorescein, cy™5.5 or a group comprising a transition element.

Alternatively, the detector group is a radionucleide, such as $^{3}H$, $^{14}C$, $^{32}P$, $^{33}P$, $^{35}S$, $^{125}I$, $^{131}I$, $^{123}I$, $^{111}In$, $^{105}Rh$, $^{153}Sm$, $^{67}Cu$, $^{67}Ga$, $^{166}Ho$, $^{177}Lu$, $^{186}Re$, $^{188}Re$, and $^{99m}Tc$.

More typically, the radionucleide detector group is $^{3}H$ or $^{14}C$.

According to a third embodiment of the invention, there is provided a process for preparing a compound of any one of the first or second embodiments of the invention, wherein said process comprises reacting at least one substantially cell-membrane impermeable group (A) with a linker and/or spacer group $(XBX')_nB'$, to which is attached at least one arsenoxide or arsenoxide equivalent (Y).

A person skilled in the art will recognise that the specific order of reactions will be dependent on the particular compound of the invention that is being produced.

In one form of the invention, the process typically comprises reacting glutathione with a suitable linker and/or spacer group $(XBX')_nB'$ to which is attached at least one arsenoxide or arsenoxide equivalent (Y), under suitable reaction conditions.

2. Pharmaceutical/Therapeutic Compositions and Uses Thereof

According to a fourth embodiment of the invention, there is provided a pharmaceutical composition comprising a compound of either of the first or second embodiments of the invention, together with a pharmaceutically acceptable carrier, adjuvant and/or diluent According to a fifth embodiment of the invention, there is provided a process for preparing a pharmaceutical composition as defined in the fourth embodiment of the invention, wherein said process comprises mixing a compound as defined in either of the first or second embodiments of the invention with a pharmaceutically acceptable carrier, adjuvant and/or diluent.

According to a sixth embodiment of the invention, there is provided a method of treatment and/or prophylaxis of disease in a vertebrate in need of said treatment and/or prophylaxis, wherein said method comprises administering to the vertebrate a therapeutically effective amount of the compound as defined in either of the first or second embodiments of the invention or administering a therapeutically effective amount of the pharmaceutical composition as defined in the fourth embodiment of the invention.

According to a seventh embodiment of the invention, there is provided the compound as defined in either of the first or second embodiments of the invention, or the pharmaceutical composition as defined in the fourth embodiment, when used in the treatment and/or prophylaxis of disease in a vertebrate in need of said treatment and/or prophylaxis.

According to an eighth embodiment of the invention, there is provided use of the compound as defined in either of the first or second embodiments of the invention, in the preparation of a medicament for the treatment and/or prophylaxis of disease in a vertebrate in need of said lo treatment and/or prophylaxis.

Typically, in the sixth, seventh, or eighth embodiments of the invention, salts of the compounds of the present invention will be pharmaceutically acceptable salts; although other salts may be used in the preparation of the compound of the present invention or of the pharmaceutically acceptable salt thereof.

Typically, for the purposes of any one of the sixth, seventh, or eighth embodiments of the invention, the disease is a cellular proliferative disease.

More typically, the disease is selected from the group consisting of angiogenesis-dependent diseases, inflammatory disorders and/or auto-immune diseases, vascular diseases and thrombosis, viral infection, and cancer.

Typically, for the purposes of any one of the sixth, seventh, or eighth embodiments of the invention, one skilled in the art would be able, by routine experimentation, to determine what an effective, non-toxic amount of the compound of the present invention would be for the purpose of treating a particular disease.

Definitions

In the context of this specification, the term "comprising" means "including principally, but not necessarily solely". Furthermore, variations of the word "comprising", such as "comprise" and "comprises", have correspondingly varied meanings.

In the context of this specification, the term "arsenoxide" refers to the group —As═O.

In the context of this specification, the groups written —As═O and —As(OH)$_2$ are to be considered synonymous.

In the context of this specification, the term "arsenoxide equivalent" refers to any dithiol reactive species that shows essentially the same affinity towards dithiols as —As═O or As(OH)$_2$, and the term includes, for example, groups comprising a transition element, and any trivalent arsenical that is either hydrolysed to —As═O or —As(OH)$_2$ when dissolved in an aqueous medium (such as cell culture buffers and the fluids contained in the organism being treated).

The term "arsenical" as used herein, includes any compound that contains arsenic.

The term "acyl" as used herein, includes monovalent and divalent alkyl, alkenyl, alkynyl, cycloalkyl and cycloalkenyl moieties possessing a terminal carbonyl substituent wherein attachment may occur at the hydrocarbon moiety, the carbonyl moiety or both.

The term "alkyl" as used herein, includes within its meaning monovalent, saturated, straight and branched chain hydrocarbon radicals.

The term "alkenyl" as used herein, includes within its meaning, monovalent, straight and branched chain hydrocarbon radicals having at least one double bond.

The term "alkynyl" as used herein, includes within its meaning, monovalent, straight and branched chain hydrocarbon radicals having at least one triple bond.

The term "alkylene" as used herein, includes within its meaning divalent, saturated, straight chain hydrocarbon radicals.

The term "alkenylene" as used herein, includes within its meaning, divalent, straight chain hydrocarbon radicals having at least one double bond.

The term "alkynylene" as used herein, includes within its meaning, divalent, straight chain hydrocarbon radicals having at least one triple bond.

The term "aryl" as used herein, includes within its meaning monovalent, single, polynuclear, conjugated and fused aromatic hydrocarbon radicals.

The term "arylene" as used herein, includes within its meaning divalent, single, polynuclear, conjugated and fused aromatic hydrocarbon radicals.

The term "closely spaced dithiol" as used herein, includes within its meaning thiols that are chemically vicinal, as well as thiols brought into spacial apposition by virtue of molecular conformation.

The term "cycloalkyl" as used herein, includes within its meaning monovalent, saturated, monocyclic, bicyclic, polycyclic or fused polycyclic hydrocarbon radicals.

The term "cycloalkylene" as used herein, includes within its meaning divalent, saturated, monocyclic, bicyclic, polycyclic or fused polycyclic hydrocarbon radicals.

The term "cycloalkenyl" as used herein, includes within its meaning monovalent, saturated, monocyclic, bicyclic, polycyclic or fused polycyclic hydrocarbon radicals having at least one double bond.

The term "cycloalkenylene" as used herein, includes within its meaning divalent, saturated, monocyclic, bicyclic, polycyclic or fused polycyclic hydrocarbon radicals having at least one double bond.

The term "halo" as used herein, includes fluoro, chloro, bromo and iodo.

The term "heteroaryl" as used herein, includes within its meaning monovalent, single, polynuclear, conjugated and fused aromatic radicals having 1 to 12 atoms wherein 1 to 6 atoms are heteroatoms selected from O, N and S.

The term "heteroarylene" as used herein, includes within its meaning divalent, single, polynuclear, conjugated and fused aromatic radicals having 1 to 12 atoms wherein 1 to 6 atoms are heteroatoms selected from O, N and S.

The term "heterocycloalkyl" as used herein, includes within its meaning-monovalent, saturated, monocyclic, bicyclic, polycyclic or fused radicals wherein 1 to 5 atoms are heteroatoms selected from O, N or S.

The term "heterocycloalkylene" as used herein, includes within its meaning divalent, saturated, monocyclic, bicyclic, polycyclic or fused polycyclic radicals wherein 1 to 5 atoms are heteroatoms selected from O, N or S.

The term "heterocycloalkenyl" as used herein, includes within its meaning monovalent, saturated, monocyclic, bicyclic, polycyclic or fused polycyclic radicals having at least 1 double bond and wherein 1 to 5 atoms are heteroatoms selected from O, N or S.

The term "heterocycloalkenylene" as used herein, includes within its meaning divalent, saturated, monocyclic, bicyclic, polycyclic or fused polycyclic radicals having at least one double bond and wherein 1 to 5 atoms are heteroatoms selected from O, N or Se.

The term "phenylarsonic acid" as used herein, is to be considered synonymous with "benzene sulfonic acid".

The term "therapeutically effective amount" as used herein, includes within its meaning a non-toxic but sufficient amount of a compound or composition of the invention to provide the desired therapeutic effect. The exact amount required will vary from subject to subject depending on factors such as the species being treated, the age and general condition of the subject, the severity of the condition being treated, the particular agent being administered and the mode of administration and so forth. Thus, it is not possible to specify an exact "effective amount". However, for any given case, an appropriate "effective amount" may be determined by one of ordinary skill in the art using only routine experimentation.

The term "transition element" as used herein, includes within its meaning the groups of elements comprising the transition metals, the lanthanides and the actinides.

Abbreviations pAA, p-arsanilic acid, 4-aminobenzenearsonic acid; AspAO, N-(3-(4-arsenosophenylcarbamoyimelhylthio)propanoyl)-L-aspartic acid; BAE, bovine aortic endothelial; BCE, bovine capillary endothelial; BCS, bovine calf serum; BSA, bovine serum albumin; BRAA, 4-(N-(bromoacetyl)amino)phenylarsonic acid; BRAO, 4-(N-(bromoacetyl)amino)-phenylarsenoxide; BVS, bovine vascular smooth muscle; CAM, chick chodoallantoic membrane; Cys*AO, N-(3-(4-arsenosophenylcarbamoyimethylthio)propanoyl)-L-glusteic acid; DMEM, Dulbecco's Modified Eagle's Medium; DMP, 2,3-dimercaptopropanol; DMSO, dimethylsulfoxide; DTNB, 5,5'-dithiobis(2-nitrobenzoic acid); DTT, dithiothreitol; EDTA, ethylenediaminetetraacetic acid; FCS, fetal calf serum; FGF, fibroblast growth factor; GSAOF, 4-(N-(S-(N-(3-(fluorescein-5-carbamoylmethylthio)propanoyl)glutathionyl)aceyl)amino)phenylarsenoxide; FXAO, a mixture of 4-(N-(6-(fluorescein-5-carboxamido)hexanoyl)amino)phenylarsenoxide and 4-(N-(6-(fluorescein-6-carboxamido)hexanoyl)amino)phenylarsenoxide; GlcAO, N-(3-(4-arsenosophenylcarbamoylmethylthio)propanoyl)-D-glucosamine; GluA), N-(3-(4-arsenosophenylcarbamoylmethylthio)propanoyl)-L-glutamic acid; GSAA, 4-(N-(S-glutathionylacetyl)amino)phenylarsonic acid; GSAO, 4-(N-(S-glutathionylacetyl)amino)phenylarsenoxide; GSAO-B, 4-(N-(S-(N-(6-(N (6-(N-(biotinoyl)amino)hexanoyl)amino)hexanoyl)glutathionyl)acetylamino)phenylarsenoxide; GSH, reduced glutathione; HDMVEC, human dermal microvascular endothelial cell; HEPES, N-(2-hydroxyethyl)piperazine-N'-(2-ethanesulfonic acid); HIV, human immunodeficiency virus; HRP, horse-radish peroxidase; HUVEC, human umbilical vein endothelial cell; Ig, immunoglobulin; MPB, 3-(N-maleimidylpropionyl)biocylin; PAO, phenylarsenoxide, pAPAO, 4-aminophenylarsenoxide; PBMC, peripheral blood mononuclear cells; PBS, phosphate buffered saline; PDI, protein disulfide isomerase; PVDFt polyvinyidiethylene fluoride; SCID, severe combined immunodeficient; SDS-PAGE, SDS-polyacrylamide gel electrophoresis; SSB, sulfosuccinimidobiotin; TCR, T cell receptor; TNB, 5-thio-2-nitrobenzoate dianion; VEGF, vascular endothelial cell growth factor.

BEST MODE OF PERFORMING THE INVENTION

1. Trivalent Organoarsenical Derivatives

Figure 1:
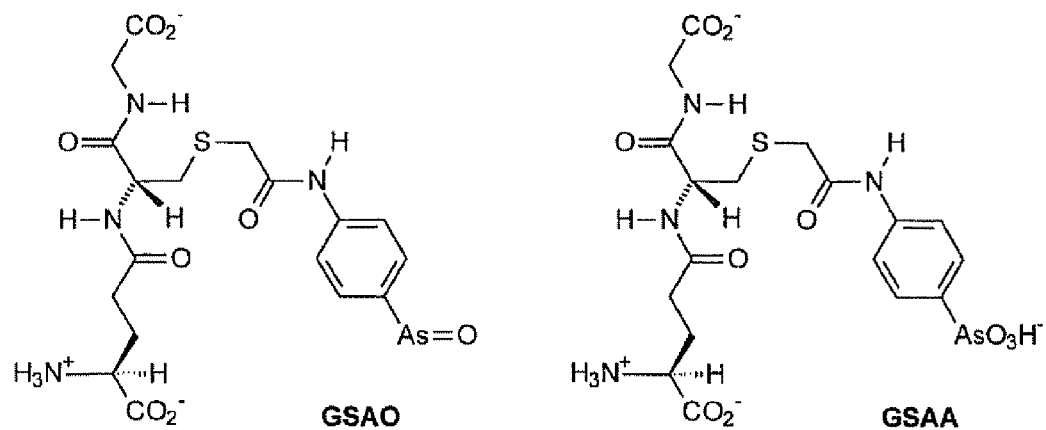
FIG. 1. Structure of GSAO and GSM.

The present invention provides compounds wherein an arsenoxide or arsenoxide equivalent moiety is linked to at least one substantially cell membrane impermeable pendant group, the pendant group being substantially cell membrane-impermeable by virtue of being charged at physiological pH or being hydrophilic in nature. Further, the present invention provides compounds in which a pendant group is linked, with or without the incorporation of a spacer group, to at least one arsenoxide or arsenoxide equivalent.

In a preferred form, the compound of the present invention is a dithiol reactive compound, such as a compound which contains a trivalent arsenical as outlined above. Redox active proteins are often characterised by one or more pairs of closely spaced dithiois which undergo cycles of oxidation and reduction. Trivalent arsenicals have high affinity for closely spaced dithiols, forming dithioarsine derivatives (Adams et al., 1990). Monothiols react very poorly with trivalent arsenicals because two monothiols are required to form the dithioarsine derivative. The process is entropically disfavoured and the binding of the second monothiol is usually sterically restricted.

As a specific example of a substantially cell membrane impermeable group which constitutes a suitable pendant group for the purposes of the present invention, glutathione is a tripeptide that is constitutively secreted by mammalian cells but is not taken up by these cells. In a preferred embodiment, the present invention capitalises on this substantially cell-membrane impermeability feature of glutathione to use glutathione as an essentially inert carrier of an arsenoxide group having the ability to bind to closely spaced dithiols of redox active proteins. In this manner, glutathione is used in the present invention to deliver the arsenoxide group to the mammalian cell surface, but to substantially inhibit passive entry of said moiety into cells.

The compounds of general formulae (I-VI) and those in which the arsenoxide group (As=O) is replaced by an arsenoxide equivalent, may be prepared by methods known generally in the art. Suitable methods for the synthesis of compounds of formulae (I-VI) and intermediates thereof are described, for example, in Houben-Weyl, *Methoden der Organischen Chemie*; J. March, *Advanced Organic Chemistry*, 4$^{th}$ Edition (John Wiley & Sons, New York, 1992); D. C. Liotta and M. Volmer, eds, *Organic Syntheses Reaction Guide* (John Ariley & Sons, Inc., New York, 1991); R. C. Larock, *Comprehensive Organic Transformations* (VCH, New York, 1989), H. O. House, *Modern Synthetic Reactions* 2$^{nd}$ Edition (W. A. Benjamin, Inc., Menlo Park, 1972); N. S. Simpkins, ed., 100 *Modern Reagents* (The Royal Society of Chemistry, London, 1989); A. H. Hains *Methods for the Oxidation of Organic Compounds* (Academic Press, London, 1988) and B. J. Wakefield *Organoltithium Methods* (Academic Press, London, 1988).

Example reaction schemes to illustrate the generic formation of linkers of the compounds of the present invention are shown in the following schemes.

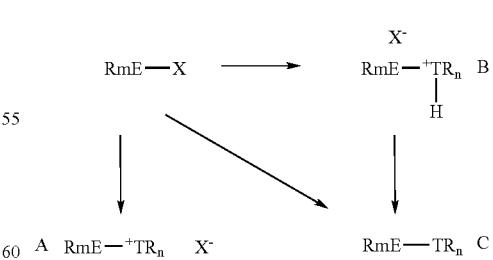

wherein E represents an electrophilic site; and m, n are integers greater than or equal to 0.

The scheme below shows a starting molecule $RCH_2X$, where R represents the rest of the molecule to which the —$CH_2X$ group is attached. X represents a leaving group, for example, a halogen or $RSO_3$—, which is displaced by the nucleophile $TR_n$. Nucleophiles attack at electrophilic sites, resulting in the formation of a new covalent bond between the nucleophilic and electrophilic species. In the scheme below, the methylene carbon atom is the electrophilic site, and the overall reaction can be described as one of nucleophilic substitution.

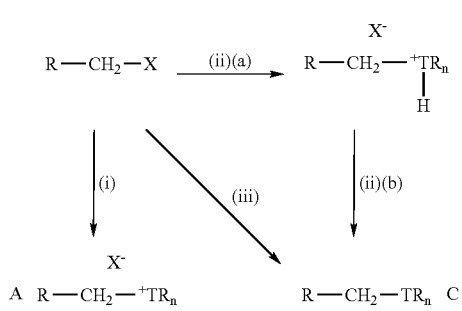

There are three simple variations on the above scheme, as illustrated by reactions (i) to (iii): in this reaction, the attacking nucleophile is represented by the uncharged molecule $TR_n$, which displaces the leaving group X, giving the product A which has a positive charge formally localised on T.

the first step (a) of this reaction involves the attacking nucleophile $HTR_n$ displacing the leaving group X, giving the ionic product B initially, followed by loss of H+ in step (b) to give the uncharged product C.

in this reaction, product C is formed directly by use of $TR_n^-$ as the nucleophile.

In all three reactions (i) to (iii), X is lost as X—, and atom T must have a lone pair of electrons. Shown below are general examples of each of the reactions (i) to (iii). Note that reaction (iii) is analogous to the formation of GSAO from BRAO and GSH.

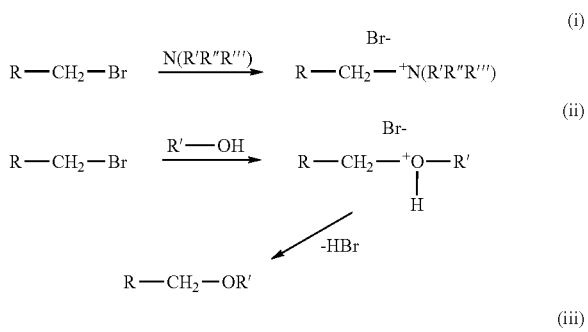

Alternatively, the reaction may be between a nucleophile and, for example, an α,β-unsaturated ketone (when Z=O) (or aldehyde when Z=O and $R_1$=H) as illustrated in the following schemes. For example, where the nucleophile is $TR_n$:

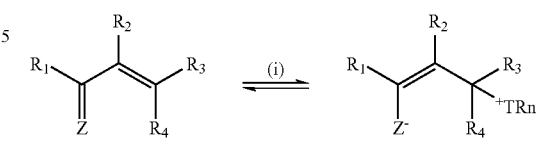

where the nucleophile is $HTR_n$

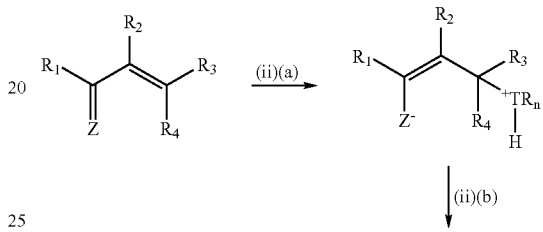

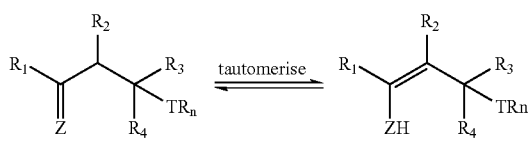

where the nucleophile is $TR_n$—.

wherein Z is selected from the group consisting of O, S, NR, or +N(R)(R').

A typical example of a general synthetic route for preparing hydrophilic amine compounds of the invention is represented in the following scheme, wherein the reagent in step 5 has been exemplified as BRAO:

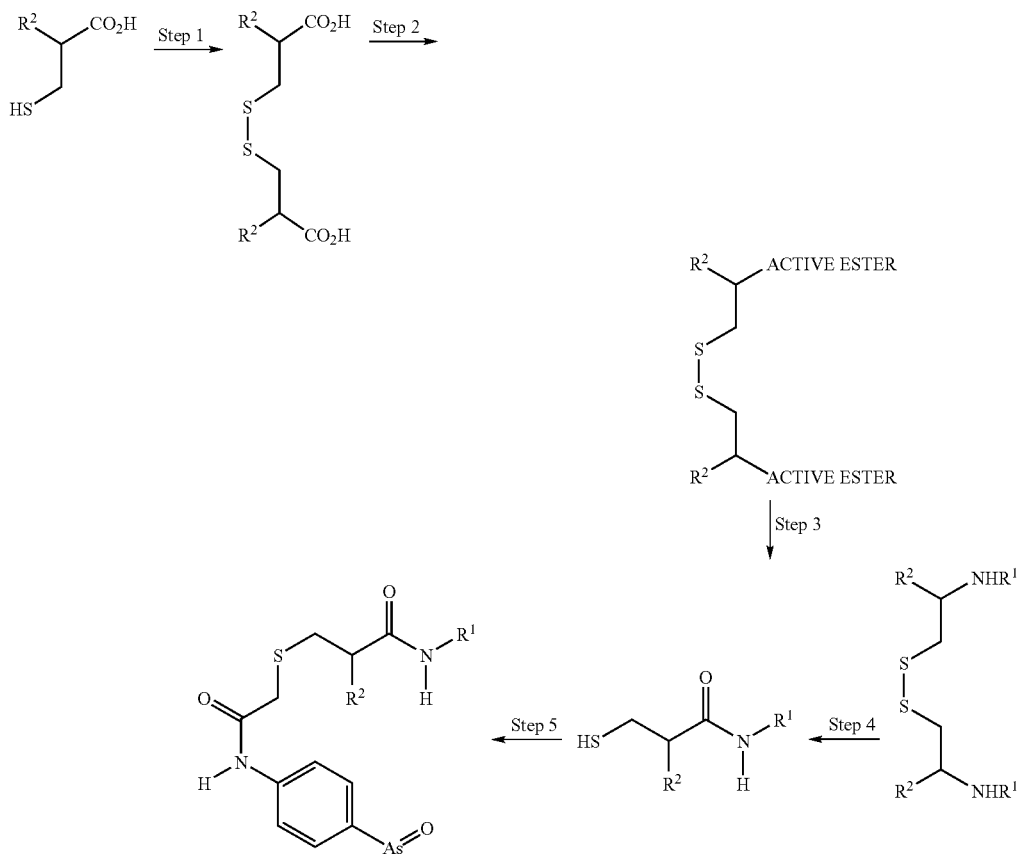

Still more typically, hydrophilic amine compounds of the invention can be prepared according to the general scheme outlined below which has been exemplified using BRAO in the final step and wherein X is a halogen or other suitable leaving group.

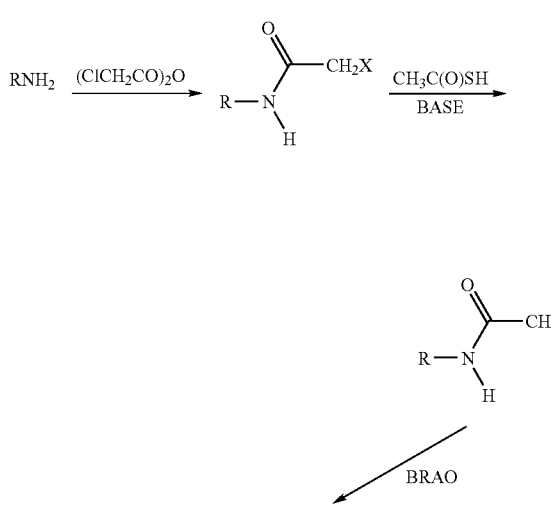

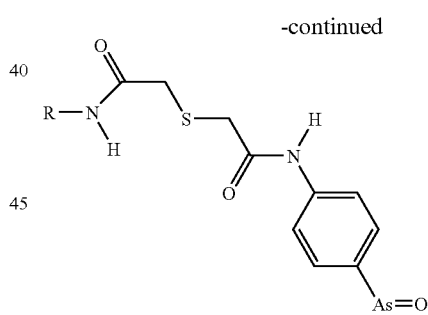

-continued

In respect of the above schemes, one skilled in the art would recognise that the various reagents and reactants can be routinely modified in order to synthesise any given compound of the invention. The compounds of the present invention can be lyophilised for storage and reconstituted prior to use.

In a typical synthesis of a preferred compound of the invention, glutathione may be reacted with BRAC under conditions favourable to the formation of a covalent bond between the free thiol of glutathione and the chemical entity to which the arsenoxide is attached. Reactions involving nucleophilic attack by the glutathione thiol will, in general, require alkaline conditions. Electrophilic attack of some reactive species on the glutathione sulfur atom may be carried out; in general this would likely require acidic conditions. The structure of GSAO and the corresponding arsonic acid compound GSM are shown in FIG. 1.

Typically, the compounds of the invention are inhibitors of redox active proteins by virtue of an ability to bind dithiols. Redox active proteins may contain two closely spaced thiols which can reversibly form a disulfide bond. The proposed mode by which the compounds of the invention inhibit these proteins is by the arsenoxide or arsenoxide equivalent binding to the reduced (dithiol) form of the protein. Such binding may be essentially irreversible or essentially reversible under physiological conditions. If the binding is essentially irreversible under physiological conditions, the protein is permanently inhibited from redox-cycling between the dithiol and disulfide states (ie. it is irreversibly inactivated, or inhibited).

Figure 2:
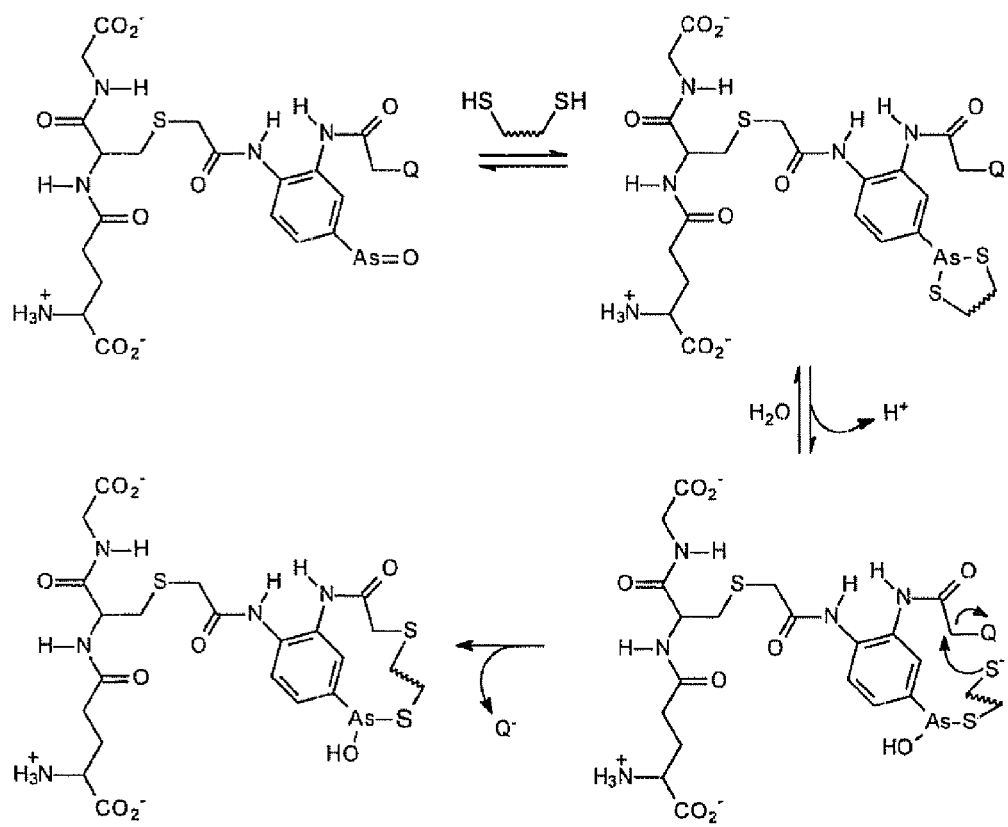
FIG. 2. Schematic representation of the irreversible inhibition of a redox active protein by initial binding of an arsenoxide group with a dithiol of the protein, followed by alkylation of the active site of the protein.

Alternatively, if the binding of the arsenoxide or arsenoxide equivalent to the protein dithiol is essentially reversible under physiological conditions, inhibition will not be permanent. Accordingly, compounds of the present invention may include having a substituent which can act as an alkylating agent, attached to the $(XBX')_nB'$ linker or the substantially cell membrane impermeable group, A. The alkylating group may be brought into the vicinity of one of the active site dithiols of the protein by the reaction of the arsenical group with the dithiol of the protein. The alkylating group may then react with the dithioarsine-protein intermediate, thereby permanently inhibiting the protein and preventing redox-cycling. An example of this mode of irreversible inhibition resulting from alkylation is represented in FIG. 2. Compounds having an alkylating agent attached to the $(XBX')_nB'$ linker or the substantially cell-membrane impermeable group, Ar are exemplified by the structural formulae (VII) and (VIII) below, wherein the pendant group A is glutathione:

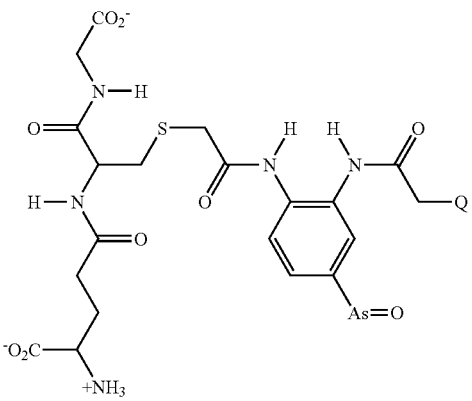

(VIII)

wherein Q is a leaving group.

Suitable modifications will be apparent to those of skill in this art. A person skilled in this would recognise that the invention also provides for the compounds of the invention in any state of ionisation, for example acid salt, zwitterionic uncharged, zwitterionic anion, dianion.

The present invention also provides for further compounds of the invention which are modified through the glutamyl α-amino nitrogen of glutathione, for example, with a detectable group, such as biotin, a fluorophore, or a group comprising a transition element. For example, the invention provides for GSAO-B, a biotin-linked derivative of GSAO, according to the following formula (IX):

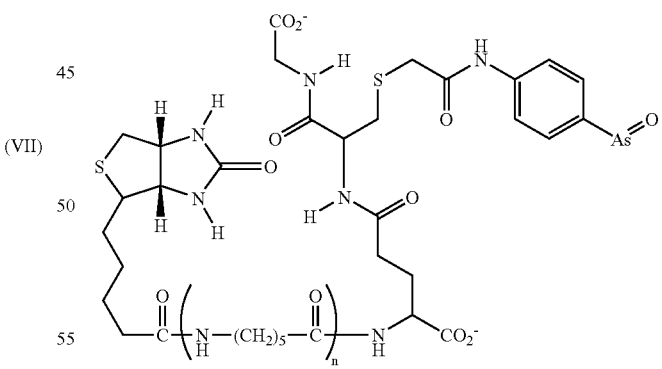

(IX)

wherein n=1 or 2.

Figure 6:
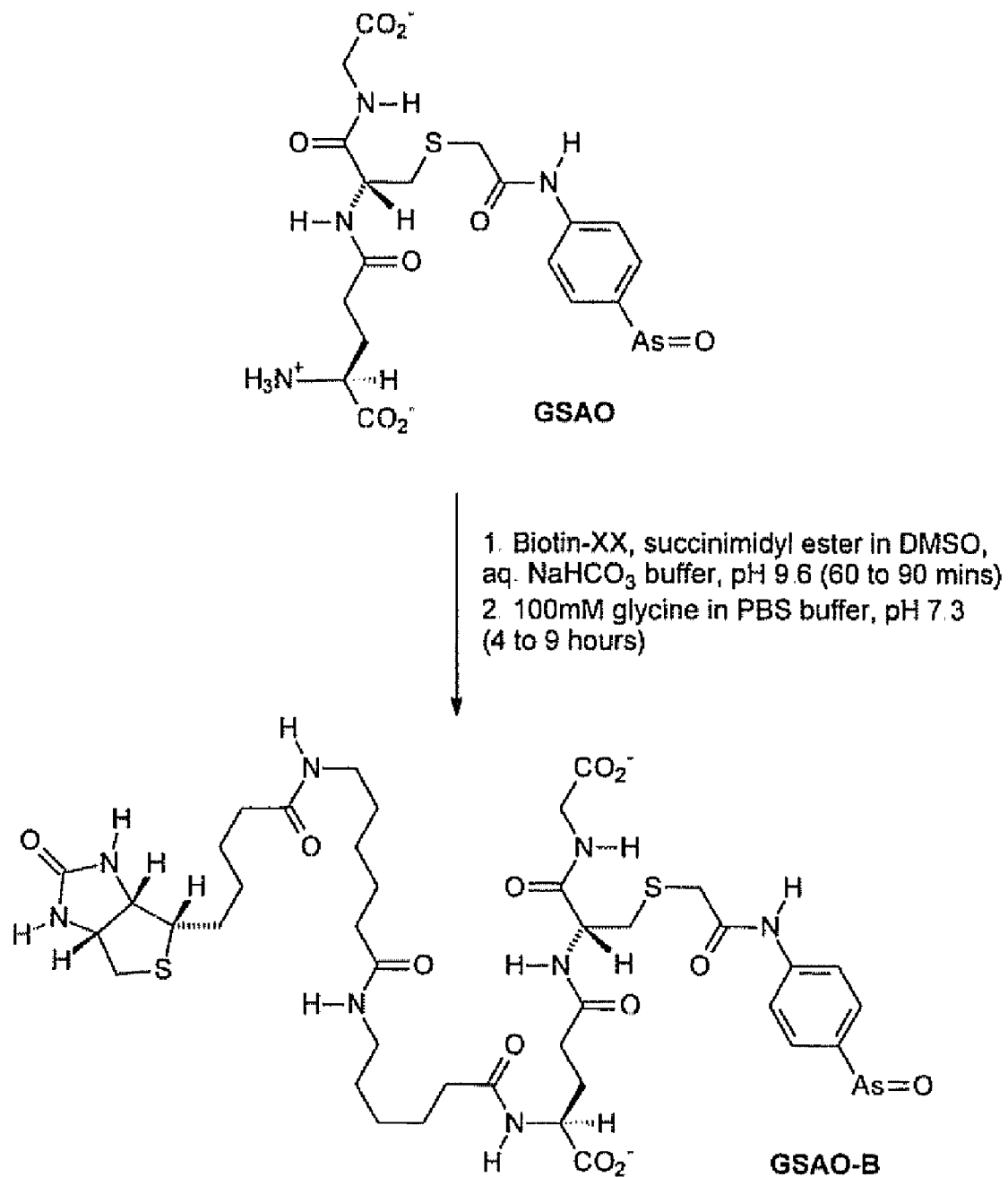
FIG. 6. Schematic representation of the synthesis of GSAO-B

A method of synthesis of GSAO-B is provided in Example 1(c) and illustrated in FIG. 6. An alternative preferred compound of the invention in which a desired modifying group may be attached through the glutamyl α-amino nitrogen of glutathione is represented in the following formula (X):

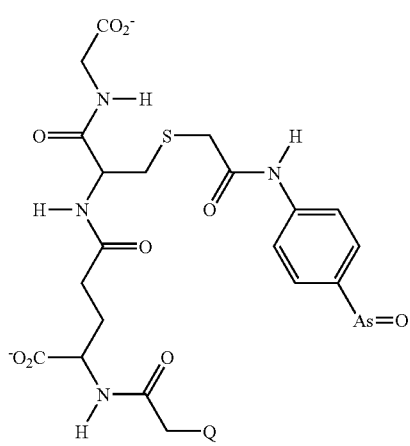

(VII)

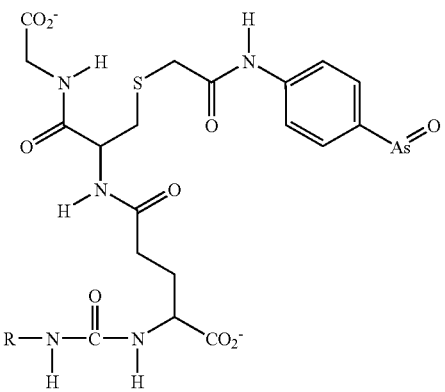

(X)

wherein R is any desired modifying group.

Typically, R may be selected from the group consisting of hydrogen, halogen, hydroxy, amino, nitro, carboxy, alkoxy, alkyl and aryl.

1.1 Stability of the Trivalent Arsenicals Towards Oxidation

Arsenoxides (R—As═O) have been shown not to possess an arsenic-oxygen double bond as is usually written, but are likely to exist either as cyclic polymers (containing As—O—As linkages) or, more likely, as the hydrate R—As(OH)$_2$, an organoarsonous acid, in aqueous solution (Doak and Freedman, 1970; Knoch et al, 1995). Solutions of organoarsenicals such as GSAO and BRAO are deactivated over time by oxidation. This oxidation can be slowed in three ways; removal of dissolved O$_2$ from solutions containing the arsenoxides, lowering the pH of these solutions, or by addition of glycine to the solutions. Glycine is routinely used to prevent oxidation of the stock solutions of the trivalent organoarsenicals. Similar to the reaction between 2,3-dimercaptopropanol and R—As(OH)$_2$ in which a 5-membered dithioarsonite (XI) is formed, reaction of glycine with R—As(OH)$_2$ is thought to give a 5-membered cyclic 1,3,2-oxazarsolidin-5-one (XII).

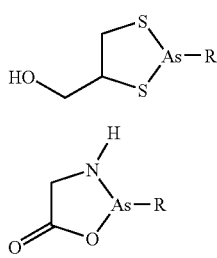

(XI)

(XII)

2. Treatment and/or Prevention of Disease

The compounds of the invention are useful in the treatment of various disorders and diseases of vertebrates. Typically, the compounds of the first or second embodiments of the invention, or the pharmaceutical formulation of the fourth embodiment of the invention, are useful in the treatment of various disorders and diseases of vertebrates. Also provided by the present invention therefore are methods of treatment of various diseases and disorders of vertebrates.

Typically, the vertebrate is selected from the group consisting of human, non-human primate, murine, bovine, ovine, equine, caprine, leporine, avian, feline and canine. More typically, the vertebrate is human, non-human primate or murine. Even more typically, the vertebrate is human.

Thus, the compounds of the invention may be useful for the treatment of disorders which may be grouped into broad categories such as the following: angiogenesis-dependent diseases, cellular proliferative diseases, inflammatory disorders, auto-immune diseases, blood vessel diseases, thrombosis, viral infection, and cancer.

2.1. Treatment and/or Prevention of Angiopenesis-Dependent Disorders

More typically, the compounds of the invention may be useful for the treatment of angiogenesis-dependent diseases, such as cancer, hemangioma, arteriovenous malformations, arthritis, Osler-Weber Syndrome, complicated atherosclerotic plaques, psoriasis, corneal graft neovascularization, pyrogenic granuloma, delayed wound healing, retrolental fibroplasia, diabetic retinopathy, scleroderma, granulations, angiofibroma, neovascular glaucoma, trachoma, hemophilic joints, hypertrophic scars, or gastric ulcers.

Typically, the cancer is selected from the group consisting of carcinogenic tumours, tumours of epithelial origin, such as colo-rectal cancer, breast cancer, lung cancer, head and neck tumours, hepatic cancer, pancreatic cancer, ovarian cancer, gastric cancer, brain cancer, bladder cancer, prostate cancer and urinary/genital tract cancer; mesenchymal tumours, such as sarcoma; and haemopoietic tumours such as B cell lymphoma.

Typically, the cancer is a haematological tumour. More typically, the cancer is a solid tumour.

As way of background, blood vessels develop by two processes, vasculogenesis and angiogenesis (Risau, 1997). Vasculogenesis occurs during embryogenesis, and is the process whereby endothelial cells are born from progenitor cell types. The sprouting of new capillaries from existing vessels is termed angiogenesis, and occurs during embryogenesis and in the adult.

Angiogenesis is also a critical component of tumour metastasis. Tumour blood vessels are immature and highly permeable having little basement membrane and fewer intercellular junctional complexes compared to normal mature vessels. These new blood vessels provide an efficient route of exit for tumour cells to leave the primary site and enter the blood stream. The number of metastases formed is generally proportional to the number of tumour cells shed. Therefore, a decrease in angiogenesis in a tumour should decrease the number of tumour cells shed into the circulation and the number of metastases that arise downstream.

The process of tumour angiogenesis is complex. In response to an appropriate stimulus, the basement membrane surrounding an endothelial cell tube is locally degraded, which triggers the endothelial cells underlying this disrupted matrix to change shape and invade the surrounding tumour stroma. The invading endothelial cells proliferate and develop into a migrating column. The cells of the column wall stop proliferating, change shape, and adhere to each other to form the lumen of the new capillary. Ultimately, the new capillaries fuse and form into loops, resulting in a circulatory system that facilitates exchange of nutrients and waste products in the region.

The induction of tumour angiogenesis is mediated by several angiogenic molecules released by both tumour cells and host cells (Hanahan and Folkman, 1996). A number of proteins are known to stimulate endothelial cell growth and movement, including epidermal growth factor, angiogenin, estrogen, the fibroblasts growth factors (FGFs), and vascular endothelial growth factor (VEGF). Anti-angiogenic factors include interferon, thrombospondin, platelet factor 4, tissue inhibitors of metalloproteinase-1 and -2, interleukin 12, angiostatin and endostatin.

Figure 16:
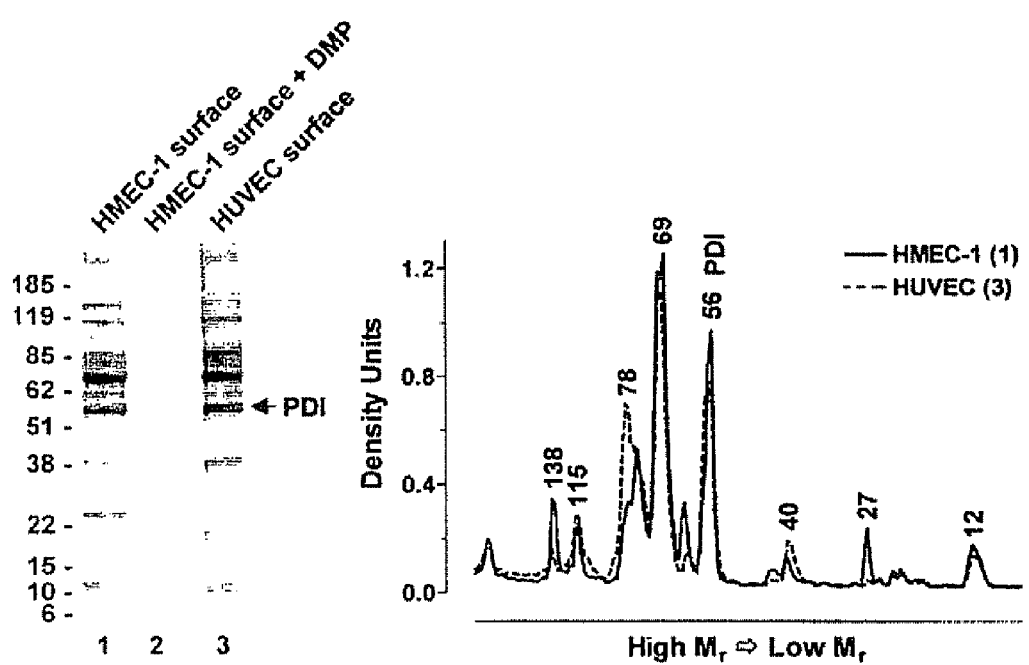
FIG. 16. Identification of endothelial cell surface proteins that contain closely spaced dithiols). A The surface of HMEC-1 or HUVE cells (2×10$^6$ cells in 0.4 mL) was labelled with GSAO-B (100 µM) for 30 minutes at room temperature in the absence (lanes 1 and 3) or presence of DMP (400 µM) (lane 2). The endothelial cells were lysed and the lysate from both incubations was resolved on 4-15% SDS-PAGE, transferred to PVDF membrane, and blotted with streptavidin peroxidase to detect the GSAO-B label. The results represent labelling of 3×10$^4$ HMEC-1 (lanes 1 and 2) of HUVE cells (lane 3). The positions of M$_r$ markers are shown at left. B Densitometry profile of the surface labelled proteins (lanes 1 and 3). The apparent M$_r$'s of the individual proteins are indicated.

There are ten distinct proteins on the endothelial cell surface with molecular masses of between 12 and 138 kDa that bind GSAO, and this is as exemplified in Example 3(a) and FIG. 16. This finding suggests that the erdothelial cell surface supports redox events in certain proteins. Perturbation of these events has consequences for endothelial cell biology, such as effects on proliferation of endothelial cells, as outlined in general in Example 3. More specifically, examples 3(c) and 3(d) and FIGS. 18-21 indicate that GSAO was a selective inhibitor of proliferation and tube formation of endothelial cells in culture. GSAO also inhibited new blood vessel formation in the chick chorioallantoic membrane, (Example 3(o) and FIG. 22), and was a potent inhibitor of tumour angiogenesis and tumour growth in mice, as outlined in Examples 3(f) to 3(i) and FIGS. 23-28.

2.2 Treatment and/or Prevention of Viral Infection

The compounds of the invention may also find use in the treatment or prevention of human retroviral infections (family retroviridae) including, for example, oncoviral infection such as HTLV-I; Lentiviral infection including HIV-1 and HIV-2; or for the treatment or prevention of Sindbis virus infection.

CD4 is an integral membrane glycoprotein and a member of the immunoglobulin (Ig) superfamily of receptors which mediates cell-cell interactions in the immune system CD4 is expressed on most thymocytes and on the subset of peripheral T lymphocytes that includes helper T cells (Fleury et al., 1991). CD4 is required to shape the T-cell repertoire during thymic development and to permit appropriate activation of mature T cells and B cells. The T cell receptor (TCR) of CD4+ T cells recognises antigens presented by class II MHC molecules. CD4 binds to class II MHC to enhance the T cell response, either as an adhesion molecule (co-ligand) or in a ternary complex with the TCR as a part of the antigen recognition process (co-receptor).

Another ligand for CD4 is HIV-1. HIV-1 enters CD4+ cells by fusing the lipid membrane of is the virus particle with the cell membrane to allow the virion core access to the cytoplasm. HIV-1 fusion is triggered by the interaction of the HIV-1 envelope glycoprotein, gp120, with CD4. Chemokine co-receptors are also required for HIV-1 entry (Littman, 1998) HIV-1 compromises the immune system by impairing the CD4+ T helper cell response.

Evidence that CD4 contains one or more redox active thiols was provided by Nakashima et al. (1994). They observed that $HgCl_2$, a compound that can catalyse formation of disulfide linkages between free thiols, aggregated CD4 on the T cell surface. This result suggested that $HgCl_2$ was cross-linking CD4 through free thiol(s) in CD4.

As outlined in Example 4 (in particular, Example 4(d)), and FIGS. 30-35, GSAO binds to cell surface CD4 and acts as an effective inhibitor of infection of CD4+ cells by HIV.

2.3 Treatment and/or Prevention of Other Disorders

The compounds of the invention, or pharmaceutical formulations thereof, may also be used in the prevention and/or treatment of inflammatory disorders and/or auto-immune diseases, examples of which include the following: rheumatoid arthritis, seronegative arthritides and other inflammatory arthritides, systemic lupus erythematosus, polyarteritis and related syndromes, systemic sclerosis, Sjögren's syndrome and other inflammatory eye disease, mixed connective tissue disease, polymyositis and dermatomyositis, polymyalgia rheumatica and giant cell arteritis, inflammatory joint disease, non-inflammatory arthropathies and soft tissue rheumatism, algodystrophy.

Examples of vascular disease and thrombosis for which the inventive compound may be used in a preventive manner or in the treatment oft include the following: progression of atherosclerosis; cerebrovascular accidents such as transient ischaemic, completed stroke, and after carotid surgery; acute myocardial infarction (primary and secondary); angina; occlusion of coronary artery bypass graft; occlusion following percutaneous transluminal coronary angioplasty; occlusion following coronary stenting; vascular occlusion in peripheral arterial disease; venous thromboembolic disease following surgery, or during pregnancy, or during immobilisation.

Examples of small vessel disease for which the inventive compound may be used in prevention or treatment oft include the following: glomerulonephritis; thrombotic thrombocytopenic purpura; the haemolytic uraemic syndrome; placental insufficiency and preeciampsia.

The compounds of the invention may also be used for the prevention or treatment of vascular syndromes and myeloproliferative diseases.

The compounds of the invention may also find use in the prevention of thrombosis formation in the following situations: artificial/prosthetic vascular shunts and grafts; prosthetic heart valves; cardiopulmonary bypass procedures; haemoperusion and haemodialysis.

2.4 Pharmaceutical and/or Therapeutic Formulations

Typically, for medical use, salts of the compounds of the present invention will be pharmaceutically acceptable salts; although other salts may be used in the preparation of the inventive compound or of the pharmaceutically acceptable salt thereof. By pharmaceutically acceptable salt it is meant those salts which, within the scope of sound medical judgement, are suitable for use in contact with the tissues of humans and lower animals without undue toxicity, irritation, allergic response and the like, and are commensurate with a reasonable benefit/risk ratio. Pharmaceutically acceptable salts are well known in the art.

For instance, suitable pharmaceutically acceptable salts of the compounds of the present invention may be prepared by mixing a pharmaceutically acceptable acid such as hydrochloric acid, sulfuric acid, methanesulfonic acid, succinic acid, fumaric acid, maleic acid, benzoic acid, phosphoric acid, acetic acid, oxalic acid, carbonic acid, tartaric acid, or citric acid with the compounds of the invention. Suitable pharmaceutically acceptable salts of the compounds of the present invention therefore include acid addition salts.

For example, S. M. Berge et al. describe pharmaceutically acceptable salts in detail in *J. Pharmaceutical Sciences*, 1977, 66:1-19. The salts can be prepared in situ during the final isolation and purification of the compounds of the invention, or separately by reacting the free base function with a suitable organic acid. Representative acid addition salts include acetate, adipate, alginate, ascorbate, asparate, benzenesulfonate, benzoate, bisulfate, borate, butyrate, camphorate, camphorsulfonate, citrate, cyclopentanepropionate, digluconate, dodecylsulfate, ethanesulfonate, fumarate, glucoheptonate, glycerophosphate, hemisulfate, heptonate, hexanoate, hydrobromide, hydrochloride, hydroiodide, 2-hydroxyethanesulfonate, lactobionate, lactate, laurate, lauryl-sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, toluenesulfonate, undecanoate, valerate salts, and the like. Representative alkali or alkaline earth metal salts include sodium, lithium potassium, calcium, magnesium, and the like, as well as nontoxic ammonium, quaternary ammonium, and amine cations, including, but not limited to ammonium, tetramethylammonium, tetraethylammonium, methylamine, dimethylamine, trimethylamine, triethylamine, ethylamine, and the like.

Also included within the scope of the present invention are prodrugs of the inventive compounds. Typically, prodrugs will be functional derivatives of the compounds of the present invention which are readily converted in vivo to the required compounds of the present invention as described herein. Typical procedures for the selection and preparation of prodrugs are known to those of skill in the art and are described, for instance, in H. Bundgaard (Ed), *Design of Prodrugs*, Elsevier, 1985.

Single or multiple administrations of the pharmaceutical compositions can be carried out with dose levels and pattern being selected by the treating physician. Regardless, the pharmaceutical composition of the present invention should provide a quantity of the compound sufficient to effectively treat the patient.

One skilled in the art would be able, by routine experimentation, to determine an effective, non-toxic amount of the compounds of the invention which would be required to treat or prevent the disorders and diseases to which the inventive compound is applicable. Generally, an effective dosage is expected to be in the range of about 0.0001 mg to about 1000 mg per kg body weight per 24 hours; typically, about 0.001 mg to about 750 mg per kg body weight per 24 hours; about 0.01 mg to about 500 mg per kg body weight per 24 hours; about 01 mg to about 500 mg per kg body weight 30 per 24 hours; about 0 1 mg to about 250 mg per kg body weight per 24 hours; about 1.0 mg to about 250 mg per kg body weight per 24 hours. More typically, an effective dose range is expected to be in the range about 1.0 mg to about 200 mg per kg body weight per 24 hours; about 1.0 mg to about 100 mg per kg body weight per 24 hours; about 1.0 mg to about 50 mg per kg body weight per 24 hours; about 10 mg to about 25 mg per kg body weight per 24 hours, about 5.0 mg to about 50 mg per kg body weight per 24 hours; about 5.0 mg to about 20 mg per kg body weight per 24 hours; about 5.0 mg to about 15 mg per kg body weight per 24 hours.

Alternatively, an effective dosage may be up to about 500 mg/m$^2$. Generally, an effective dosage is expected to be in the range of about 25 to about 500 mg/m$^2$, preferably about 25 to about 350 mg/m$^2$, more preferably about 25 to about 300 mg/m$^2$, still more preferably about 25 to about 250 mg/m$^2$, even more preferably about 50 to about 250 mg/m$^2$, and still even more preferably about 75 to about 150 mg/m$^2$.

In relation to GSAO, an effective dosage is expected to be in the range of about 0.0001 mg to about 100 mg GSAO per kg body weight per 24 hours, preferably about 0.001 mg to about 100 mg GSAO per kg body weight per 24 hours, more preferably about 0.01 mg to about 50 mg GSAO per kg body weight per 24 hours, even more preferably about 0.1 mg to about 20 mg GSAO per kg body weight per 24 hours, even more preferably still about 0.1 mg to about 10 mg GSAO per kg body weight per 24 hours. Typically the treatment would be for the duration of the condition.

Further, it will be apparent to one of ordinary skill in the art that the optimal quantity and spacing of individual dosages of a compound of the present invention will be determined by the nature and extent of the condition being treated, the form, route and site of administration, and the nature of the particular vertebrate being treated. Also, such optimum conditions can be determined by conventional techniques.

It will also be apparent to one of ordinary skill in the art that the optimal course of treatment, such as, the number of doses of the compound of the present invention given per day for a defined number of days, can be ascertained by those skilled in the art using conventional course of treatment determination tests.

When used in the treatment of disease the compounds of the present invention may be administered alone. However, it is generally preferable that the compound be administered as a pharmaceutical formulation. In general pharmaceutical formulations of the present invention may be prepared according to methods which are known to those of ordinary skill in the art and accordingly may include a pharmaceutically acceptable carrier, diluent and/or adjuvant.

The carriers, diluents and adjuvants must be "acceptable" in terms of being compatible with the other ingredients of the formulation, and not deleterious to the recipient thereof.

Examples of pharmaceutically and veterinarily acceptable carriers or diluents are demineralised or distilled water; saline solution; vegetable based oils such as peanut oil, safflower oil, olive oil, cottonseed oil, maize oil, sesame oils such as peanut oil, safflower oil, olive oil, cottonseed oil, maize oil, sesame oil, arachis oil or coconut oil; silicone oils, including polysiloxanes, such as methyl polysiloxane, phenyl polysiloxane and methylphenyl polysolpoxane; volatile silicones; mineral oils such as liquid paraffin, soft paraffin or squalane; cellulose derivatives such as methyl cellulose, ethyl cellulose, carboxymethylcellulose, sodium carboxymethylcellulose or hydroxypropylmethylcellulose; lower alkanols, for example ethanol or iso-propanol; lower aralkanols; lower polyalkylene glycols or lower alkylene glycols, for example polyethylene glycol, polypropylene glycol, ethylene glycol, propylene glycol, 1,3-butylene glycol or glycerin; fatty acid esters such as isopropyl paimitate, isopropyl myristate or ethyl oleate; polyvinylpyrridone; agar; carrageenan; gum tragacanth or gum acacia, and petroleum jelly. Typically, the carrier or carriers will form from 10% to 99.9% by weight of the compositions.

In a preferred form the pharmaceutical composition of the invention comprises an effective amount of a compound of the invention, such as GSAO, together with a pharmaceutically acceptable carrier, diluent and/or adjuvant as shown in Example 5.

The pharmaceutical compositions of the invention may be administered by standard routes. In general, the compositions may be administered by the topical, transdermal, intraperitoneal, intracranial, intracerebroventricular, intracerebral, intravaginal, intrauterine, oral, rectal or parenteral (e.g., intravenous, intraspinal, subcutaneous or intramuscular) route. Still generally, the compositions of the invention may be in the form of a capsule suitable for oral ingestion, in the form of an ointment, cream or lotion suitable for topical administration, in a form suitable for delivery as an eye drop, in an aerosol form suitable for administration by inhalation, such as by intranasal inhalation or oral inhalation.

The pharmaceutical compositions of the invention may also be administered in the form of liposomes. Liposomes are generally derived from phospholipids or other lipid substances, and are formed by mono- or multi-lamellar hydrated liquid crystals that are dispersed in an aqueous medium. Any non-toxic, physiologically acceptable and metabolisable lipid capable of forming liposomes can be used. The formulations of the present invention in liposome form may contain, in addition to a compound of the present invention, stabilisers, preservatives, excipients and the like. The preferred lipids are the phospholipids and the phosphatidylcholines (lecithins), both natural and synthetic. Methods to form liposomes are known in the art, and in relation to this specific reference is made to: Prescott, Ed., Methods in Cell Biology, Volume XIV, Academic Press, New York, N.Y. (1976), p. 33 et seq., the contents of which is incorporated herein by reference.

For administration as an injectable solution or suspension, non-toxic parenterally acceptable diluents or carriers can include, Ringer's solution, isotonic saline, phosphate buffered saline, ethanol and 1,2-propylene glycol.

Some examples of suitable carriers, diluents, excipients and adjuvants for oral use include peanut oil, liquid paraffin, sodium carboxymethylcellulose, methylcellulose, sodium alginate, gum acacia, gum tragacanth, dextrose, sucrose, sorbitol, mannitol, gelatine and lecithin. In addition these oral formulations may contain suitable flavouring and colourings agents. When used in capsule form the capsules may be coated with compounds such as glyceryl monostearate or glyceryl distearate which delay disintegration of the capsule.

Adjuvants typically include emollients, emulsifiers, thickening agents, preservatives, bactericides and buffering agents.

Solid forms for oral administration may contain binders acceptable in human and veterinary pharmaceutical practice, sweeteners, disintegrating agents, diluents, flavourings, coating agents, preservatives, lubricants and/or time delay agents. Suitable binders include gum acacia, gelatine, corn starch, gum tragacanth, sodium alginate, carboxymethylcellulose or polyethylene glycol Suitable sweeteners include sucrose, lactose, glucose, aspartame or saccharine. Suitable disintegrating agents include corn starch, methylcellulose, polyvinylpyrrolidone, guar gum, xanthan gum, bentonite, alginic acid or agar. Suitable diluents include lactose, sorbitol, mannitol, dextrose, kaolin, cellulose, calcium carbonate, calcium silicate or dicalcium phosphate. Suitable flavouring agents include peppermint oil, oil of wintergreen, cherry, orange or raspberry flavouring. Suitable coating agents include polymers or copolymers of acrylic acid and/or methacrylic acid and/or their esters, waxes, fatty alcohols, zein, shellac or gluten. Suitable, preservatives include sodium benzoate, vitamin E, alpha-tocopherol, ascorbic acid, methyl paraben, propyl paraben or sodium bisulfite. Suitable lubricants include magnesium stearate, stearic acid, sodium oleate, sodium chloride or talc. Suitable time delay agents include glyceryl monostearate or glyceryl distearate. Liquid forms for oral administration may contain, in addition to the above agents, a liquid carrier. Suitable liquid carriers include water, oils such as olive oil, peanut oil, sesame oil, sunflower oil, safflower oil, arachis oil, coconut oil, liquid paraffin, ethylene glycol, propylene glycol, polyethylene glycol, ethanol, propanol, isopropanol, glycerol, fatty alcohols, triglycerides, or mixtures thereof.

Suspensions for oral administration may further comprise dispersing agents and/or suspending agents. Suitable suspending agents include sodium carboxymethylcellulose, methylcellulose, hydroxypropylmethyl-cellulose, poly-vinyl-pyrrolidone, sodium alginate or acetyl alcohol. Suitable dispersing agents include lecithin, polyoxyethylene esters of fatty acids such as stearic acid, polyoxyethylene sorbitol mono- or di-oleate, -stearate or -laurate, polyoxyethylene sorbitan mono- or dieleate, stearate or -laurate, and the like.

The emulsions for oral administration may further comprise one or more emulsifying agents. Suitable emulsifying agents include dispersing agents as exemplified above, or natural gums such as guar gum, gum acacia or gum tragacanth.

The topical formulations of the present invention, comprise an active ingredient together with one or more acceptable carriers, and optionally any other therapeutic ingredients.

Formulations suitable for topical administration include liquid or semi-liquid preparations suitable for penetration through the skin to the site of where treatment is required, such as liniments, lotions, creams, ointments or pastes, and drops suitable for administration to the eye, ear or nose.

Drops according to the present invention may comprise sterile aqueous or oily solutions or suspensions. These may be prepared by dissolving the active ingredient in an aqueous solution of a bactericidal and/or fungicidal agent and/or any other suitable preservative, and optionally including a surface active agent. The resulting solution may then be clarified by filtration, transferred to a suitable container and sterilised. Sterilisation may be achieved by: autoclaving or maintaining at 90° C.-100° C. for half an hour, or by filtration, followed by transfer to a container by an aseptic technique. Examples of bactericidal and fungicidal agents suitable for inclusion in the drops are phenylmercuric nitrate or acetate (0.002%), benzalkonium chloride (0.01%) and chlorhexidine acetate (0.01%). Suitable solvents for the preparation of an oily solution include glycerol, diluted alcohol and propylene glycol.

Lotions according to the present invention include those suitable for application to the skin or eye. An eye lotion may comprise a sterile aqueous solution optionally containing a bactericide and may be prepared by methods similar to those described above in relation to the preparation of drops. Lotions or liniments for application to the skin may also include an agent to hasten drying and to cool the skin, such as an alcohol or acetone, and/or a moisturiser such as glycerol, or oil such as castor oil or arachis oil.

Creams, ointments or pastes according to the present invention are semi-solid formulations of the active ingredient for external application. They may be prepared by mixing the active ingredient in finely-divided or powdered form, alone or in solution or suspension in an aqueous or non-aqueous fluid, with a greasy or non-greasy basis. The basis may comprise hydrocarbons such as hard, soft or liquid paraffin, glycerol, beeswax, a metallic soap; a mucilage; an oil of natural origin such as almond, corn, arachis, castor or olive oil; wool fat or its derivatives, or a fatty acid such as stearic or oleic acid together with an alcohol such as propylene glycol or macrogols.

The formulation may incorporate any suitable surface active agent such as an anionic, cationic or non-ionic surface active such as sorbitan esters or polyoxyethylene derivatives thereof. Suspending agents such as natural gums, cellulose derivatives or inorganic materials such as silicaceous silicas, and other ingredients such as lanolin, may also be included.

The compositions for parenteral administration will commonly comprise a solution of a compound of the present invention or a cocktail thereof dissolved in an acceptable carrier, such as water, buffered water, 0.4% saline, and 0.3% glycine etc, wherein such solutions are sterile and relatively free of particulate matter.

Methods for preparing parenterally administrable compositions are apparent to those skilled in the art, and are described in more detail in, for example, Remington's Pharmaceutical Science, 15th ed., Mack Publishing Company, Easton, Pa., hereby incorporated by reference herein.

The pharmaceutical compositions of the invention may also be administered in the form of liposomes. Liposomes are generally derived from phospholipids or other lipid substances, and are formed by mono- or multi-lamellar hydrated liquid crystals that are dispersed in an aqueous medium. Any non-toxic, physiologically acceptable and metabolisable lipid capable of forming liposomes can be used. The formulations of the present invention in liposome form may contain, in addition to a compound of the present invention, stabilisers, preservatives, excipients and the like. The preferred lipids are the phospholipids and the phosphatidylcholines (lecithins), both natural and synthetic. Methods to form liposomes are known in the art, and in relation to this specific reference is made to: Prescott, Ed., Methods in Cell Biology, Volume XIV, Academic Press, New York, N.Y. (1976), p. 33 et seq., the contents of which is incorporated herein by reference.

Depending on the intended result, the pharmaceutical composition of the present invention can be administered for prophylactic and/or therapeutic treatments. In a therapeutic application, compositions are administered to a patient already suffering from a disease, in an amount sufficient to cure or at least partially arrest the disease and its complications. In prophylactic applications, compositions containing the compound or a cocktail thereof are administered to a patient not already in a diseased state to enhance the patients resistance.

Typically, the compounds of the invention may be used in combination with other known treatments, such as surgery and/or therapeutic agents, including chemotherapeutic or radiotherapeutics. More typically, when used in the treatment of solid tumours, compounds of the present invention may be administered with chemotherapeutic agents such as: adriamycin, taxol, fluorouricil, melphalan, cisplatin, alpha interferon, COMP (cyclophosphamide, vincristine, methotrexate and prednisone), etoposide, mBACOD (methortrexate, bleomydin, doxorubicin, cyclophosphamide, vincristine and dexamethasone), PROMACE/MOPP (prednisone, methotrexate (wileucovin rescue), doxorubicin, cyclophosphamide, taxol, etoposidelmechlorethamine, vincristine, s prednisone and procarbazine), vincristine, vinblastine, angioinhibins, TNP-470, pentosan polysulfate, platelet factor 4, angiostatin, LM-609, SU-101, CM-101, Techgalan, thalidomide, SP-PG and the like. Other chemotherapeutic agents include alkylating agents such as nitrogen mustards including mechloethamine, melphan, chlorambucil, cyclophosphamide and ifosfamide; nitrosoureas including carmustine, lomustine, semustine and streptozocin; alkyl sulfonates including busulfan; triazines including dacarbazine; ethyenimines including thiotepa and hexamethylmelamine; folic acid analogues including methotrexate; pyrimidine analogues including 5-fluorouracil, cytosine arabinoside; purine analogues including 6-mercaptopurine and 6-thioguanine; antitumour antibiotics including actinomycin D; the anthracyclines including doxorubicin, bleomycin, mitomycin C and methramycin; hormones and hormone antagonists including tamoxifen and cortiosteroids and miscellaneous agents including cisplatin and brequinar.

3. General Assay for Determining the Active Concentration of As in Solution.

The active concentration of trivalent arsenicals can be determined by the following general method which comprises the steps of:

(i) preparing arsenical solutions comprising increasing concentrations of a trivalent arsenical; titrating said arsenical solutions with a second solution comprising a known concentration of a dithiol;

adding to each solution a sufficient amount of a dithiol detecting reagent;

spectroscopically measuring each arsenical solution to determine the amount of excess dithiol; and calculating the active concentration of said trivalent arsenical in said solution.

Typically, the assay for trivalent arsenicals depends upon the ability of trivalent arsenicals to bind tightly to closely spaced dithiols, for example 2,3-dimercaptopropanol (DMP), and for free thiols to be detected photometrically using a suitable reagent and detector. The active concentration of trivalent arsenical is found by titrating the arsenical with a dithiol, then determining the amount of free thiol remaining in solution (ie, excess dithiol) with a suitable reagent. Solutions with increasing concentrations of the arsenical are prepared, and to each is added a constant amount of a dithiol such that there is more dithiol than the smallest amount of arsenical but less dithiol than the largest. Those solutions with an excess of dithiol will give a photometrically measurable colour change upon addition of a suitable reagent, and the actual concentration of dithiol can be determined by measuring the absorbance at a suitable wavelength. Those solutions with excess arsenical will not change colour as all thiol will be bound to As. Plotting the results gives the equivalence point (where the concentration of dithiol=concentration of As), and as the initial concentration of dithiol added to all solutions is known, the active concentration of As can be determined.

The invention will now be described in greater detail by reference to specific Examples, which should not be construed as in any way limiting the scope of the invention.

EXAMPLE 1

Synthesis of Compounds of the Invention

The following chemicals were purchased and used without further purification: phenylarsenoxide, bromoacetyl bromide, sulfur dioxide, drdimethylsulfoxide, deuterium oxide, L-aspartic acid, L-glutamic acid, D-glucosamine hydrochloride (Aldrich, Castle Hill, NSW); methanol, 98% sulfuric acid, 48% hydrobromic acid, 37% hydrochloric acid (Ajax, Auburn, NSW); dichloromethane, potassium hydroxide, sodium hydrogen carbonate, sodium hydroxide (BDH, Kilsyth, VIC); P-2 Gel extra fine 1,800 MW cut-off (Bio-Rad, Hercules, Calif.); 2,3-dimercaptopropanol (DMP), L-cysteic acid (Fluka, Castle Hill, NSW); thionyl chloride (Merck, Darmstadt, Germany); 6,8-thioctic acid, dithiothreitol, dimethylsulfoxide, 5,5'-dithiobis(2-nitrobenzoic acid), ethylenediaminetetraacetic acid, N-(2-hydroxyethyl)piperazine-N'-(2-ethanesulfonic acid), glutathione, sodium carbonate, sodium chloride, sodium iodide (Sigma, Castle Hill, NSW); p-arsanilic acid (Tokyo Kasei Kogyo, Tokyo, Japan); glycine (ICN, Aurora, Ohio). 3-(fluorescein-5-carbamoylmethylthio)propanoic acid, succinimidyl ester (fluorescein-5-EX, SE), 6-(fluorescein-x-carboxamido)hexanoic acid (mixed isomers; x=5 or 6), succinimidyl ester (5(6)-SFX), and 6-((6-((biotinoyl)amino)hexanoyl)amino)hexanoic acid, succinimidyl ester (biotin-XX, SE) were obtained from Molecular Probes, Eugene, Oreg. Cy™5.5 monofunctional dye was obtained from Amersham Pharmacia Biotech, Little Chalfont, Buckinghamshire, UK. All other reagents were of analytical grade.

Instrumentation—1D and 2D NMR spectra were obtained using a Bruker DPX300 nuclear magnetic resonance spectrometer, with $^1$H and $^{13}$C detected at 300.17 MHz and 75.48 MHz, respectively. UV-visible absorbances were recorded on a Molecular Devices Thermomax Plus (Palo Alto, Calif.) microplate reader.

Preparation of acidified deuterium oxide—Fresh thionyl chloride was cautiously added to an excess of deuterium oxide. After evolution of $SO_2$ had ceased, the resulting solution (0.6 ml) was added to GSAO (ca 50 mg) in a 5 mm NMR tube. This sample was used to obtain the NMR spectra.

EXAMPLE 1(a)

Synthesis of
4-(N-(S-glutathionylacetyl)amino)phenylarsenoxide
(GSAO)

Figure 3:
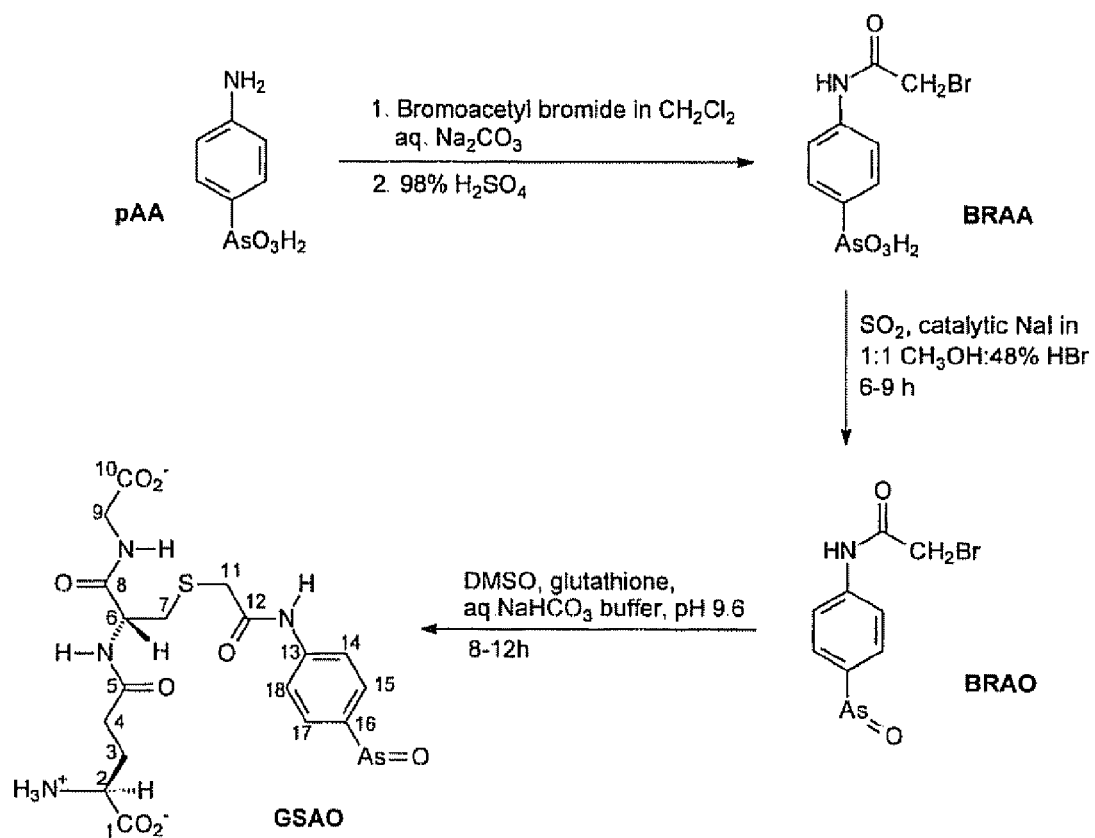
FIG. 3. Synthesis of GSAO. Schematic representation of the synthesis of GSAO showing the stereochemistry and the numbering scheme used in the discussion of the 2D $^1$H-$^{13}$C HMBC NMR spectrum FIG. 4. Assignment of the Structure of GSAO. An expansion of the $^1$H-$^{13}$C HMBC spectrum of GSAO in DCl/D$_2$O, showing the aliphatic region. The spectrum shows any long-range heteronuclear ($^1$H-$^{13}$C) coupling as crosspeaks, in line with the corresponding $^1$H and $^{13}$C signals along the horizontal and vertical axes. The boxed crosspeaks correspond to $^1$H-$^{13}$C coupling between the C7 and C11 methylenes, confirming that alkylation by BRAO has occurred on the glutathione sulfur atom. Peaks and crosspeaks marked "i" are due to impurities; one-bond crosspeaks corresponding to the C9 methylene and the C2 methine are also observable as doublets due to incomplete filtering by the HMBC pulse sequence.

The total synthesis of GSAO is represented schematically in FIG. 3.

Synthesis of
4-(N-(bromoacetyl)amino)phenylarsonic acid
(BRAA)

Sodium carbonate (40.14 g, 378.7 mmol) was added to water (200 mL) and stirred at room temperature until all solids had dissolved. To the stirred carbonate solution was added p-arsanilic to acid (29.99 g, 138.2 mmol), portionwise, and the volume of the solution made up to 300 mL with addition of more water. The solution (pH 10 to 11) was allowed to stir for 30 mins, and if necessary, was filtered to remove any undissolved solid before being refridgerated for 2 to 3 hours.

The solution was transferred to a separating funnel and ice chips were added. Bromoacetyl bromide (15 mL, 34.76 g, 172.1 mmol) was diluted in dichloromethane (50 mL) and approximately is half of the dichloromethane solution was added carefully to the cold aqueous solution. The mixture was cautiously shaken, with frequent venting to avoid excessive build up of pressure. After 1 to 2 mins, the evolution of carbon dioxide had subsided, and more vigorous shaking was undertaken. The remaining portion of bromoacetyl bromide was carefully added and the procedure repeated. When the reaction was over, the solution was found to be pH 7 The lower dichloromethane layer was discarded, and the aqueous layer transferred to a 1 L flask and carefully acidified by dropwise addition of 98% sulfuric acid. Complete precipitation of the white product required addition of acid until the solution was approximately pH 1. The crude product was collected and dried at the pump, typically in yields of 50% to 75%. $^1$H-NMR ($d_6$DMSO): δ 4.09 (s, 2H), 7.73 (d, J=9 Hz, 2H), 7.83 (d, J=9 Hz, 2H), 10.87 (s, 1H). $^{13}$C-NMR ($d_6$DMSO): δ 30.53, 119.97, 127.34, 131.56, 143.08, 166.00 ppm.

Synthesis of
4-(N-bromoacetyl)amino)phenylarsenoxide hydrate
(BRAO.xH$_2$O)

Into a 3-necked 500 mL round-bottomed flask was placed BRAA (12.15 g, 36 mmol). The solid was dissolved with swirling in a mixture of methanol (75 mL) and hydrobromic acid (48%, 75 mL), giving a transparent yellow solution. The solution was filtered to remove residual solids. Sodium iodide (0.20 g, 1.3 mmol) was added as a catalyst, whereupon the colour of the solution darkened to orange-brown, then sulfur dioxide gas was slowly (ca. 2 bubbles per second) passed through the stirred solution for approximately 2.5 hours. The resultant white precipitate was collected using a Buchner funnel, giving the product (17.43 g) as a damp white solid. The activity of a solution made by dissolving a portion of the solid (40.7 mg) in deoxygenated DMSO (800 µL) was determined to be 56 mM (see below). Hence, the molecular weight of BRAO.xH$_2$O is 908.5, that is, 35% w/w BRAD and 65% w/w H$_2$OD Therefore, the "anhydrous" weight of the BRAO product was 35% of 17.43 g, that is, 6.10 g (19 mmol, 53% yield). $^1$H-NMR ($d_6$-DMSO): δ 4.85 (s, s 2H), 7.78 (d, J=9 Hz, 2H), 7.86 (d, J=9 Hz, 2H), 11.36 (s, 1H). $^{13}$C-NMR ($d_6$-DMSO): δ 30.55, 119.22, 130.52, 140.04, 145.04, 165.52 ppm.

Synthesis of
4-(N-(S-glutathionylacetyl)amino)phenylarsenoxide
(GSAO)

DMSO (10 mL) was deoxygenated by passing a stream of nitrogen gas through it for a few minutes, and used to dissolve BRAO.xH$_2$O (1.00 g, 2.48 mmol active arsenoxide). Glutathione (1.15 g, 3.74 mmol, 1.5 eq) was dissolved in 0.5 M bicarbonate buffer, pH 9.6 (35 mL), and added to the solution of BRAO.xH$_2$O in DMSO. The total volume was made up to 50 mL with 0.5 M bicarbonate buffer, and the solution gently agitated at room temperature overnight. Cautious neutralisation with 37% hydrochloric acid, followed by lyophilisation gave a white powdery product, which could be dissolved in water leaving no residual solid. The active arsenoxide concentration of the resultant solution was found to be 49.6 mM, determined using the DMP/DTNB assay (see below).

Figure 4:
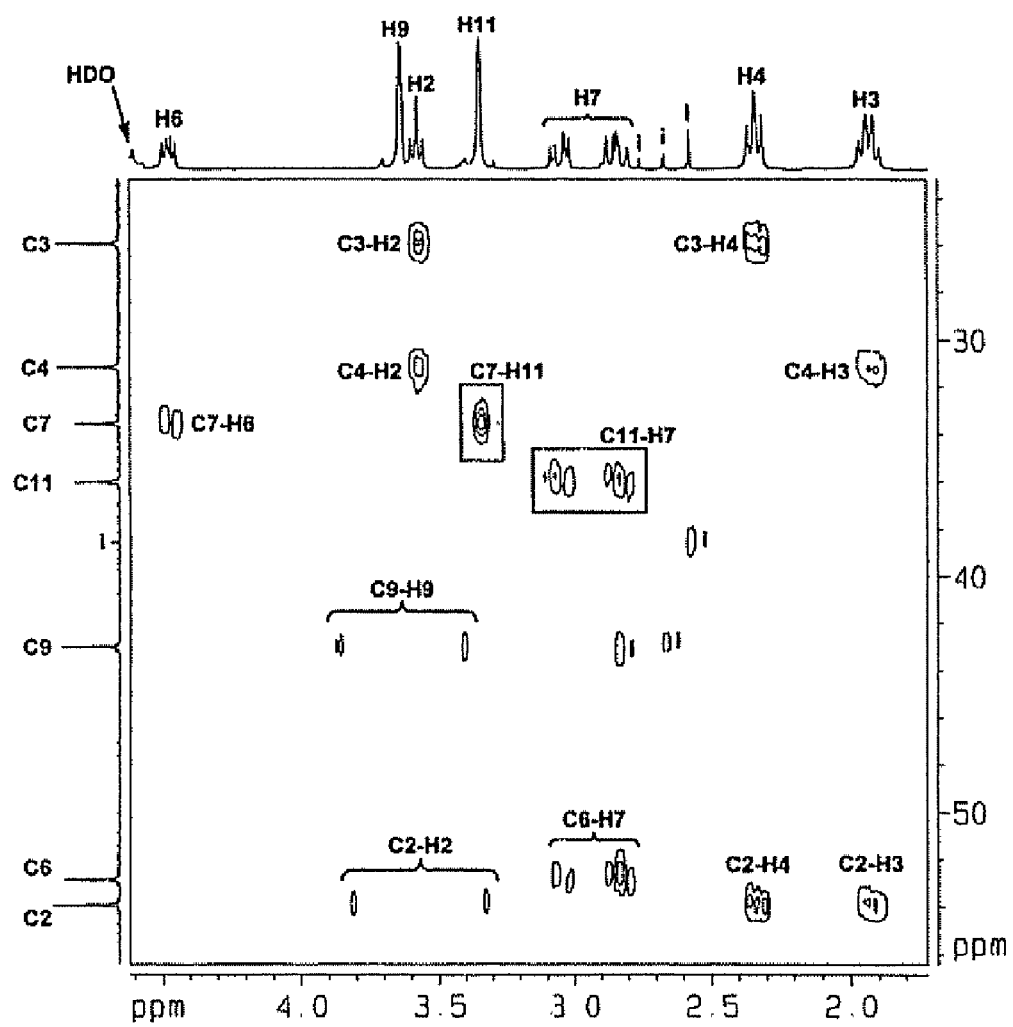

The product was purified using gel-filtration (P-2 Gel extra fine, 1.8 kDa cutoff, 50 g) on a 130 mL column, using 20 mM Hepes, 0.14 M NaCl, 1 mM EDTA, pH 7.4 buffer as the eluant at a flow rate of 0.10 mL/min. A total of 144 mL was collected (72 fractions of 2 mL) and monitored by UV (λ 214 nm). Four peaks, A, B, C and D, were resolved. Peaks B and C showed activity in the DTNB/DMP assay (see below), and were assigned as GSAO and unreacted BRAO, respectively. Peaks A and D were tentatively assigned as the oxidation products GSSM and BRAA (the oxidation product of BRAO), respectively (see below). Unreacted GSH was also detected (using DTNB) in the fractions corresponding to Peak A. The fractions corresponding to peak B were combined and deoxygenated with nitrogen gas to give a solution of GSAO (15 mM, approximately 12 mL), $^1$H-NMR (D$_2$O): δ 1.93 (q, J=7 Hz, 2H), 2.35 (t, J=8 Hz, 2H), 2.8 (dd, J=14 Hz, J=9 Hz, 1H), 3.05 (dd, J=14 Hz, J=5 Hz, 1H), 3.35 (s, 2H), 3.58 (t, J=6 Hz, 1H), 3.64 (d, J=2 Hz, 2H), 4.48 (dd, J=9 Hz, J=5 Hz, 1H), 7.44 (d, J=8 Hz, 2H), 7.58 (d, J=8 Hz, 2H). $^{13}$C-NMR (D$_2$O): δ 25.93, 31.16, 33.53, 36.01, 42.97, 52.83, 53.89, 121.29, 129.97, 138.77, 144.09, 170.90, 171.73, 173.75, 174.68, 175.76 ppm, 2D NMR spectroscopy was also used to confirm the structure of GSAD. A series of $^1$H and $^{13}$C NMR spectra, $^1$H, $^{13}$C, $^1$H-$^1$H COSY, $^1$H-$^{13}$C HMQC and $^1$H-$^{13}$C HMBC, were all found to be consistent with the structure proposed in FIG. 3. Considered together, all of the spectra permitted the unambiguous assignment of all carbon and non-exchangeable hydrogen atoms. An expansion of the $^1$H-$^{13}$C HMBC spectrum of GSAO, showing the aliphatic region, is shown in FIG. 4. The $^1$H-$^{13}$C HMBC technique correlates coupled $^1$H and $^{13}$C nuclei, but filters out directly bonded nuclei. This means that $^1$H and $^{13}$C nuclei that are separated by two, three, or (sometimes) four bonds appeared as crosspeaks in the spectrum. FIG. 4 shows that C11 is only strongly coupled to H7 (referring to the protons attached to C7), while C7 is strongly coupled to H11 in addition to H6. This confirms that the GSH sulfur was successfully alkylated with BRAO.

EXAMPLE 1(b)

Synthesis of
4-(N-(S-glutathionylacetyl)amino)phenylarsonic acid
(GSAA)

Figure 5:
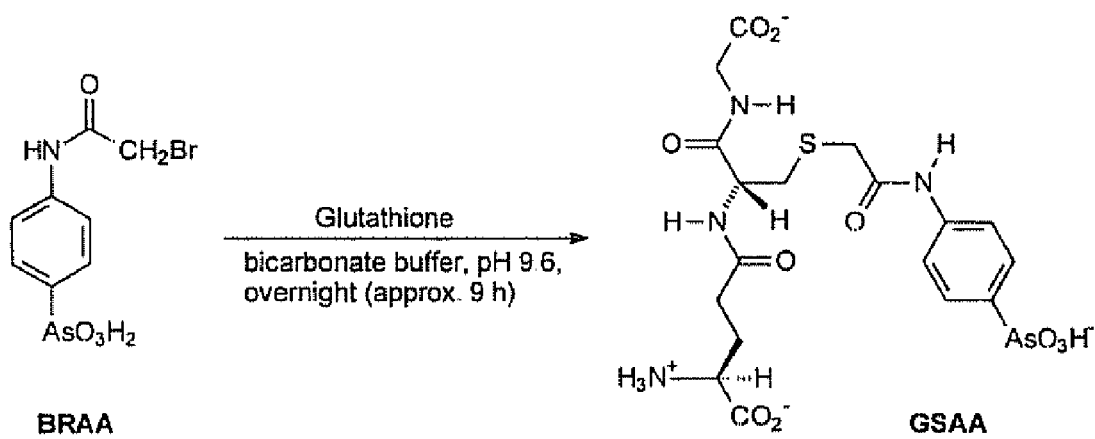
FIG. 5. Schematic representation of the synthesis of GSAA

The synthesis of GSAA is represented schematically in FIG. 5.

BRAA (1.00 g 2.96 mmol) and glutathione (1.36 g, 4.44 mmol, 1.5 eq) were dissolved in 0.5 M bicarbonate buffer, pH 9.6 (50 mL), and the solution gently agitated at room temperature overnight. Lyophilisation gave a white powdery product which was freely soluble in water, leaving no solid residue. The product was purified by gel-filtration on a 570 mL column (2.5×117 cm) of Bio-Gel P-2 extra fine (BioRad, Hercules, Calif.) using deionised water as the eluant at a flow rate of 0.1 mL per min. The product (GSAA) eluted from the column in a position corresponding to Peak A in the purification of GSAO.

EXAMPLE 1(c)

Synthesis of 4-(N-(S-((N-(6-((6-((biotinoyl)amino) hexanoyl)amino)hexanoyl)glutathionyl)acetyl)- amino)phenylarsenoxide (GSAO-B)

The synthesis of GSAO-B is represented schematically in FIG. 6.

GSAO (0.13 g) was dissolved in 0.5 M sodium bicarbonate buffer (5 mL, pH 8.5) and the concentration of active arsenical in the resultant solution was determined to be 39 mM. The buffered arsenical solution (4.2 mL, containing 165 μmol active arsenical) was added to a solution of biotin-XX, SE (100 mg, 176 μmol) in DMSO (1 mL), the mixture inverted a few times and then incubated at 4° C. for 4 hours. Glycine (17.5 mg, 233 μmol) was added and the mixture kept at 4° C. overnight. The concentration of trivalent arsenical in the GSAO-B product was determined to be 31 mM and the solution was used without further modification.

EXAMPLE 1(d)

Synthesis of 4-(N-(S-(N-(3-fluorescein-5-carbamoyl- methylthio)propanoyl)glutathionyl)acetyl)amino- phenylarsenoxide (GSAO-F)

Figure 7:
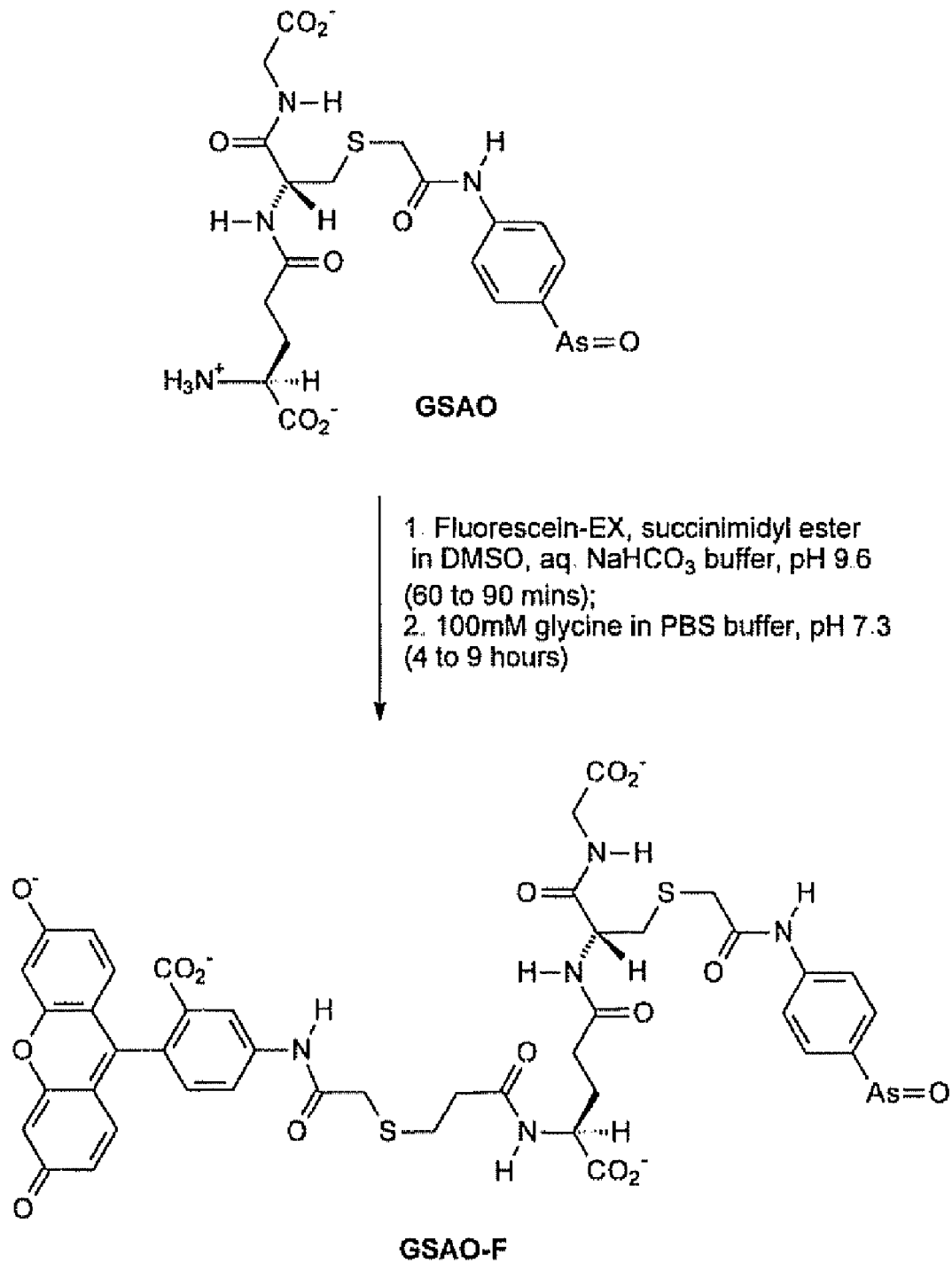
FIG. 7. Schematic representation of the synthesis of GSAO-F

The synthesis of GSAO-F is represented schematically in FIG. 7.

A solution of fluorescein-5-EX succinimidyl ester (2.4 mg, 4.1 μmol) in DMSO (240 μL) was added to GSAO (33.8 mM) in Mes buffer, pH 5.5 (5 mM, 473 μL), and the mixture was diluted with bicarbonate buffer, pH 9 (0.5 M, 3.287 mL) and allowed to stand at room temperature for 80 mins. The yellow solution was then diluted with glycine (100 mM) in PBS (4 mL), and allowed to stand at room temperature overnight. The final solution contained trivalent arsenical (2.00 mM) and glycine (50 mM).

EXAMPLE 1(e)

Synthesis of GSAO-Cy™5.5

Figure 8:
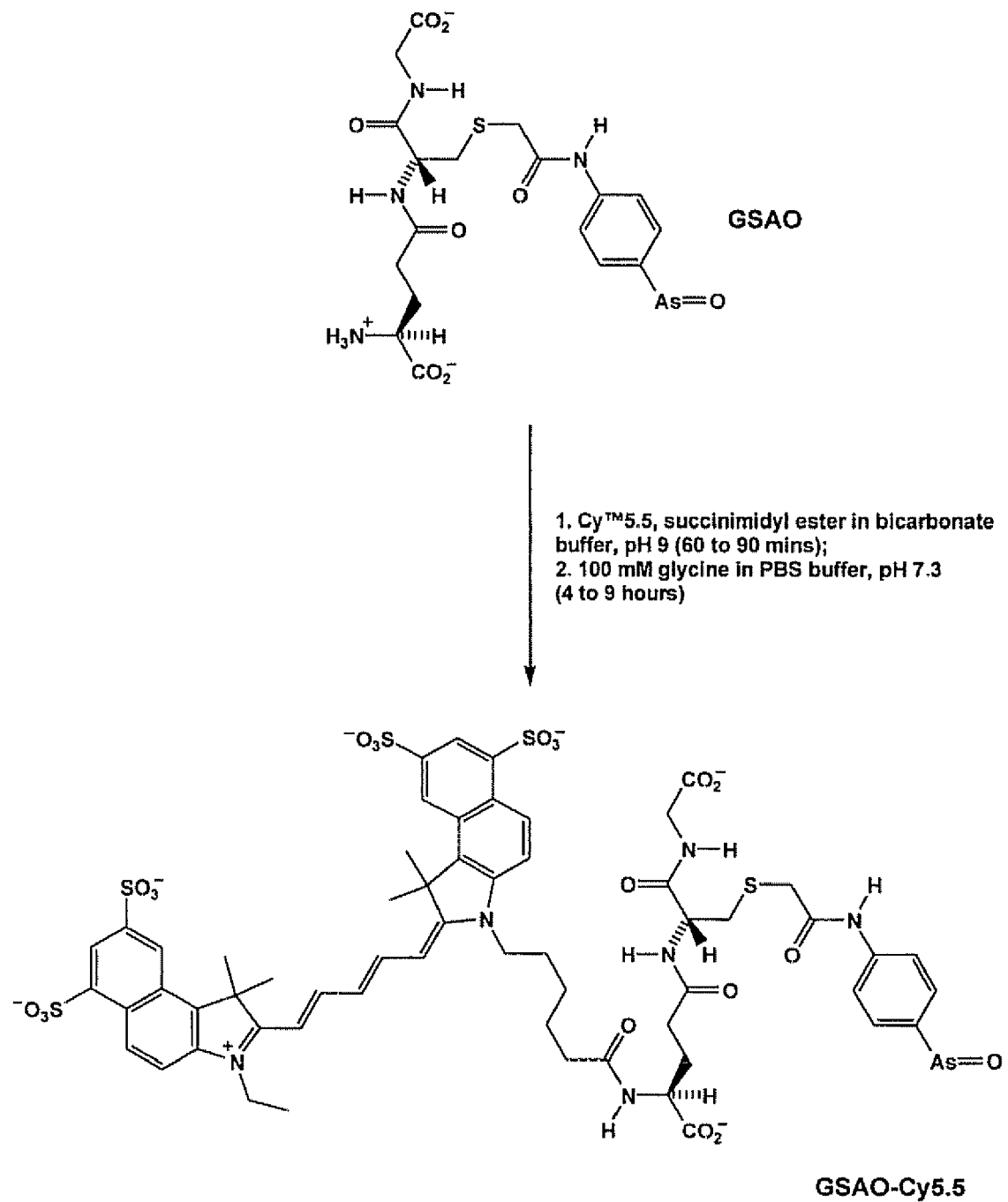
FIG. 8: Schematic representation of the synthesis of GSAO-Cy™5.5

The synthesis of GSAO-Cy™5.5 is represented schematically in FIG. 8.

A solution of Cy™5.5 (266 nmol) in bicarbonate buffer, pH 9 (0.5 M, 968 μL) was mixed with a solution of GSAO (33.8 mM) in Mes buffer, pH 5.5 (5 mM, 32 μL), and allowed to stand at room temperature for 80 mins. The blue solution was then diluted with glycine (100 mM) in PBS (1 mL), and allowed to stand at room temperature overnight. The final solution contained trivalent arsenical (0.54 mM) and glycine (50 mM).

EXAMPLE 1(f)

Synthesis of 4-aminophenylarsenoxide (pAPAO)

Figure 9:
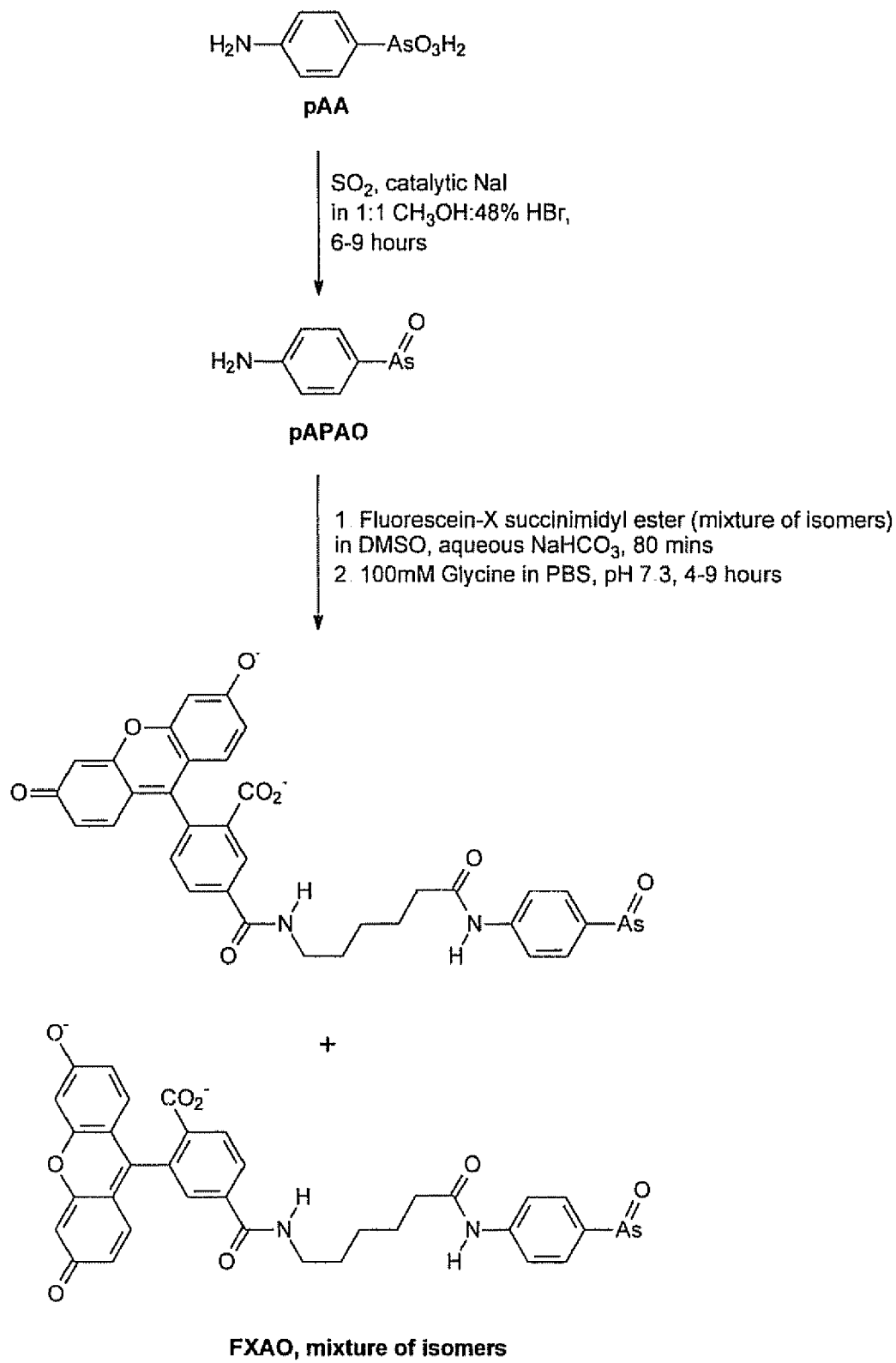
FIG. 9. Synthesis of FXAO

The synthesis of pAPAO is represented schematically in FIG. 9.

Hydrobromic acid (48%, 35 mL) was added to a suspension of p-arsanilic acid (7.76 g, 35.8 mmol) in methanol (35 mL) with stirring. Sodium iodide (ca 0.05 g, 0.33 mmol) was added then the solution was placed in a water bath (room temperature). Sulfur dioxide was bubbled through the stirred solution at a rate of about 2 bubbles per second. After 2 hours, a white precipitate had formed. The reaction was allowed to proceed overnight, by which time most of the solid had redissolved. The remaining solid was collected and dried at the pump, yielding 3.89 g. A solution of pAPAO (24 mg) in DMSO (1 mL) was prepared, and the active concentration of trivalent arsenical was determined (see determination of GSAO activity). From this, the product was found to consist of 3.57 mmol active arsenical (10% yield).

EXAMPLE 1(g)

Synthesis of a mixture of 4-(N-(6-(fluorescein-5- carboxamido)hexanoyl)amino)-phenylarsenoxide and 4-(N-(6-(fluorescein-6-carboxamido)hexanoyl) amino)-phenylarsenoxide (FXAO)

The synthesis of FXAO is represented schematically in FIG. 9.

A solution of a mixture of 6-(fluorescein-5-carboxamido) hexanoic acid, succinimidyl ester and 6-(fluorescein-6-carboxamido)hexanoic acid, succinimidyl ester (4.9 mg, 8.29 μmol) in DMSO (107 μL) was added to pAPAO (22 mM) in DMSO (193 μL). The mixture was diluted with 0.5 M bicarbonate buffer, pH 9 (700 μL) then allowed to stand at room temperature for 80 mins. The yellow solution was diluted with glycine (100 mM) in PBS (1 mL), and allowed to stand at room temperature overnight. The final solution contained trivalent arsenical (2.12 mM) and glycine (50 mM).

EXAMPLE 1(h)

Synthesis of 3,3'-dithiobis(propanoic acid)

Figure 10:
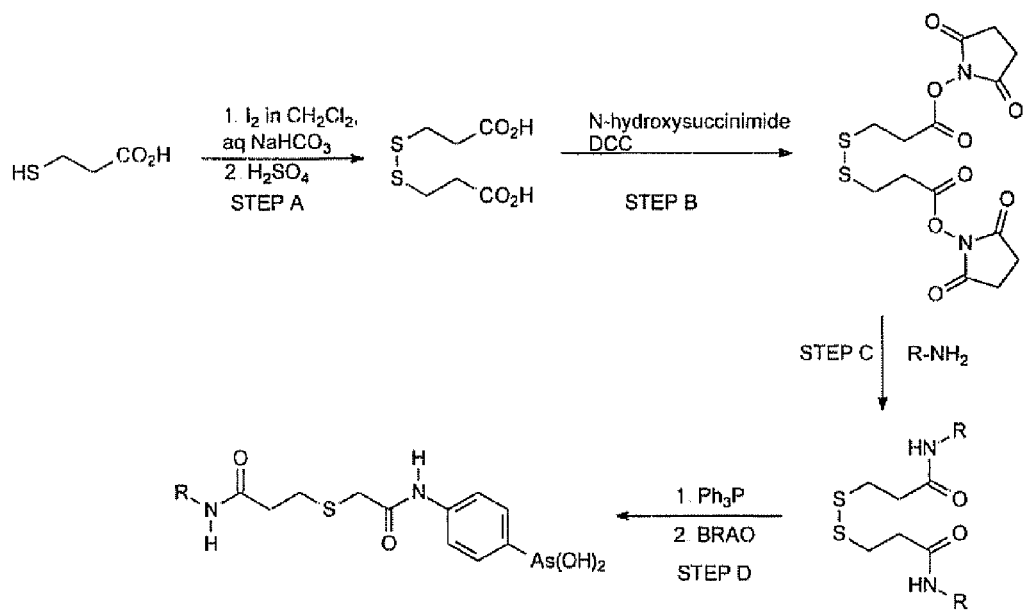
FIG. 10. General synthetic route for compounds of the invention where A is a hydrophilic amine. Examples of R—NH$_2$ include D-glucosamine; L-aspartic acid; L-glutamic acid; and L-cysteic acid.

A scheme outlining the synthesis is provided in FIG. 10.

Sodium carbonate (64.0 g, 604 mmol) was added to water (300 mL) and the solution stirred at room temperature until all solids had dissolved, 3-Mercaptopropanoic acid (50 mL, 60.9 g, 574 mmol) was added dropwise to the stirred carbonate solution at such a rate -that evolution of carbon dioxide did not become excessively vigorous. Dichloromethane (50 mL) was added to the resulting suspension, followed by portion-wise addition of iodine (71.44 g, 281 mmol, 0.49 eq). During the addition of iodine, vigorous evolution of carbon dioxide was observed. The mixture was transferred to a 500 mL separating funnel, and the lower organic layer discarded. The aqueous layer was filtered, and cautiously acidified to pH 1 with 98% sulfuric acid. The precipitate was collected and dried at the pump to give the product (43.4 g, 72% yield), $^1$H-NMR (d$_6$DMSO): δ 2.59 (t, J=7 Hz, 2H), 2.86 (t, J=7 Hz, 2H), 12.25 (s, 1H). $^{13}$C-NMR (d$_6$DMSO): δ 33.4, 34.0, 173.0 ppm.

EXAMPLE 1(i)

Synthesis of 3,3'-dithiobis(propanoic acid, succinimidyl ester)

A scheme outlining the synthesis is provided in FIG. 10.
3,3'-Dithiobis(propanoic acid) (9.5 g, 45.2 mmol) was dissolved in a mixture of acetone (600 mL) and dichloromethane (600 mL) with stirring at room temperature. N-Hydroxysuccinimide (12.68 g, 110.2 mmol, 2.44 eq) was dissolved in the solution, then 1,3-dicyclohexylcarbodiimide (25.9 g, 125.5 mmol, 2.78 eq) was cautiously added. The mixture was allowed to stir at room temperature for 24 hours, after which time the solution was vacuum filtered and the residual solid discarded. The solvent was removed from the filtrate under vacuum, and the oily residue was re-dissolved in dichloromethane (ca 200 mL). The solution was reduced in volume (ca. 50 mL) and cooled, giving the product as a colourless, crystalline solid (8.90 g, 49% yield), $^1$H-NMR (d$_6$-DMSO): δ 2.80 (s, 8H), 3.05 (m, 8H). $^{13}$C-NMR (d$_6$-DMSO): δ 25.8, 30.7, 32.3, 167.9, 170.4 ppm.

EXAMPLE 1(j)

Synthesis of the disulfide of disodium N-(3-mercaptopropanoyl)-L-aspartate

A scheme outlining the synthesis is provided in FIG. 10.
L—Aspartic acid (0.42 g, 3.16 mmol) was mixed with sodium hydrogen carbonate (0.50 g, 5.95 mmol, 1.9 eq), then water (1 mL) was added. The sodium hydrogen carbonate was added to quench the acidic hydrogens present in L-aspartic acid. When evolution of carbon dioxide had subsided, the mixture was diluted with 0.5 M bicarbonate buffer, pH 9 (19 mL, 9.5 mmol). All solids dissolved with swirling and the solution was found to be pH 9. 3,3'-Dithiobis(propanoic acid, succinimidyl ester) (0.247 M in DMSO, 5 mL, 1.24 mmol) was added dropwise to the aqueous carbonate solution with stirring. Immediately, a white precipitate appeared, but upon vigorous shaking it redissolved. After 24 hours, during which time the mixture was periodically shaken, dichloromethane (1 mL) was added, and the mixture was again allowed to stand for 24 hours with periodic shaking. The solution, (pH 9) was acidified to pH 7 by the dropwise addition of 32% hydrochloric acid. The product was precipitated by the slow, dropwise addition of the solution to a stirred beaker of absolute ethanol (300 mL) at room temperature, giving a fluffy white precipitate which was collected by filtration and dried under vacuum, giving the product as a white solid (0.37 g, 53% yield). $^{13}$C-NMR (D$_2$O): δ 33.2, 34.8, 37.2, 50.9, 175.6, 176.0, 176.4 ppm.

EXAMPLE 1(k)

Synthesis of the disulfide of disodium N-(3-mercaptopropanoyl)-L-glutamate

A scheme outlining the synthesis is provided in FIG. 10.
The procedure used was the same as for the disulfide of disodium N-(3-mercapto-propanoyl)-L-aspartate, using L-glutamic acid (0.44 g, 2.99 mmol) and sodium hydrogen carbonate (0.55 g, 6.55 mmol, 2.2 eq). The product was obtained as a white solid (0.61 g, 87% yield). $^{13}$C-NMR (D$_2$O): δ 28.5, 33.2, 34.1, 35.0, 55.2, 173.6, 179.2, 181.2 ppm.

EXAMPLE 1(l)

Synthesis of the disulfide of disodium N-(3-mercaptopropanoyl)-L-cysteate

A scheme outlining the synthesis is provided in FIG. 10.
The procedure used was the same as for the disulfide of disodium N-(3-mercaptopropanoyl)-L-aspartate, using L-cysteic acid (0.59 g, 3.15 mmol) and sodium hydrogen carbonate (0.56 g, 6.67 mmol, 2.1 eq). The product was obtained as a white solid (0.68 g, 79% yield). $^{13}$C-NMR (D$_2$O): δ 33.5, 35.7, 50.8, 52.3, 174.1, 178.9 ppm.

EXAMPLE 1(m)

Synthesis of the disulfide of disodium N-3-mercaptopropanoyl)-D-glucosamine

A scheme outlining the synthesis is provided in FIG. 10.
The procedure followed that for the amino acid derivatives described above, using D-glucosamine hydrochloride (0.67 g, 3.11 mmol), except that no additional sodium hydrogen carbonate was added initially, and the product was precipitated with AR acetone (300 mL) instead of ethanol. The product was obtained as a white solid (0.67 g, 81% yield). $^{13}$C-NMR (D$_2$O): δ 33.8, 35.4, 35.7, 39.3, 54.6, 57.2, 61.1, 61.2, 70.4, 70.6, 71.1, 72.0, 74.3, 76.4, 91.3, 95.4 ppm.

EXAMPLE 1(n)

Synthesis of N-(3-(4-arsenosophenylcarbamoylmethyio)propanoyl)-L-aspartic acid (AspAO)

A solution of 70.0 mM BRAO in DMSO (1.68 mL, 118 μmol) was mixed with a solution of the disulfide of disodium N-(3-mercaptopropanoyl)-L-aspartate (0.37 g) dissolved in 0.5 M bicarbonate buffer, pH 9 (6.72 mL, 3.4 mmol). Added to the solution was 0.69 M triphenylphosphine in DMSO (1.1 mL, 760 μmol). There was an immediate precipitation of what was presumed to be insoluble triphenylphosphine, so DMSO (1 mL) was added, and the mixture shaken thoroughly, and left to stand at room temperature overnight. The mixture was filtered, and acidified to pH 4 with the dropwise addition of 32% hydrochloric acid, giving 7.5 mL of solution. The active concentration of trivalent arsenic was found to be 17.5 mM (using the same method used to determine the active concentrations of BRAO and GSAO).

EXAMPLE 1(o)

Synthesis of N-(3-(4-arsenosophenylcarbamoylmethylthio)propanoyl)-L-glutamic acid (GluAO)

The procedure used was the same as for N-(3-(4-arsenosophenylcarbamoylmethylthio)-propanoyl)-L-aspartic acid, using 2.63 mL (184 μmol) of 70.0 mM BRAO in DMSO, the disulfide of disodium N-(3-mercaptopropanoyl)-L-glutamate (0.61 g), 0.5 M bicarbonate buffer, pH 9 (10.52 mL, 5.3 mmol), and 0.69 M triphenylphosphine in DMSO (1.7 mL, 1.2 mmol). In this case, DMSO (2 mL) was added to the precipitated mixture before-leaving overnight. The active concentration of trivalent arsenic was found to be 15.4 mM (10.3 mL of solution).

EXAMPLE 1(p)

Synthesis of N-(3-(4-arsenosophenylcarbamoylmethylthio)propanoyl)-L-cysteic acid (Cys*AO)

The procedure used was the same as for N-(3-(4-arsenosophenylcarbamoylmethylthio)propanoyl)-L-glutamic acid, using 2.70 mL (189 μmol) of 70.0 mM BRAO in DMSO, the disulfide of disodium N-(3-mercaptopropanoyl)-L-cysteate (0.68 g), 0.5 M bicarbonate buffer, pH 9 (10.80 mL, 5.4 mmol), and 0.69 M triphenylphosphine in DMSO (1.8 mL, 1.2 mmol). The active concentration of trivalent arsenic was found to be 17.5 mM (12.3 mL of solution).

EXAMPLE 1(q)

Synthesis of N-(3-(4-arsenosophenylcarbamoylmethylthio)propanoyl)-D-glucosamine (GlcAO)

The procedure used was the same as for N-(3-(4-arsenosophenylcarbamoylmethylthio)propanoyl)-L-glutamic acid, using 3.00 mL (210 μmol) of 70.0 mM BRAO in DMSO, the disulfide of disodium N-(3-mercaptopropanoyl)-D-glucosamine (0.67 g), 0.5 M bicarbonate buffer, pH 9 (11.96 mL, 600 mmol), and 0.69 M triphenylphosphine in DMSO (1.9 mL, 1.3 mmol). The active concentration of trivalent arsenic was found to be 13.5 mM (11.0 mL of solution).

EXAMPLE 2

Assay and Reactivity of GSAO

EXAMPLE 2(a)

Assay of BRAO, GSAO and GSAO-B

A stock solution of DMP (5 μL. 50 μmol) was dissolved in DMSO (995 μL), giving a concentration of 50 mM DMP. A second dilution of the 50 mM DMP stock solution (10 μL) in pH 7.0 buffer (0.1 M HEPES, 0.3 M NaCl, 1 mM EDTA) (99 μL) gave a working solution of 500 OM DMP. The activity of the arsenical could then be determined by the titration of varying amounts of arsenical against the DMP working solution (10 μL) in a 96-well microtitre plate, with the total volume made up to 195 μL by addition of buffer. After a 10 minute incubation at room temperature, during which time the solutions were agitated on a plate shaker, 5 μL of a 37.9 mM stock solution of DTNB (15 mg) in DMSO (1 mL) was added, and the plate incubated with shaking for another 10 minutes. The absorbance at 412 nm due to the formation of the TNB dianion was measured using a Molecular Devices Thermomax Plus (Palo Alto, Calif.) microplate reader. The extinction coefficient for the TNB dianion at pH 7.0 is 14,150 $M^{-1}$ $cm^{-1}$ at 412 nm (Riddles et al., 1983).

Figure 11:
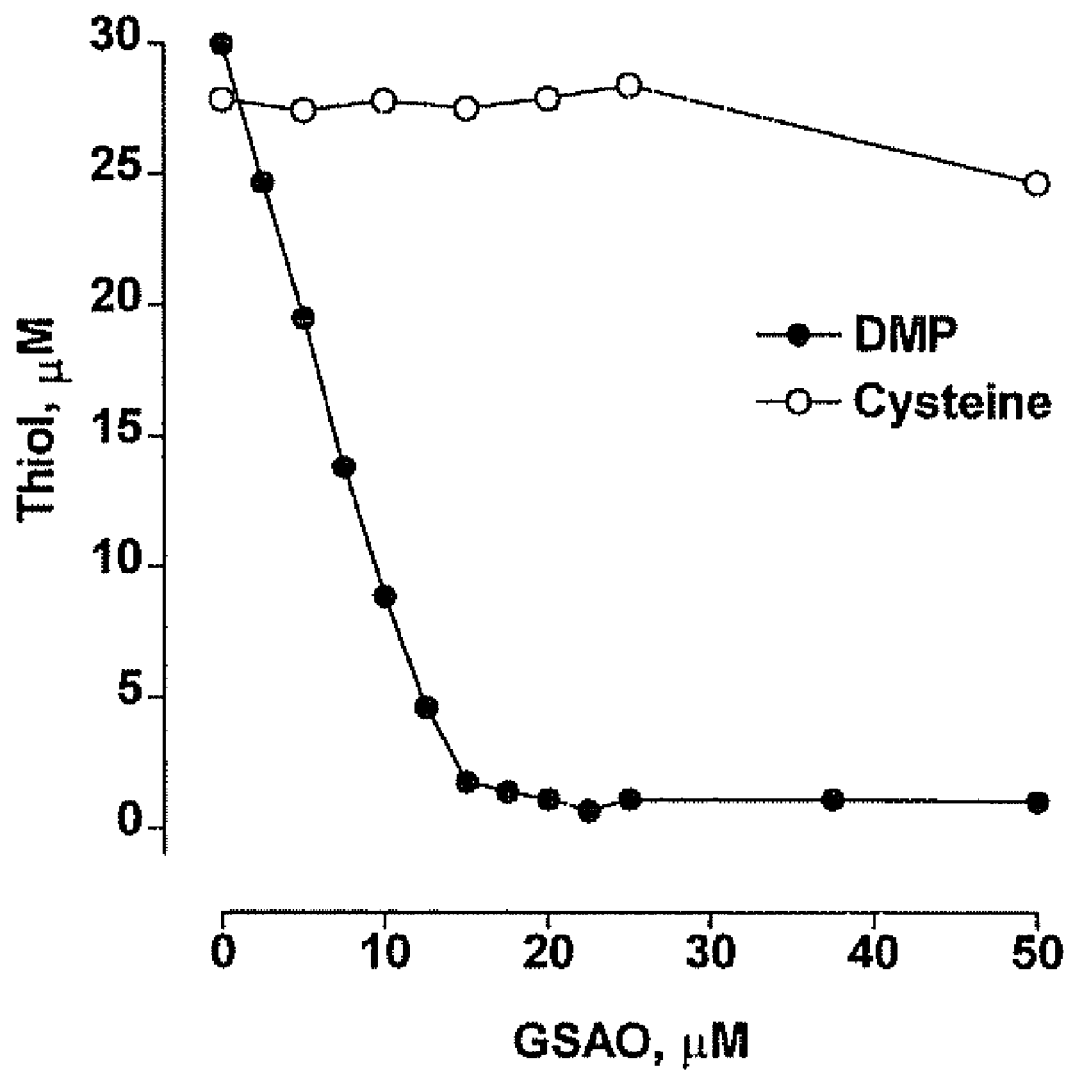
FIG. 11. Titration of DMP or cysteine with GSAO. DMP (15 µM corresponding to 30 µM thiols) or cysteine (28 µM) was incubated with GSAO (0-50 µM) for 10 minutes. DTNB (950 µM) was then added and the reactions incubated for a further 10 minutes. The concentration of thiol in the reactions was determined from the absorbance of the TNB dianion at 412 nm. GSAO bound to DMP and prevented interaction of the dithiol with DTNB while any interaction of GSAO with cysteine was displaced by DTNB.

GSAO bound to DMP and prevented interaction of the dithiol with DTNB while any interaction of GSAO with cysteine was displaced by DTNB (FIG. 11). This result confirmed the dithiol selectivity of GSAO.

EXAMPLE 2(b)

Interaction of GSAO with Synthetic, Peptide and Protein Dithiols

Recombinant human thioredoxin produced in *E. coli* was from American Diagnostica, Greenwich, Conn. The hexapeptides, TrpCysGlyProCysLys and TrpCysGlyHisCysLys, were from Auspep, Parkville, Australia.

Binding of GSAO to dithiols was measured from loss of thiols using the DTNB assay described above. The dissociation constant, $K_d$, for GSAO binding to dithiols was determined by incubating increasing concentrations of GSAO, I, with a fixed dithiol concentration, $[S]_T$, and measuring the remaining dithiol using DTNB. Note that the concentration of dithiol equals half the TNB concentration. The concentration of dithiol.GSAO complex, SI, as a function of the total GSAO concentration, $[I]_T$, is described by Equation 1 (Hogg and Jackson, 1990), $$[SI]=0.5\{([S]_T+x[I]_T+K_d)-(([S]_T+x.[I]_T+K_d)^2-4.[S]_T x.[I]_T)^{0.54}\} \quad (1)$$

where x is a factor that, when multiplied together with $[I]_T$, will yield the active concentration of GSAO. Data was fit to equation 1 by non-linear least squares regression with $K_d$ and x the unknown parameters (Scientist software, Micromath, Salt Lake City, Utah). x was 1±0.2 for all the dithiols tested.

Thioredoxin contains 5 accessible thiols that react with DTNB (Holmgren, 1989). Titration of thioredoxin with GSAO resulted in a decrease from 5 to 3 thiols upon complex formation. The dissociation constant, $K_d$, for GSAO binding to thioredoxin was determined by incubating increasing concentrations of GSAO, I, with a fixed thioredoxin thiol concentration, $[S]_T$, and measuring the remaining thiol groups using DTNB. Note that the concentration of thiol groups equals the TNB concentration. The concentration of thioredoxin thiol-GSAO complex, SI, as a function of the total GSAO concentration, $[I]_T$, is described by Equation 2, $$[S]_T=2.[SI]+2.[S]_D+[S]_M \quad (2a)$$

$$[SI]=0.5.\{([S]_D+x.[I]_D+K_d)-(([S]_D+x.[I]_T+K_d)^2-4.[S]_D x.[I]_T)^{0.5}\} \quad (2b)$$

where $[S]_D$ is the concentration of thioredoxin dithiol that complexes with GSAO and $[S]_M$ is the concentration of the remaining thiol groups. Data was fit to equation 2 by non-linear least squares regression with $K_d$ and x the unknown parameters (Scientist software, Micromath, Salt Lake City, Utah). x was 1.5±0.2 for thioredoxin.

Figure 12:
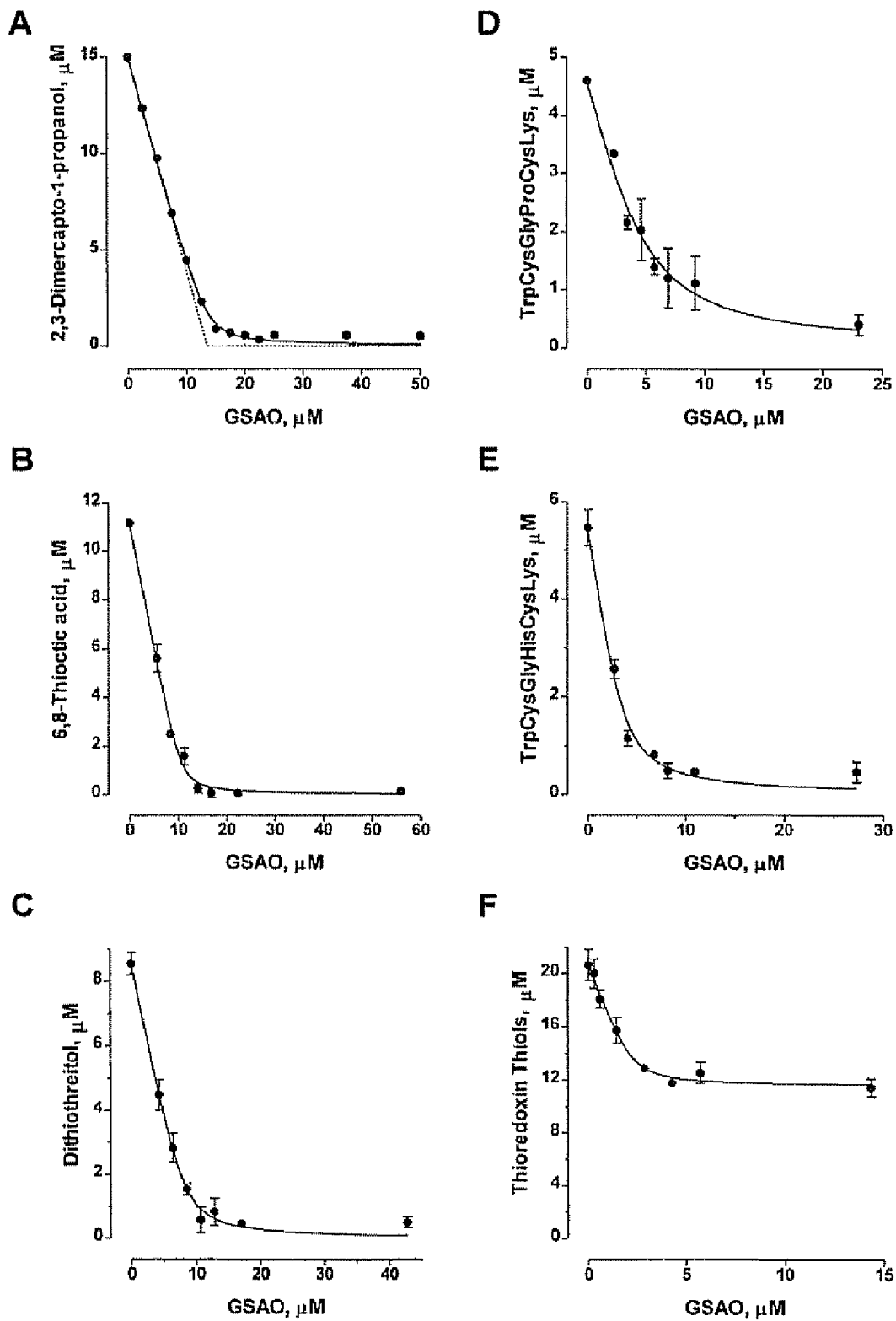
FIG. 12. Interaction of GSAO with synthetic, peptide and protein dithiols. DMP (A) (15 µM), 6,8-thioctic acid (B) (11 M), dithiothreitol (C) (8.5 µM), TrpCysGlyProCysLys (D) (4.6 µM), TrpCysGlyHisCysLys (E) (5.5 µM) or thioredoxin (F) (41 µM corresponding to 20.6 µM thiols) was incubated with GSAO (0-56 µM) for 10 minutes. DTNB (950 µM) was then added and the reactions incubated for a further 10 minutes. The concentration of thiol in the reactions was determined from the absorbance of the TNB dianion at 412 nm. The solid lines represent the best non-linear least squares fit of the data to Equation 1 (A to E) or Equation 2 (F) and have been drawn using the parameter estimates in Table 1. The dotted line in part A represents a simulated titration assuming an infinite affinity of GSAO for the dithiol. GSAO bound to both synthetic, peptide and protein dithiols with dissociation constants in the range 130 nM to 1.4 µM.

The small synthetic dithiols, DMP, 6,8-thioctic acid and dithiothreitol, formed high affinity complexes with GSAO (FIGS. 12A, B and C, Table 1). The affinity for GSAO decreased as the size of the ring structure with the arsenic of GSAO increased. For instance, the two thiols of DMP are on adjacent carbon atoms which form a five-membered ring with the GSAO arsenic. The affinity of GSAO for the dithiols decreased from a dissociation constant of 130 nM for a five membered ring with DMP to 420 nM for a seven-membered ring with dithiothreitol.

GSAO also bound with high affinity to both peptide and protein dithiols. The two peptides, TrpoysGlyProCysLys (Holmgren, 1989) and TrpCysGlyHisCysLys (Gilbert, 1997), correspond to the active site sequences of thioredoxin and PDI, respectively. Both peptides bound GSAO with dissociation constants of approximately 1 ☐M (FIGS. 12D and E, Table 1). There were 15 atoms in the ring structure of the peptides with the arsenic of GSAO. Despite this large ring structure the dissociation constant for binding of GSAO was only double that for binding of GSAO to dithiothreitol. This result implied that the secondary structure of the peptides brought the two Cys thiols into close proximity which enabled them to complex with the trivalent arsenical, GSAO bound to the active site dithiol of thioredoxin with a dissociation constant of 370±180 nM (FIG. 12F, Table 1), which was ~4-fold higher affinity than that of GSAO binding to the thioredoxin active site hexapeptide, 1,420±450 nM. This result implied that the distance between the active site thiols in thioredoxin was closer than their distance in the hexapeptide.

Considered together, these results indicated that GSAO selectively binds proteins containing closely spaced thiols. To identify these proteins on the cell surface a biotin moiety was attached through a spacer arm to the primary amino group of the □-glutamyl residue of GSAO. Incorporation of GSAO-B into proteins could be assessed by measuring the biotin using streptavidin-peroxidase.

TABLE 1

Dissociation constants for binding of GSAO to synthetic and protein dithiols.

| Dithiol | Ring Size[a] | Dissociation Constant, nM |
|---|---|---|
| 2,3-Dimercapto-1-propanol | 5 | 130 ± 40[b] |
| 6,8-Thioctic acid | 6 | 200 ± 50 |
| Dithiothreitol | 7 | 420 ± 80 |
| TrpCysGlyProCysLys | 15 | 1,420 ± 450 |
| TrpCysGlyHisCysLys | 15 | 870 ± 270 |
| Thioredoxin | 15 | 370 ± 180 |

[a] number of atoms in the ring structure with the arsenic of GSAO.
[b] errors are 1 SD.

EXAMPLE 2(c)

Inhibition of Thioredoxin Activity by GSAO

Figure 13:
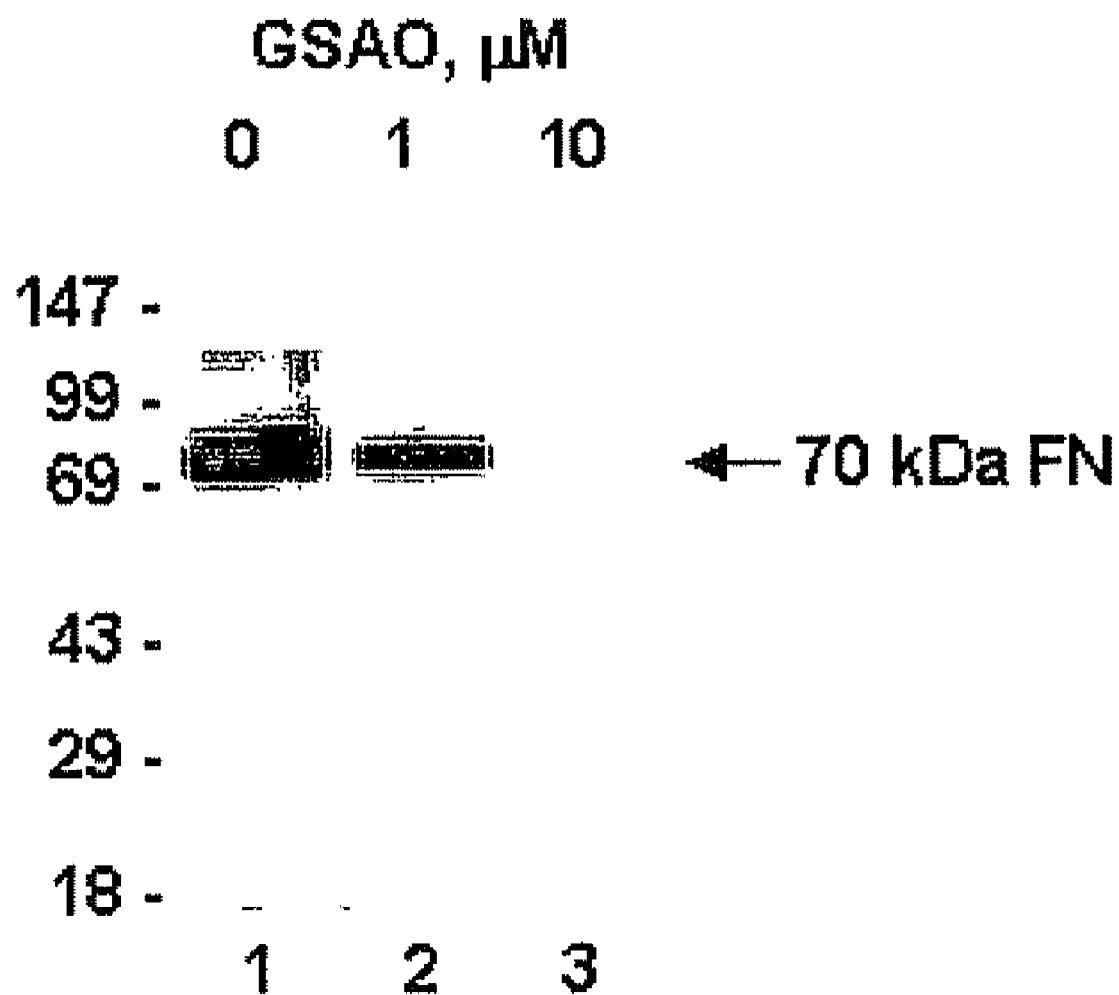
FIG. 13. Inhibition of thioredoxin by GSAO. Thioredoxin (1 µM) was incubated with GSAO (0, 1 or 10 µM) for 10 minutes at room temperature in 20 mM Hepes, 0.14 M NaCl, pH 7.4 buffer. The 70 kDa fibronectin fragment (10 µg per mL) was added and incubated for 5 minutes at room temperature. The reactions were labelled with MPB (100 µM) for 10 minutes at 37° C. The MPB was quenched with GSH (200 µM) for 10 minutes at 37° C. followed by iodoacetamide (400 µM) for 10 minutes at room temperature. The MPB-labelled 70 kDa fragment was resolved on 5-15% SDS-PAGE, transferred to PVDF membrane and the MPB detected by blotting with streptavidin peroxidase. The positions of Mr markers are shown at left.

It was observed that thioredoxin reduced one or more protein disulfide bonds in the 70 kDa N-terminal fragment of fibronectin. Incubation of 1 μM GSAO with 1 μM thioredoxin for 10 minutes in Hepes buffered saline resulted in ~50% inhibition of thioredoxin-mediated reduction of the fibronectin fragment, whereas incubation with 10 μM GSAO completely inhibited thioredoxin activity (FIG. 13).

EXAMPLE 2(d)

Interaction of GSAO-B with PDI and Thioredoxin

Figure 14:
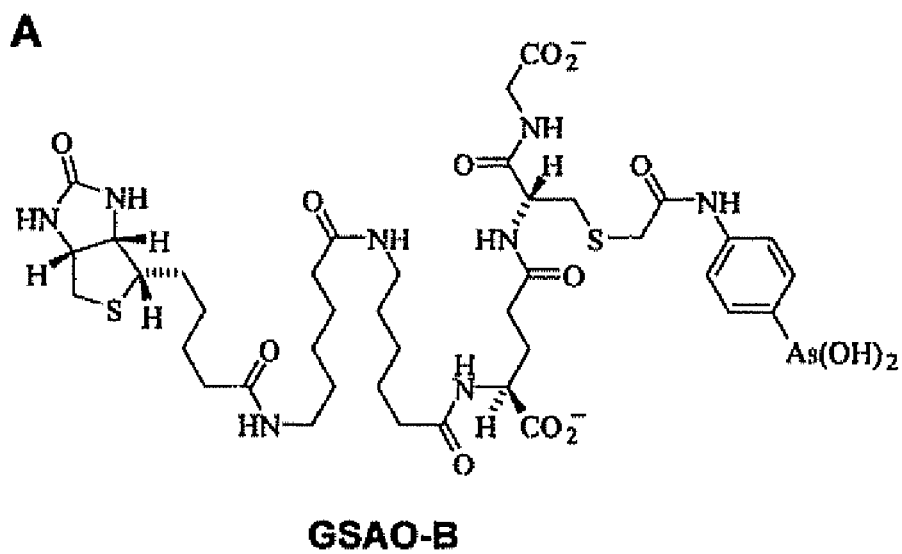
FIG. 14. Interaction of GSAO-B with PDI and thioredoxin. A Structure of GSAO-B. B Purified human recombinant PDI (5 µM), human recombinant thioredoxin (5 µM) or bovine serum albumin (5 ﬞM) was incubated with dithioihreitol (10 µM) for 60 minutes at room temperature to ensure that the active site disulfide(s) of PDI and thioredoxin were in the reduced dithiol form. GSAO-B (100 ﬞM) or GSAO-B and OMP (400 µM) was then added and the reactions incubated for 30 minutes at room temperature. The labelled PDI (lanes 1 and 2), thioredoxin (lanes 3 and 4) and albumin (lane 5) (75 pmoles) was resolved on 4-16% SDS-PAGE, transferred to PVDF membrane, and blotted with streptavidin-peroxidase to detect the GSAO-B label. The positions of M$_r$ markers are shown at left.
Figure 14:
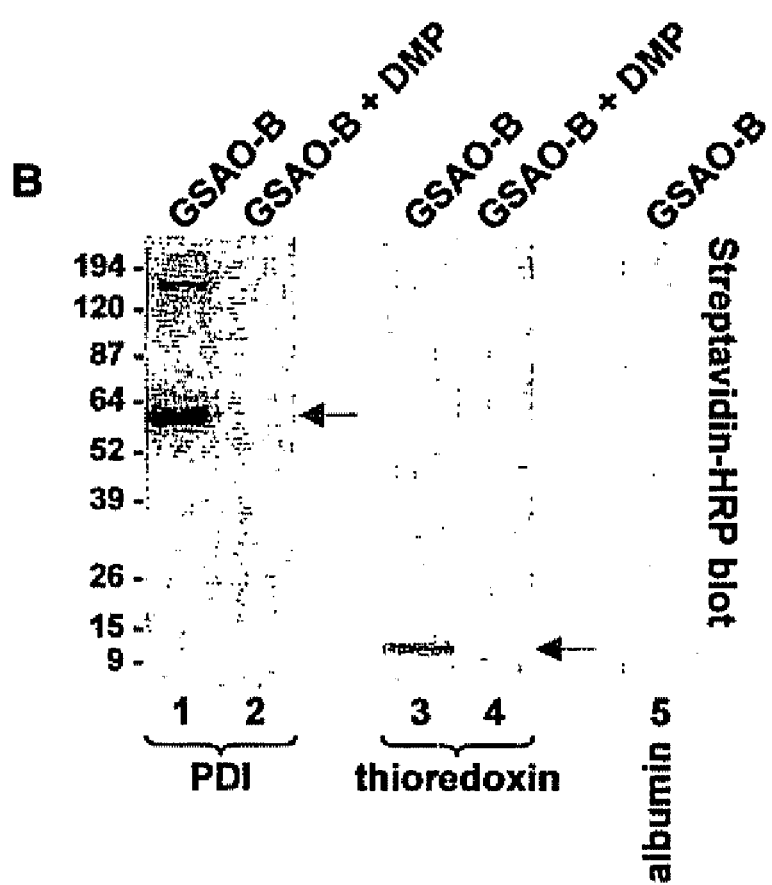

Human recombinant PDI and thioredoxin bound GSAO-B (FIG. 14). Recombinant human protein disulfide isomerase (PDI) was produced in *E. coli* and purified according to Jiang et al. (1999). In the experiment, purified PDI, thioredoxin or albumin as negative control were incubated with a 2-fold molar excess of dithiothreitol for 60 minutes to ensure that the active site disulfides of PDI and thioredoxin were in the reduced dithiol state. The proteins were then incubated with GSAO-B or GSAO-B and a 4-fold molar excess of DMP for 30 minutes. Equivalent moles of the labeled proteins were resolved on SDS-PAGE, transferred to PVDF membrane, and blotted with streptavidin-peroxidase to detect the GSAO-B label. Samples were resolved on 4-15% SDS-PAGE under non-reducing conditions (Laemmli, 1970) and transferred to PVDF membrane. Proteins were detected by Western blot using an anti-PDI murine monoclonal antibody (Jiang et al., 1999) (used at 2 μg per mL). Rabbit anti-mouse horseradish peroxidase conjugated antibodies (Dako Corporation, Carpinteria, Calif.) were used at 1:2000 dilution. GSAO-B-labeled proteins were blotted with streptavidin peroxidase (Amersham, Sydney, NSW) used at 1:1000 dilution. Proteins were visualised using chemiluminescence (DuPont NEN, Boston, Mass.) according to the manufacturer's instructions Chemiluminescence films were analysed using a GS-700 Imaging Densitometer and Multi-Analyst software (Bio-Rad, Hercules, Calif.), Both PDI and thioredoxin incorporated GSAO-B but albumin did not. The higher M, band in lane 1 of FIG. 14B was a small amount of aggregated PDI in the preparation (Jiang et al., 1999). It is noteworthy that the density of labeling of PDI was approximately twice that of thioredoxin which is consistent with the two active site dithiols of PDI versus the one of thioredoxin.

EXAMPLE 2(e)

Comparison of the Effects of Hydrophobic, Hydrophilic or Charged Trivalent arsenicals on Endothelial Cell Viability Bovine aortic endothelial (BAE) cells (Hotchkiss et al., 1998) were seeded in wells of 96 well plates overnight, washed and then incubated with complete medium containing increasing concentrations of either the membrane permeable PAO, or the substantially membrane-impermeable GSAO, AspAO, GluAO Cys*AO, GlcAO or FXAO. After 24 hours incubation the adherent cells were counted.

Figure 15:
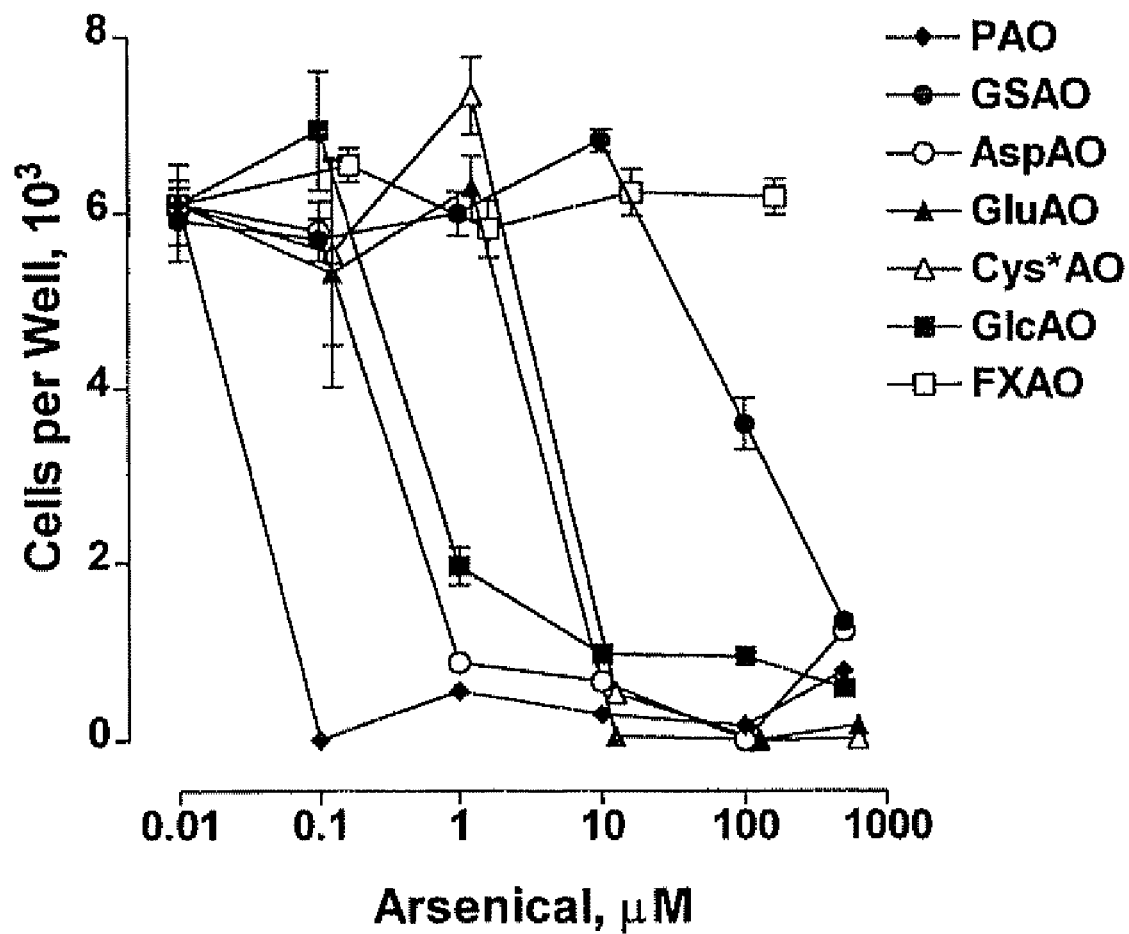
FIG. 15. Comparison of the cytotoxic effects of a membrane permeable versus substantially membrane-impermeable trivalent arsenicals. BAE cells (5×10$^3$ cells) were seeded in wells of 96 well plates and allowed to attach for 24 hours at 37° C. and 5% CO$_2$. The cells, which were ~80% confluent, were washed two times with PBS and incubated with 100 µl of complete medium containing increasing concentrations of either PAO, GSAO, AspAO, GluAO, Cys*AO, GlcAO or FXAO (0 to 0.6 mM) for 24 hours at 37° C. and 5% CO$_2$. The cells were then washed two times with PBS to remove non-adherent cells and adherent cells were counted using methylene blue as described by Oliver et al, (1989). The data points are the mean and SE of triplicate wells.

PAO was very toxic for BAE cells with an $IC_{50}$ for viability of <0.1 μM (FIG. 15). The viability $IC_{50}$'S for GSAO, AspAO, GluAO, Cys*AO, GlcAO and FXAO were ~100 μM, <1 μM, <10 μM, <10 μM, <1 μM and >200 μM, respectively (FIG. 15). GSAA had no significant effect on BAE viability up to 10 mM concentration (not shown). This result demonstrated that limiting the entry of the trivalent arsenical into the cell by attaching it to charged (GSH, Asp, Glu, cysteic acid) or hydrophilic (glucosamine, fluorescein-X) pendants reduced toxicity by 10- to >2,000-fold.

EXAMPLE 2(f)

GSAO is Substantially Membrane-impermeable

GSAO does not cross the plasma membrane to any significant extent. Human T cells (A3.01) or adherent BAE cells were incubated with complete medium containing 50 μM GSAO and ~100,000 counts per, minute of triflated GSAO for 1 or 72 hours. Tritiated GSAO was prepared exactly as described for GSAO except that glycine-2-$^3$H-glutathione (NEN, Boston, Mass.) was used in place of cold glutathione. The cells were washed and lysed by two cycles of freezing and thawing. The cytosolic constituents were collected by differential centrifugation (Ausbel et al., 2000) and the tritiated GSAO was measured. Only 0.5% of the total tritiated GSAO was found in the T cell cytosol and 0.04% in the BAE cytosol after 1 hour. Moreover, only 4.5% of the GSAO penetrated the T cell membrane after 72 hours of culture.

EXAMPLE 3

Effect of GSAO on Angiogenesis

EXAMPLE 3(a)

Identification of Endothelial Cell Surface Proteins that Contain Closely Spaced Dithiol(s)

Human umbilical vein endothelial cells (HUVEC) (Wall et al., 1978) and the human dermal microvascular endothelial cell line, HMEC-1 (Ades et al., 1992), were harvested and cultured as indicated. Endothelial cells ($5 \times 10^6$) were detached from culture flasks using 5 mM EDTA in PBS at 37° C., washed 3 times with PBS, resuspended in PBS containing 100 μM of GSAO-B in the absence or presence of 400 μM DMP, and incubated for 30 minutes at room temperature. The cells were washed 3 times with 1 mL of PBS, resuspended in 0.2 mL of ice cold 50 mM Tris/HCl, pH 8 buffer containing 0.5 M NaC, 1% Triton X-100, 10 µM leupeptin, 2 mM PMSF (Sigma Chemical Company, St, Louis, Mo.), 5 mM EDTA and 10 µM aprotinin (Bayer Australia Ltd., Sydney, NSW), and sonicated on ice. On some occasions the cell lysates were incubated with streptavidin-agarose (Sigma, Castle Hill, NSW) beads (25 µL of packed beads in a total volume of 1 mL) for 60 minutes at 4° C. with rotary mixing. Bound proteins were washed 5 times with 50 mM Tris/HCl, pH 8 buffer containing 0.15 M NaCl and 0.05% Triton X-100, resolved on SDS-PAGE, transferred to PVDF membrane, and the GSAO-B-labeled proteins detected by Western blot.

There were approximately ten proteins on the endothelial cell surface that incorporated GSAO-B (FIG. 16A). The molecular masses of these proteins varied from 12 to 138 kDa (FIG. 16B). The intensity of labeling of the proteins varied considerably which probably reflected their abundance on the cell surface, although it may also have reflected differences in the affinity of GSAO for the protein dithiols. The labeling was specific as there was effectively no incorporation of GSAO-B in the presence of DMP.

EXAMPLE 3(b)

PDI Was One of the GSAO-B Labeled Proteins on the Endothelial Cell Surface

BAE cells were labeled with GSAO-B in the absence or presence of DMP, lysed and incubated with streptavidin-agarose beads to collect the biotin-labeled proteins. The labeled proteins were eluted from the beads, resolved on SDS-PAGE, transferred to PVDF membrane, and blotted with anti-PDI polyclonal antibodies.

Figure 17:
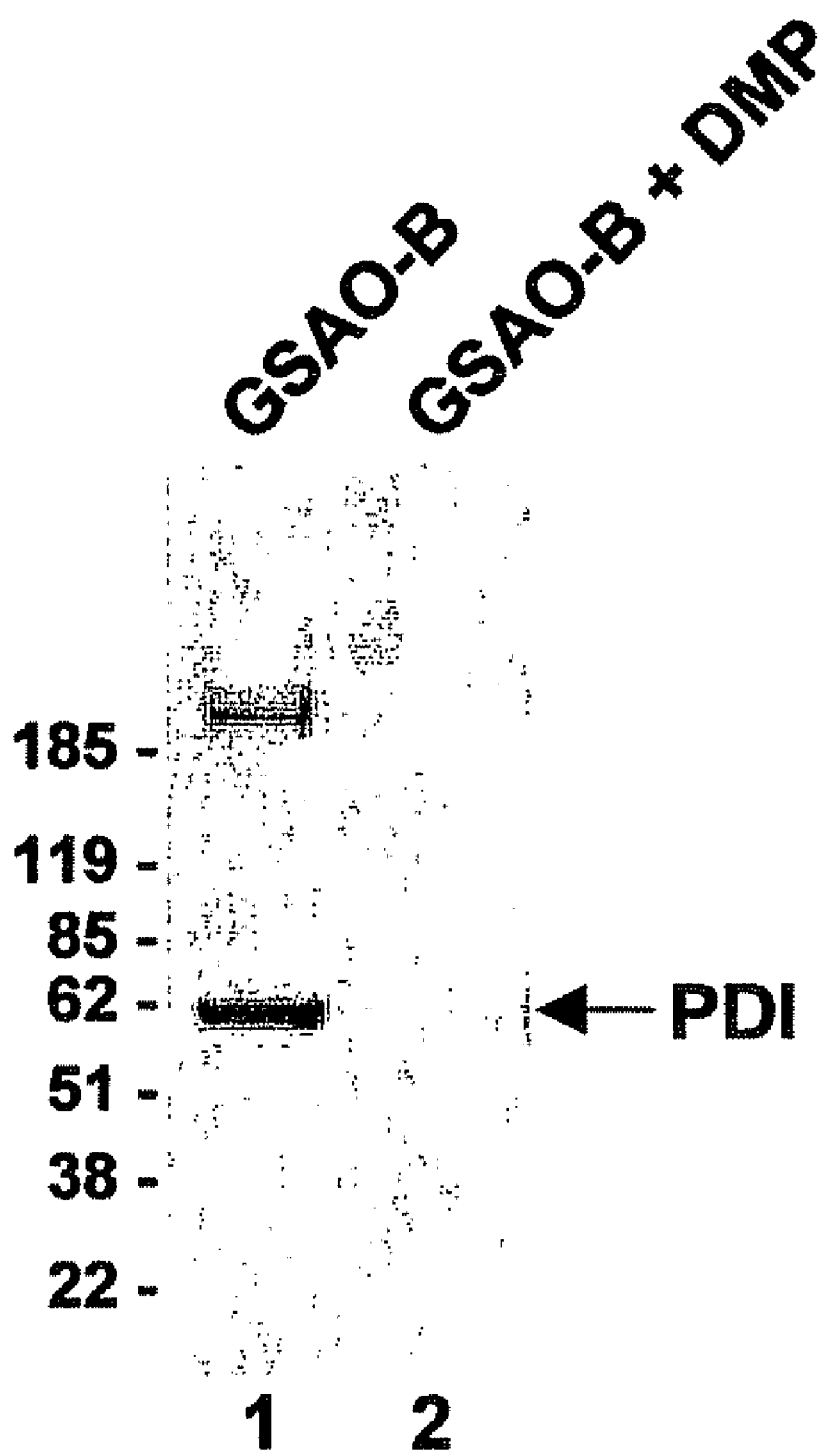
FIG. 17. PDI was one of the GSAO-B labelled proteins on the endothelial cell surface. HUVEC (5×10$^6$ cells in 0.75 mL) were labelled with GSAO-B (100 µM) for 30 minutes at 37° C. in the absence (lanes 1) or presence of DMP (400 µM) (lane 2). The cells were lysed and incubated with streptavidin-agarose beads to collect the biotin-labelled proteins. The labelled proteins were resolved on 4-15% SDS-PAGE, transferred to PVDF membrane, and blotted with anti-PDI monoclonal antibodies. The results represent labelling of 5×10$^6$ endothelial cells. The positions of M$_r$ markers are shown at left.

The results shown in FIG. 17 indicate that PDI was one of the proteins on the endothelial cell surface that incorporated GSAO-B. There was no labeling of PDI in the presence of DMP which is supported by the results of FIG. 14. The higher $M_r$ band in lane 1 of FIG. 17 was some aggregated PDI (see FIG. 14B).

EXAMPLE 3(c)

Inhibition of Proliferation of Endothelial Cells by GSAO

BCE (Folkman et al. 1979), BAE, BxPC-3 (ATCC, Bethesda, Md.), HT1080 (Jiang et al., 1999), 3T3 (ATCC, Bethesda, Md.) and BVSM (Hogg et al., 1997) cells were harvested and cultured as indicated. Cells (0.5 ml of 30,000 or 100,000 cells per mL) were seeded into gelatinized 24-well culture plates (Coming Costar, Corning, N.Y.) in Dulbecco's Modified Eagle's Medium (DMEM, JHR Bioscience, Lenexa, Kans.) containing 10% fetal calf serum (FCS, Intergen Comp., Purchase, N.Y.) and 1% Glutamine Pen-Strep (GPS, Irvine Scientific, Santa Ana, Va.) and allowed to attach for 24 hr in 10% $CO_2$ at 37° C. The media was then replaced with DMEM and 1% GPS containing 0 to 1 mM GSAO or GSM and either 5% bovine calf serum (BCS, HyClone, Logan, Utah) and 1 ng per mL FGF-2 (Genzyme, Cambridge, Mass.) or 5% BCS and 10 ng per mL VEGF (Genzyme, Cambridge, Mass.) for BCE cells, 5% or 10% BCS for BAE cells, 5% BCS for BVSM cells, and 5% FCS for BxPC-3, HT1080 and 3T3 cells. Cells were cultured for 0 to 72 hr in 10% $CO_2$ at 37° C. then dispersed in trypsin/EDTA (GibcoBRL, Granc Island, N.Y.), resuspended in Coulter balanced electrolyte solution and counted with a Z1 Coulter counter (Coulter Corp., Miami, Fla.). In all experiments there were two control wells containing DMEM with 1% GPS and either 5% BCS for BCE cells, 2% BCS for BAE and BVSM cells, or 2% FCS for BxPC3, HT1080 and 3T3 cells. These wells represented no to limited proliferation.

Figure 18:
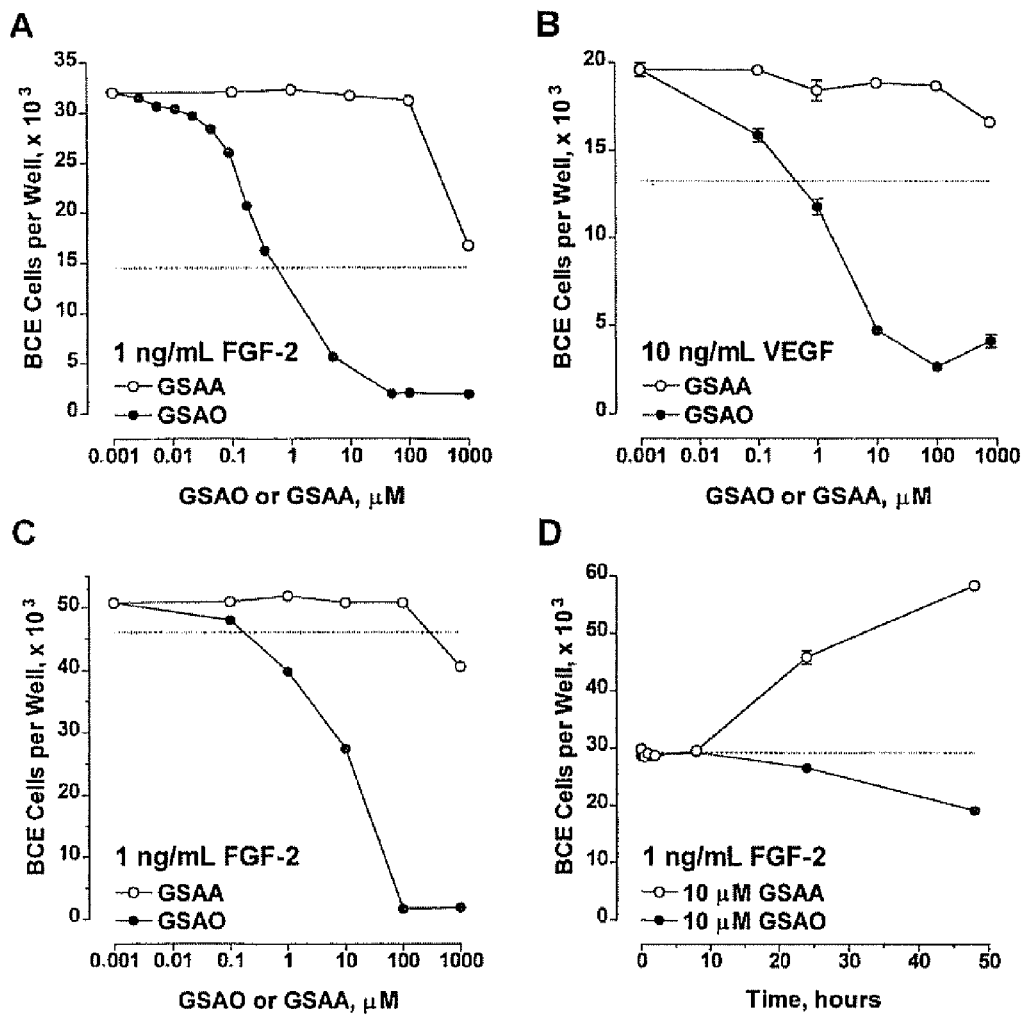
FIG. 18. Inhibition of proliferation and reduction in viability of BCE cells by GSAO. 15,000 (part A and B) or 50,000 (part C and D) BCE cells per well were seeded into gelatinised 24-well culture plates and allowed to attach for 24 hr (part A, B and D) or 72 hr (part C). The media was then replaced with DMEM containing 5% BCS and 0 to 1 mM GSAO or GSAA and either 1 ng per mL FGF-2 (part A) or 10 ng per mL VEGF (part B). In part D, the media was replaced with DMEM containing 5% BCS and 1 ng per mL FGF-2 and either 10 µM GSAO or GSM. In part C, the media was replaced with DMEM containing 5% BCS and 0 to 1 mM GSAO or GSAA. Cells were cultured for 72 hr in parts A, B and C or for discrete times up to 48 hr in part D and then dispersed and counted. The dotted line in parts A, B and C indicate the cell number in control wells containing DMEM and 5% BCS which represented no to limited proliferation. The dotted line in part D represents no change in cell number over the 48 hr. The data points and errors represent the mean and range of duplicate wells.

GSAO inhibited the proliferation and reduced the viability of BCE cells in culture (FIG. 18). In contrast, GSAA had only a marginal effect on proliferation at the highest concentration used, 1 mM, and no significant effect on viability. Inhibition of proliferation by GSAO was independent of whether the cells were stimulated with either fibroblast growth factor-2 (FGF-2) (FIG. 18A) or vascular endothelial cell growth factor (VEGF) (FIG. 18B). The $IC_{50}$ for inhibition of proliferation in response to FGF-2 or VEGF was ~0.1 µM and ~0.05 µM, respectively (Table 2). GSAO also reduced the viability of BCE cells with $IC_{50}$'s of ~10 µM and ~3 µM in the presence of FGF-2 or VEGF, respectively (Table 2). The anti-proliferative versus viability effects of GSAO were separated by measuring viability of confluent cultures of cells. For example, FIG. 18C shows the is effects of GSAO on the viability of a near confluent culture of BCE cells. In this experiment there was <10% increase in cell number after 72 hr of culture. The time dependence of the effect of GSAO on proliferation and viability of BCE cells is shown in FIG. 18D. A concentration of 10 OM GSAO was chosen as this was the $IC_{50}$ for decrease in viability (Table 2). There was no decrease in viability after 8 hours. The cell number declined thereafter.

GSAO also inhibited proliferation and reduced viability of BAE cells (not shown). GSAA did not effect either proliferation or viability. The $IC_{50}$ values for inhibition of proliferation and reduction in viability by GSAO were in the same range as for BCE cells (Table 2). It is noteworthy that the $IC_{50}$ for inhibition of proliferation of BAE cells was ~0.02 µM when 5% FCS was the mitogen versus ~0.2 OM when 10% FCS was used.

Figure 19:
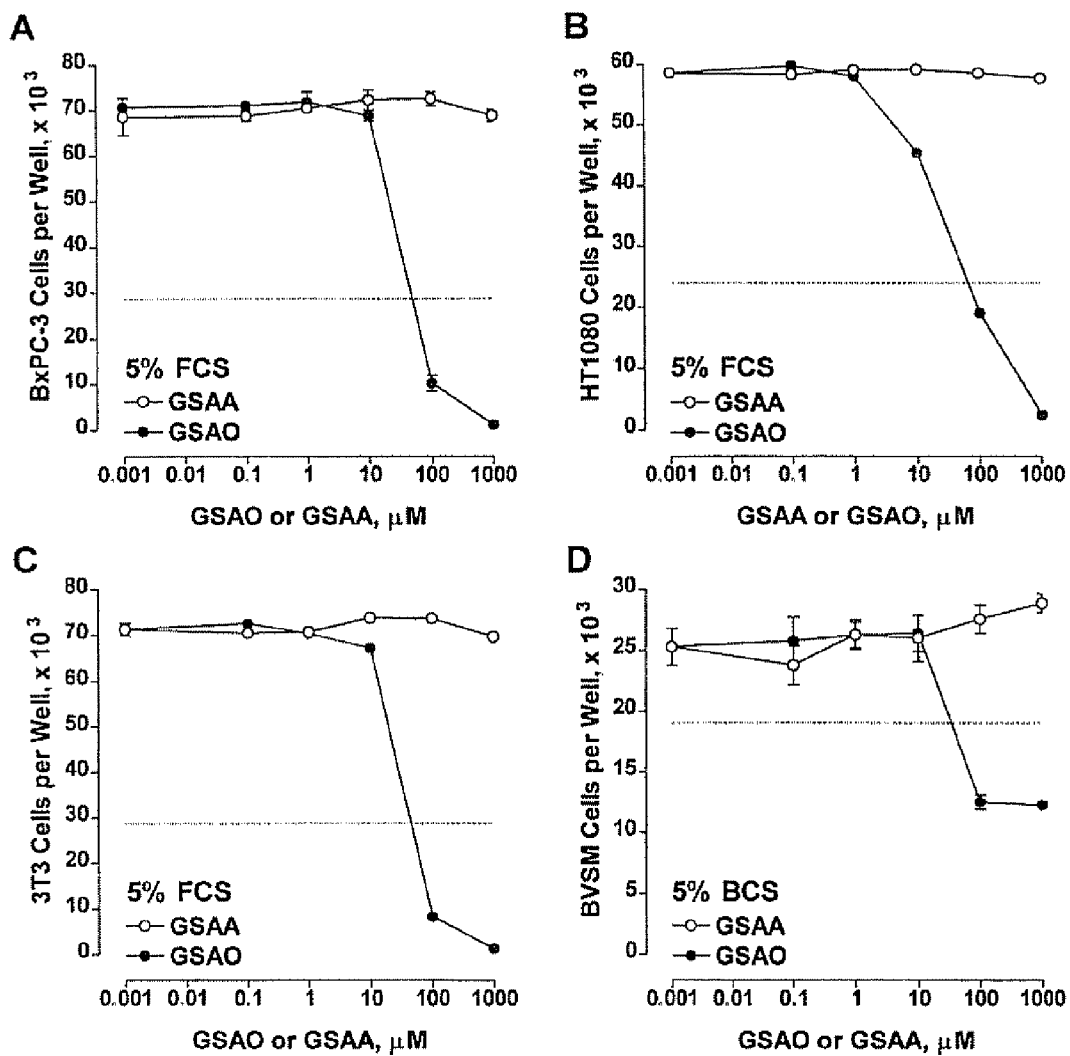
FIG. 19. Effect of GSAO on proliferation of non-endothelial cells. 15,000 BxPC-3 (part A), HT1080 (part B), 3T3 (part C) or BVSM (part D) cells per well were seeded into gelatinised 24-well culture plates and allowed to attach for 24 hr. The media was then replaced with DMEM containing 0 to 1 mM GSAO or GSM and either 5% BCS (part D) or 5% FCS (parts A, B and C). Cells were cultured for 72 hr and then dispersed and counted. The dotted lines indicate the cell number in control wells containing DMEM and 2% BCS (part D) or 2% FCS (parts A, B and C) which represented no to limited proliferation. The data points and errors represent the mean and range of duplicate wells.

GSAO did not affect the proliferation of the human cancer cell lines, BxPC-3 or HT1080, nor murine 3T3 fibroblasts or bovine vascular smooth muscle (BVSM) cells (FIG. 19). GSAO did affect the viability of all these cells with an $IC_{50}$ of ~40 µM (Table 2). This value was 4-13 times higher than the $IC_{50}$'s for reduction in viability of endothelial cells. GSAA had no significant effect on proliferation or viability of these cells up to a concentration of 1 mM.

TABLE 2

Effects of GSAO on proliferation and viability of cultured cells

| Cell | Mitogen | Proliferation $IC_{50}$, µM[a] | Viability $IC_{50}$, µM[b] |
|---|---|---|---|
| BCE | 5% BCS + 1 ng/mL FGF-2 | ~0.1 | ~10 |
| BCE | 5% BCS + 10 ng/mL VEGF | ~0.05 | ~3 |
| BAE | 5% BCS | ~0.02 | ~8 |
| BAE | 10% BCS | ~0.2 | ~10 |
| BxPc3 | 5% FCS | No effect | ~40 |
| HT1080 | 5% FCS | No effect | ~40 |
| BVSM | 5% BCS | No effect | ~40 |
| 3T3 | 5% FCS | No effect | ~40 |

[a]The $IC_{50}$ for inhibition of proliferation of BCE and BAE cells was calculated as the concentration of GSAO that reduced the extent of proliferation by half from the cell number in the absence or GSAO to the cell number in wells containing 5% BCS for BAE cells and 2% BCS for BAE cells in a 72 hr incubation (dotted lines in FIG. 18).
[b]The $IC_{50}$ for reduction in viability of BCE and BAE cells was calculated as the concentration of GSAO that reduced the cell number by half in assays where cells were >90% confluent at the beginning of the 72 hr incubation (for example, see FIG. 18C). The $IC_{50}$ for reduction in viability of all other cells was calculated as the concentration of GSAO that reduced the cell number by half in a 72 hr incubation.

Figure 20:
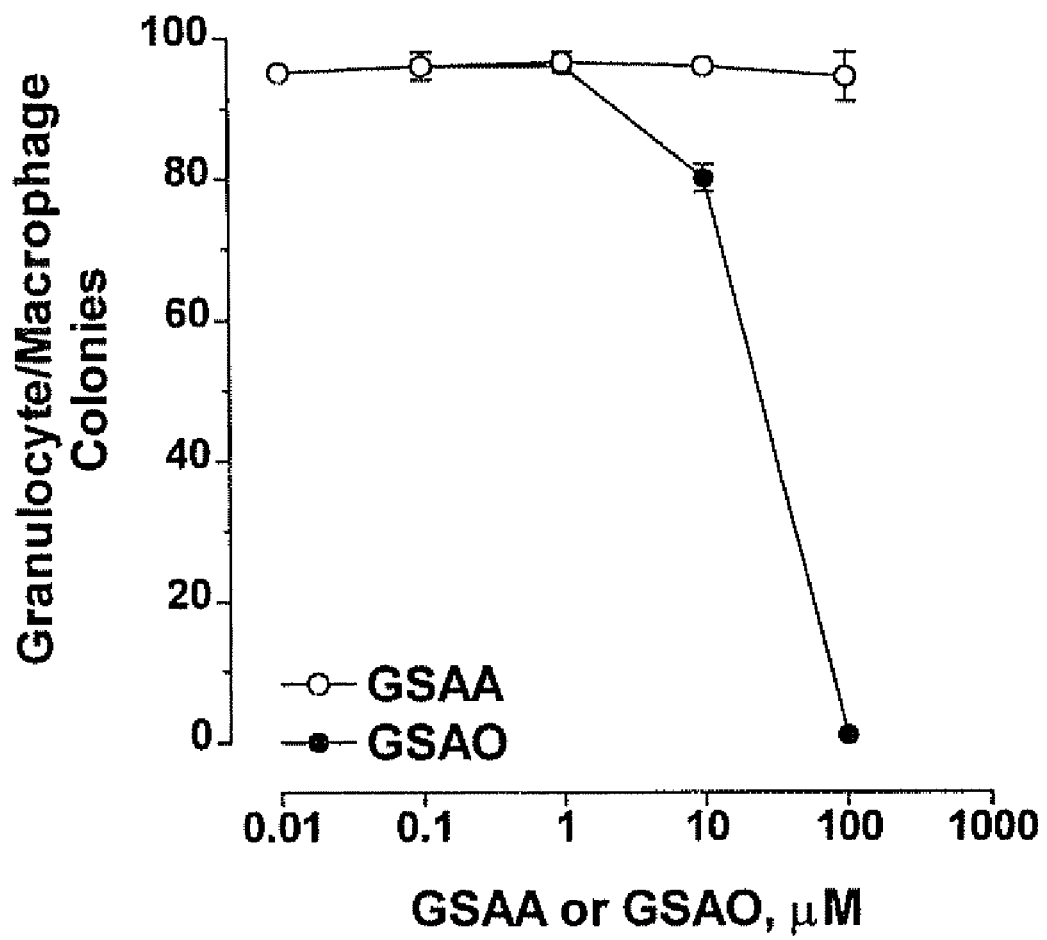
FIG. 20. Effect of GSAO on proliferation of bone marrow progenitor cells. Human bone marrow cells were incubated in semi-solid agar containing 20% BGS, 1 ng per mL IL-3 and 0 to 100 µM GSAA or GSAO for 12 days. Granulocyte/macrophage colonies of 40 or more cells were counted under an inverted microscope. The data points and errors represent the mean and SE of quadruplicate cultures.

GSAO reduced the number of granulocyte/macrophage colonies in a 12 day human bone marrow culture assay with an $IC_{50}$ of ~30 µM (FIG. 20). GSAA had no effect on colony numbers up to a concentration of 100 µM. Human bone marrow cells (~5×10⁵ cells per mL) were added to semi-solid agar in DMEM containing 20% BCS, 5 ng per mL IL-3 and 0 to 100 µM GSAA or GSAO. The cultures were incubated for 12 days at 37° C. and 5% $CO_2$ and clusters of 40 or more cells were counted under an inverted microscope according to Metcalf (1977).

These findings indicated that GSAO was a selective inhibitor of proliferating microvascular and macrovascular endothelial cells. The inhibitory effects were independent of whether the mitogen was either FGF-2 or VEGF GSAO also reduced the viability of endothelial cells in culture in a time dependent manner. The half-maximal effects on viability were at least 4-times smaller than the effects on viability of other primary or transformed cells.

EXAMPLE 3(d)

Inhibition of Endothelial Cell Tube Formation by GSAO

Endothelial cells arrange into tube-like structures when seeded onto three-dimensional matrices such as the extracellular matrix preparation, Matrigel, or collagen. The tubes can be considered to represent immature blood vessels. Matrigel (100 µl, Becton Dickinson, Bedford, Mass.) was added to wells of 96 well plates (Gibco BRL, Gaithersburg, Md.) and allowed to gel for 60 minutes at 37° C. Human dermal microvascular endothelial (HDMVE) cells were harvested and cultured as described by Stathakis et al (1997), HDMVE cells (8,000 cells per well) in 150 µl of M199 (Gibco BRL, Gaithersburg, Md.) media containing 30% pooled human serum, 50 µg per mL Heparin (Sigma, St. Louis, Mo.), 100 µg per mL Endothelial Cell Growth Supplement (Gibco BRL, Gaithersburg, Md.) and 0.1, 1 or 100 µM GSM or GSAO were seeded onto the Matrigel and the plates were incubated for 18 hours in 5% $CO_2$, 37° C. Phase contrast micrographs of the wells were collected.

Figure 21:
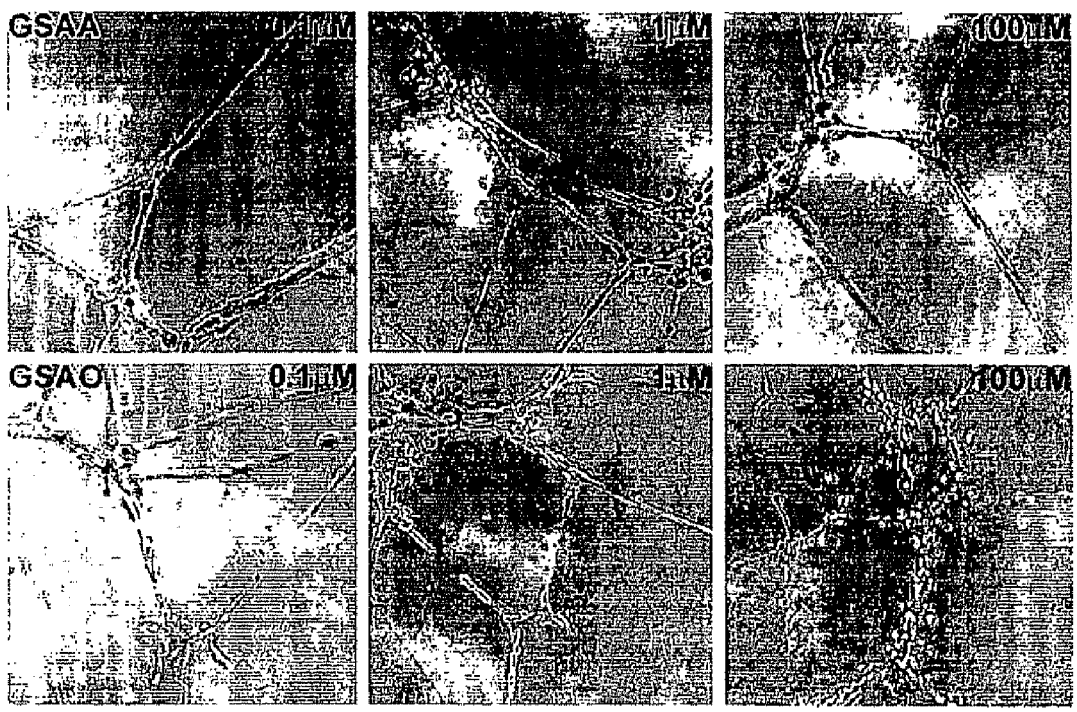
FIG. 21. GSAO perturbs endothelial cell tube formation in Matrigel. Matrigel (100 μl) was added to wells of 96 well plates and allowed to gel for 60 minutes at 37° C. HDMVE cells (10,000 cells per well) in complete media containing 0.1, 1 or 100 μM GSM or GSAO were seeded onto the Matrigel and the plates were incubated in 5% $CO_2$, 37° C. The phase contrast micrographs were taken after 18 hours incubation. GSAO perturbed tube formation by HDMVE cells in Matrigel (bottom panel). Effects were apparent at 0.1 μM concentration and marked at 100 μM. GSAA at the same concentrations had no apparent effect on tube formation (top panel).

GSAO perturbed tube formation by HDMVE cells in Matrigel (FIG. 21). Effects were apparent at 0.1 µM concentration and marked at 100 µM, GSM at the same concentrations had no apparent effect on tube formation.

EXAMPLE 3(e)

Inhibition of Chick Chorioallantoic Membrane (CAM) Angiogenesis by GSAO

The chick CAM assay has been used for the detection and analysis of angiogenesis inhibition (Nguyen et al., 1994). Fertilised 3 day-old white Leghorn eggs (Spafas, Norwich, Conn.) were cracked, the embryos with intact yolks placed in 20×100 mm petri dishes and incubated for 3 days at 37° C. and 3% $CO_2$ (Folkman, 1995). Methylcellulose (Fisher Scientific, Fair Lawn, N.J.) discs containing 5, 10 or 50 µg of either GSAA or GSAO were then applied to the CAM of individual embryos and incubated for 48 hr at 37° C. and 3% $CO_2$. The discs were made by desiccation of GSM or GSAO in 10 µl of 0.45% methylcellulose on teflon rods. The CAMs were observed using a stereomicroscope and scored for no obvious effect or inhibition of CAM angiogenesis as defined by avascular zones. On some occasions CAM blood vessels were injected with India ink and photographed.

Figure 22:
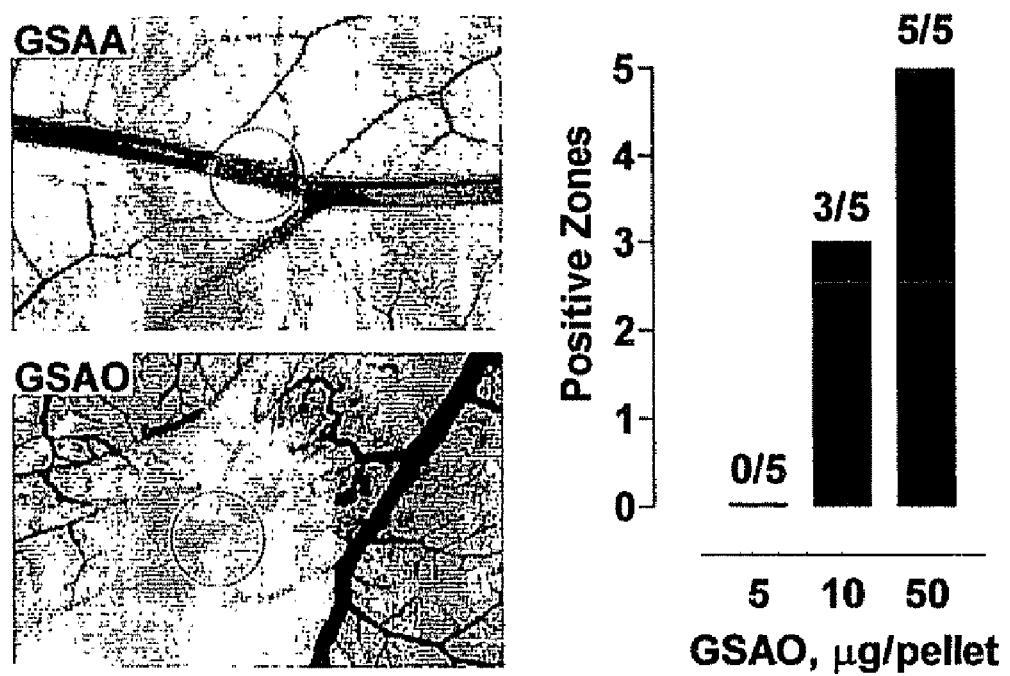
FIG. 22. Inhibition of CAM angiogenesis by GSAO. Fertilised 3 day-old white Leghorn eggs were cracked, the embryos placed in petri dishes and incubated for 3 days. Methylcellulose discs containing 5, 10 or 50 μg of either GSAA or GSAO were then applied to the CAM of individual embryos and incubated for 48 hr. The CAMs were scored for no obvious effect or inhibition of angiogenesis as defined by avascular zones. Photographs of CAM's after incubation with discs containing 10 μg of either GSM (top) or GSAO (bottom) is shown in the left hand panel. The dotted circle indicates the placement of the disc. The bar graph in the right hand panel shows the number out of 5 zones positive for angiogenesis inhibition at 5, 10 or 50 μg of GSAO per pellet. GSM did not inhibit CAM angiogenesis up to 50 μg per pellet.
Figure 23:
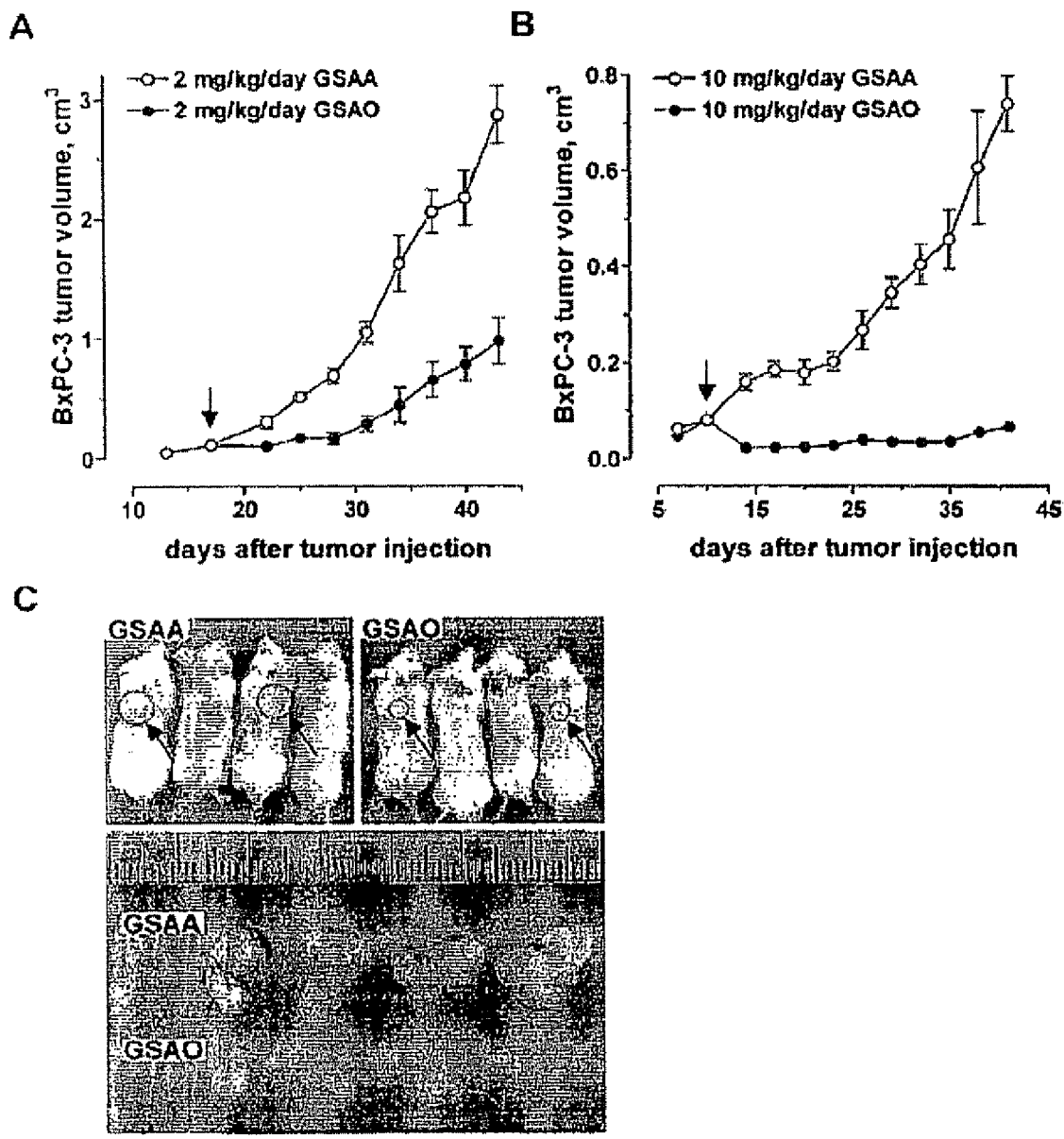
FIG. 23. Inhibition of human pancreatic tumour growth by GSAO. BxPC-3 tumours were established in the proximal midline of female 7 to 9 week old SCID mice. When the tumours were ~0.1 $cm^3$ in volume the mice were randomised into two groups and treated with either GSAM or GSAO at doses of 2 (part A) or 10 (part B) mg per kg per day in 0.2 mL of PBS containing 100 mM glycine. The compounds were administered subcutaneously at a site distant from the tumour. Tumour volume and animal weight was measured every 3 days. The GSAO/GSM tumour volume ratio at day 26 of treatment with 2 mg per kg per day was 0.34 (part A). The GSAO/GSAA tumour volume ratio at day 31 of treatment with 10 mg per kg per day was 0.09 (part B). There were 4 mice per group in part A and 4 mice treated with GSAA and 5 with GSAO in part B. The mice and excised tumours from the experiment described in Part B at day 31 of treatment are shown in Part C. The data points and errors represent the mean and SE of the tumour volumes.

GSAO inhibited angiogenesis in the CAM in a concentration-dependent manner (FIG. 22). Angiogenesis inhibition was defined as avascular zones 48 hr after implantation of methylcellulose pellets containing GSAO on the 6-day CAM (see left hand panel of FIG. 22) GSAA up to 50 µg per pellet had no effects on CAM angiogenesis. Neither GSAA nor GSAO had any apparent adverse effect on the wellbeing of the chick embryo.

EXAMPLE 3(f)

Inhibition of Tumour Growth in Mice by GSAO

Female 7 to 9 week old SCID or C57BI6/J mice were used (Massachusetts General Hospital, Boston, Mass.). Mice were held in groups of 3 to 5 at a 12 hour day and night cycle and were fed with animal chow and water ad libidum. SCID mice were anaesthetised by inhalation of isoflurane, the dorsal skin shaved and cleaned with ethanol, and a suspension of $2.5 \times 10^6$ BxPC-3 or HT1080 cells in 0.2 mL of DMEM was injected subcutaneously in the proximal midline. C57BI6/J mice with Lewis lung carcinomas of 0.6-1.2 $cm^3$ volumes were sacrificed and the skin overlying the tumour was cleaned with betadine and ethanol. Tumour tissue was excised under aseptic conditions and a suspension of tumour cells in 0.9% saline was made by passage of tumour tissue through a sieve and a series of sequentially smaller 22- to 30-gauge hypodermic needles. C57BI6/J mice were anaesthetised and prepared as for SCID mice and a suspension of Lewis lung carcinoma cells in 0.2 mL of saline was injected subcutaneously in the proximal midline. Tumours were allowed to establish and grow to a size of ~0.01 $cm^3$ after which they were is randomised into two groups. The tumours were measured in two diameters and tumour volume was calculated using the relationship, tumour volume=$a \times b^2 \times 0.52$, where a is the longest and b the shortest diameters in cm. Animals were treated with either GSAA or GSAO at doses of 2 or 10 mg per kg per day in 0.2 mL of PBS containing 100 mM glycine. The compounds were administered subcutaneously at a site distant from the tumour. Tumour volume and animal weight was measured every 3 days. The tumours were excised and weighed when the animals were sacrificed.

The growth of human pancreatic primary tumours in immunocompromised mice was markedly suppressed by systemic administration of GSAO. Subcutaneous administration of 2 mg GSAO per kg per day caused a ~70% inhibition of the rate of BxPC-3 tumour growth (FIG. 23A) while administration of 10 mg GSAO per kg per day caused a >90% inhibition of the rate of tumour growth (FIGS. 23B and C). Administration of 2 mg per kg per day GSAA had no effect on the rate of BxPC-3 tumour growth while administration of 10 mg GSAA per kg per day resulted in a small inhibition in the rate of tumour growth (<20%) when compared to administration of vehicle alone (not shown).

Figure 24:
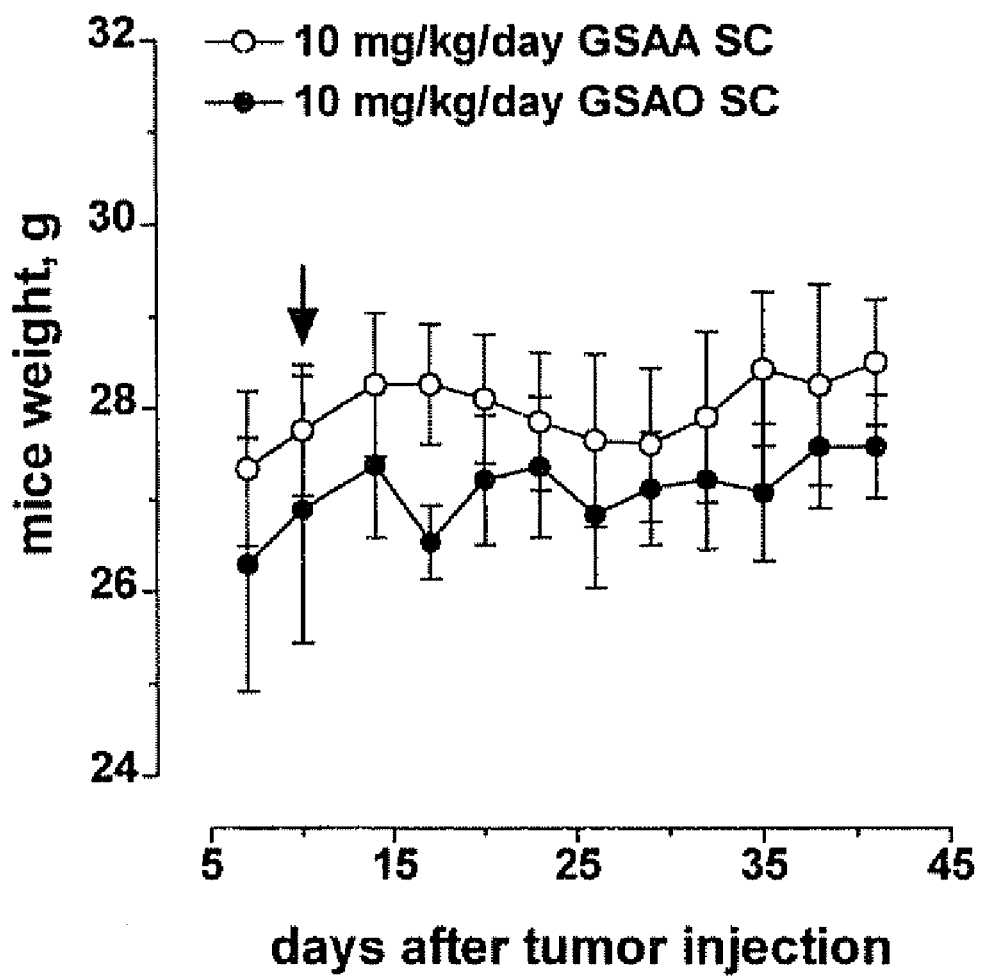
FIG. 24 Systemic administration of GSAO had no effect on mice weight. The data points and errors represent the mean and SE of the animal weights for the experiment described in FIG. 23.
Figure 25:
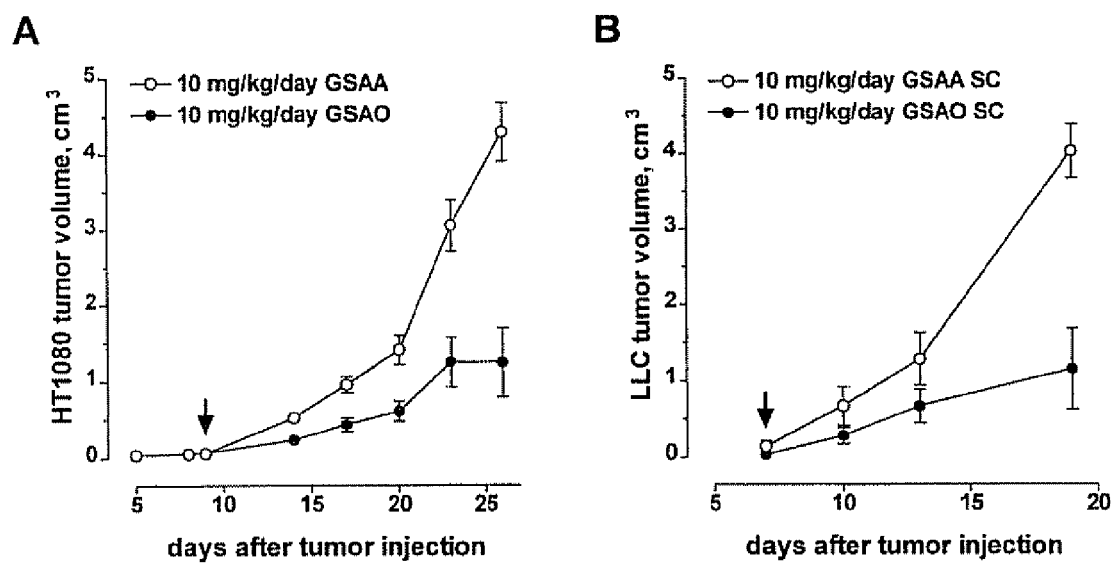
FIG. 25. Inhibition of human fibrosarcoma and murine Lewis lung tumour growth following systemic administration of GSAO. HT1080 or Lewis lung tumours were established in the proximal midline of female 7 to 9 week old SCID or C57BI6/J mice, respectively. When the tumours were ~0.1 $cm^3$ in volume the mice were randomised into two groups (n=5) and treated with either GSM or GSAO at a dose of 10 mg per kg per day in 0.2 mL of PBS containing 100 mM glycine, The compounds were administered subcutaneously at a site distant from the tumour. Tumour volume and animal weight was measured every 3 days. The GSAO/GSAA HT1080 tumour volume to ratio at day 17 of treatment was 0.29 (part A). The GSAO/GSAA Lewis lung tumour volume ratio at day 12 of treatment was 0.29 (part B). The data points and errors represent the mean and SE of the tumour volumes.
Figure 26:
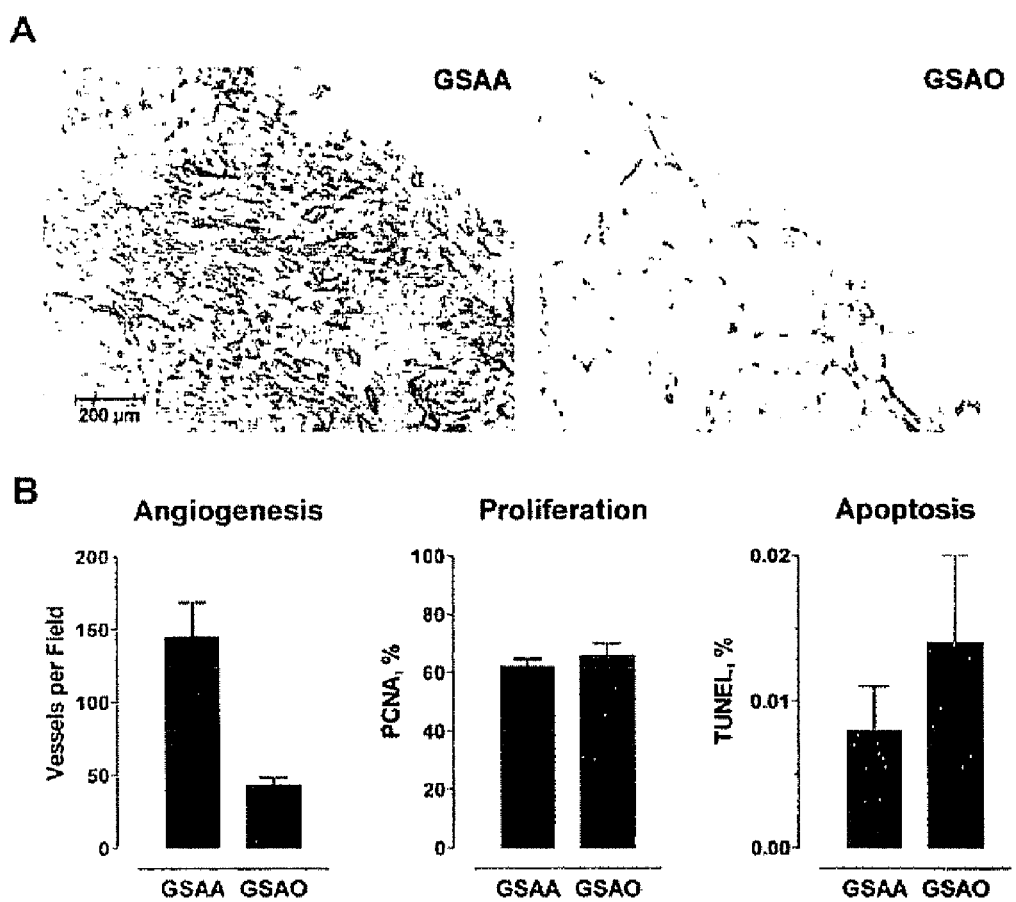
FIG. 26. Inhibition of angiogenesis in human pancreatic tumours by GSAO. Histological sections of the BxPC-3 tumours shown in part C of FIG. 23 from GSM and GSAO-treated mice were analysed for angiogenesis (CD-31), proliferation (PCNA) and apoptosis (TUNEL). There was a marked suppression of angiogenesis (part A, p<0.001) and an increase in the apoptotic index of tumour cells (part C, p=0.05) in the GSAO-treated tumours. In contrast, there was no significant difference in the proliferative (part B) indices of GSM versus GSAO-treated tumour cells.

There was no apparent adverse side effects of administration of either GSAO or GSM to the mice. The average mice weights of the GSM and GSAO treatment groups over the course of the experiments were the same at both doses (FIG. 24). At the conclusion of the experiment described in FIG. 23B the mice from both treatment groups were examined. There was no apparent macroscopic differences between the GSAA or GSAO-treated and untreated mice. The heart, lungs, liver, kidneys, and spleen of the GASM or GSAO-treated and untreated mice were fixed in formaldehyde, embedded in paraffin, sectioned, stained with haematoxylin and eosin and examined by light microscopy. There was no obvious morphological changes in any of the organs of the treated mice when compared to the organs of untreated mice (not shown).

The growth of human fibrosarcoma primary tumours in immunocompromised mice and murine Lewis lung primary tumours in immunocompetent mice were also suppressed by systemic administration of GSAO. Subcutaneous administration of 10 mg GSAO per kg per day caused a ~70% inhibition of the rate of fibrosarcoma (FIG. 25A) and Lewis lung (FIG. 25B) tumour growth. Administration of 10 mg GSM per kg per day had no effect on the rate of Lewis lung tumour growth in C57Bl6/J mice when compared to administration of vehicle alone (not shown).

EXAMPLE 3(g)

Inhibition of Angiogenesis in Human Pancreatic Tumours by GSAO

The tumours shown in FIG. 23C were fixed in Buffered Formalde-Fresh (Fisher Scientific, Fair Lawn, N.J.), embedded in paraffin and five am thick sections were cut and placed on glass slides. Sections were stained with haematoxylin and eosin or for CD31, PCNA or fragmented DNA (TUNEL). Sections were incubated overnight at 4° C. with a 1:250 dilution of anti-mouse CD-31 antibody (PharMingen, San Diego, Calif.) followed by a 1:200 dilution of biotinylated anti-rat secondary antibody (Vestor, Burlingame, Calif.). The staining was enhanced by tyramide amplification (New England Nuclear, Boston, Mass.). Staining for PCNA was performed as described by Holmgren et al. (1995) while TUNEL labeling of fragmented DNA was performed according to Gavrielli et al. (1992).

Vascular density was determined by selecting 3 tumours, including the smallest and largest, from the control and treatment groups. Microvessels were counted and their density was graded in the most active areas of neovascularisation (Weidner et al., 1991). Sections were examined under 100× magnification to find the areas of most active neovascularisation and three different fields were counted at 400× magnification for the number of microvessels. The highest of the three counts was the value taken and two sections from each tumour was examined. The proliferative index was estimated by the percentage of cells scored under 400× magnification (Holmgren et al, 1995). A minimum of 1000 cells was counted in two separate sections. The apoptotic index was estimated by the percentage of cells scored under 400× magnification. A minimum of 1500 cells was counted in two separate sections (Holmgren et al., 1995).

There was no macroscopic or microscopic signs of necrosis of either GSAA- or GSAO-treated tumours (not shown). Immunohistochemical analysis of the tumours indicated a marked reduction in angiogenesis in the GSAO-treated tumours (p<0.001) (FIG. 26A) and an increase in the apoptotic index of the tumour cells (p=0.05) (FIG. 26C). The proliferative indices of the GSAA- and GSAO-treated tumours were the same (FIG. 26B).

EXAMPLE 3(h)

Figure 27:
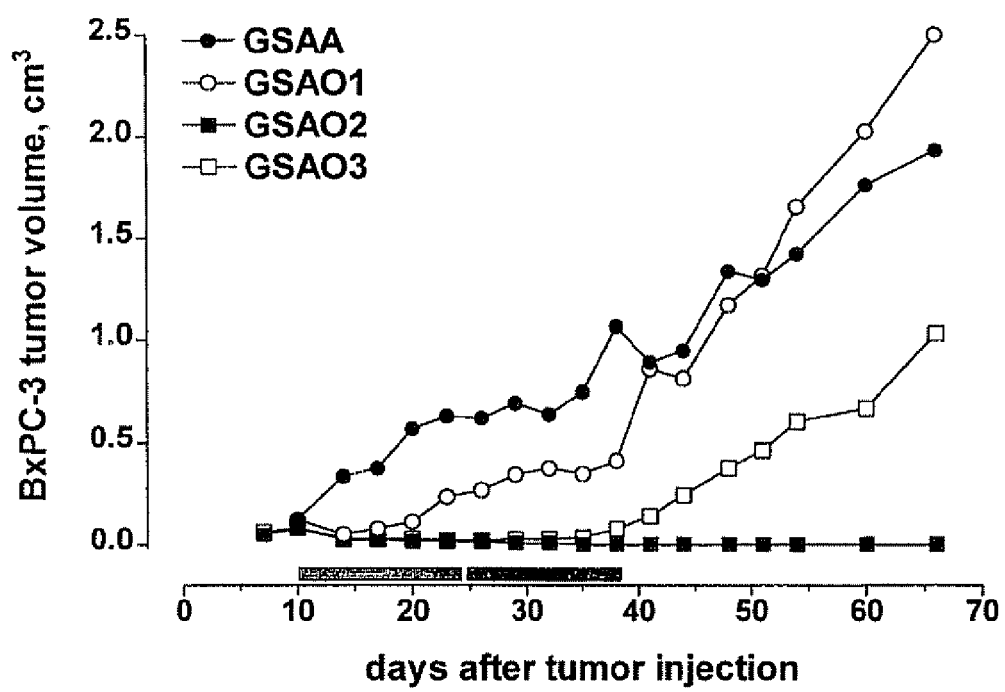
FIG. 27. Inhibition of human pancreatic carcinoma tumour growth by continuous intraperitoneal administration of GSAO. BxPC-3 tumours were established in the proximal midline of female 7 to 9 week old SCID mice. Mice bearing ~0.1 g tumours were implanted with 14 day alzet model 1002 micro-osmotic pumps (ALZA Corporation, Palo Alto, Calif.) in the peritoneal cavity. The pumps contained 45 mg per mL GSAA or GSAO and delivered 10 mg per kg per day. The pumps were replaced after 14 days. Pump duration is indicated by the shaded bar. Tumour volume and animal weight was measured every 3 days.

Inhibition of Human Pancreatic Carcinoma Tumour Growth by Continuous Intraperitoneal Administration of GSAO SCID mice bearing subcutaneous human BxPC-3-pancreatic carcinoma tumours were implanted with 14 day microosmotic pumps in the peritoneal cavity. The pumps delivered 10 mg per kg per day GSM or GSAO and were replaced after 14 days with fresh pumps. The rate of growth of the BxPC-3 tumours was inhibited in the mice receiving GSAO (FIG. 27). Tumour growth was slowed in one mouse by ~50% and halted completely in two other mice. When the second pump was exhausted one of the halted tumours began to grow at about the same rate as the GSAA-treated tumour while the other tumour had resolved completely. There was no significant effect on the rate of BxPC-3 tumour growth in mice receiving GSAA.

EXAMPLE 3(i)

Figure 28:
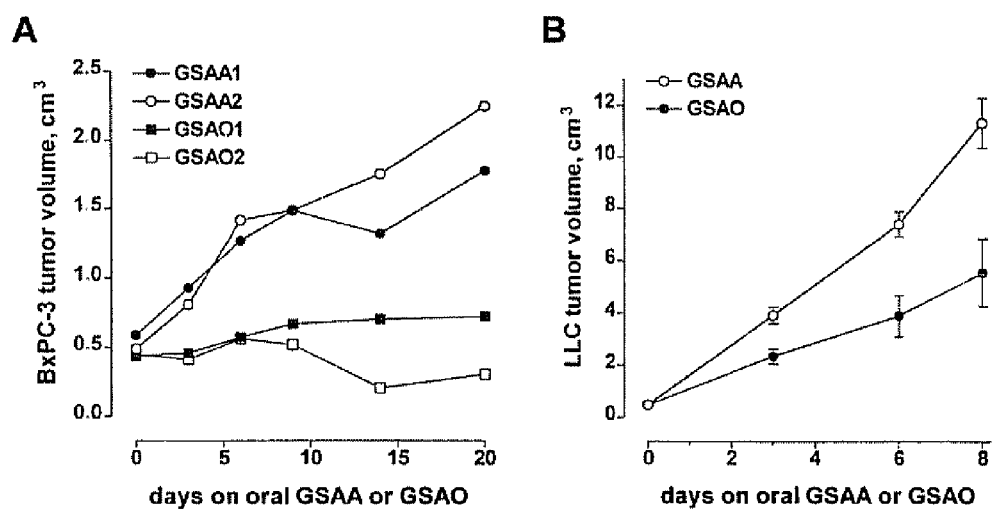
FIG. 28. Inhibition of human pancreatic carcinoma and murine Lewis lung tumour growth by oral administration of GSAO. BxPC-3 or Lewis lung tumours were established in the proximal midline of female 7 to 9 week old SCID or C57BI6/J mice, respectively. SCID mice bearing ~0.5 g BxPC-3 tumours or C57BI6/J mice bearing 0.1 g Lewis lung tumours were randomised into two groups (n=2 for BxPC-3 and n=3 for Lewis lung) and treated with either GSAA or GSAO (0.05 mg per mL) in their water. Mice drink ~5 mL of water per day and therefore consumed ~10 mg GSAO or GSM per kg per day. The water contained 100 mM glycine to minimise oxidation of GSAO. Tumour volume and animal weight was measured every 3 days. The data points and errors represent the mean and SE of the tumour volumes.

Inhibition of Human Pancreatic Carcinoma and Murine Lewis Lung Tumour Growth by Oral Administration of GSAO SCID mice bearing subcutaneous human pancreatic carcinoma tumours or C57Bl6/J mice bearing subcutaneous murine Lewis lung tumours were fed either ~10 mg per kg per day GSAO or GSM in their water. The pancreatic tumours stopped growing when the mice started drinking the GSAO, while the rate of Lewis lung tumour growth was reduced by ~50% (FIG. 28). GSM in the water had no significant effect on growth of either tumour.

EXAMPLE 3(j)

Use of GSAO as a Tumour Imaging Agent

The distribution in vivo of a fluorescently-tagged GSAO (FIG. 29A) was measured in tumour-bearing mice. Lewis lung carcinomas were established subcutaneously in the proximal midline of female 7 to 9 week old C57Bl6/J mice as described above. GSAO-Cy5.5 (0.1 mL; 15 nmoles per mice) was injected subcutaneously at a site distant from the tumour. Mice were imaged after 24 hours by exciting with 610-650 nm light and measuring fluorescence emission at 700 nm (Weissleder et al., 1999).

Figure 29:
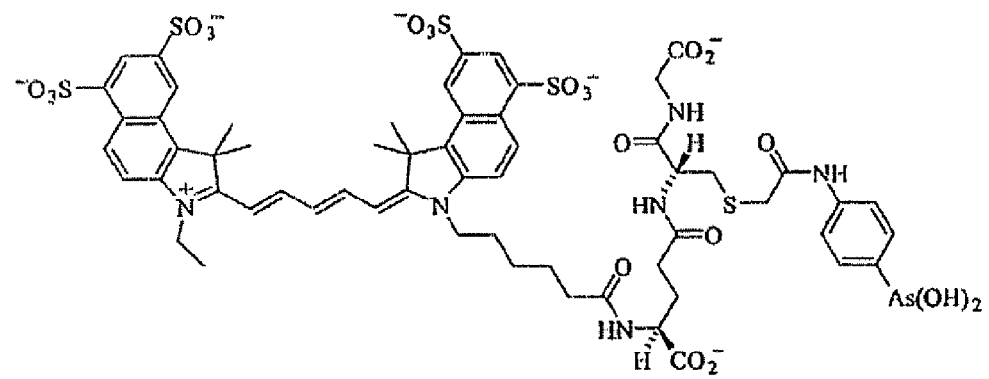
FIG. 29. Selective uptake of GSAO-Cy5.5 by solid tumours. A Structure of GSAO-Cy5.5. B GSAO-Cy5.5 (15 nmoles) was injected subcutaneously in the flank of a C57816/J mice bearing a ~1000 $mm^3$ subcutaneous Lewis lung tumor in the proximal midline. The dorsum of the mice was imaged 24 hours later. The area of the image is ~0.7 $cm^2$ of the proximal midline of the dorsum and encompasses normal dorsum and the bottom edge of the subcutaneous tumour. There was a slight concentration of GSAA-Cy5.5 in the tumour but this was insignificant compared to accumulation of GSAO-Cy5.5 (not shown).
Figure 29:
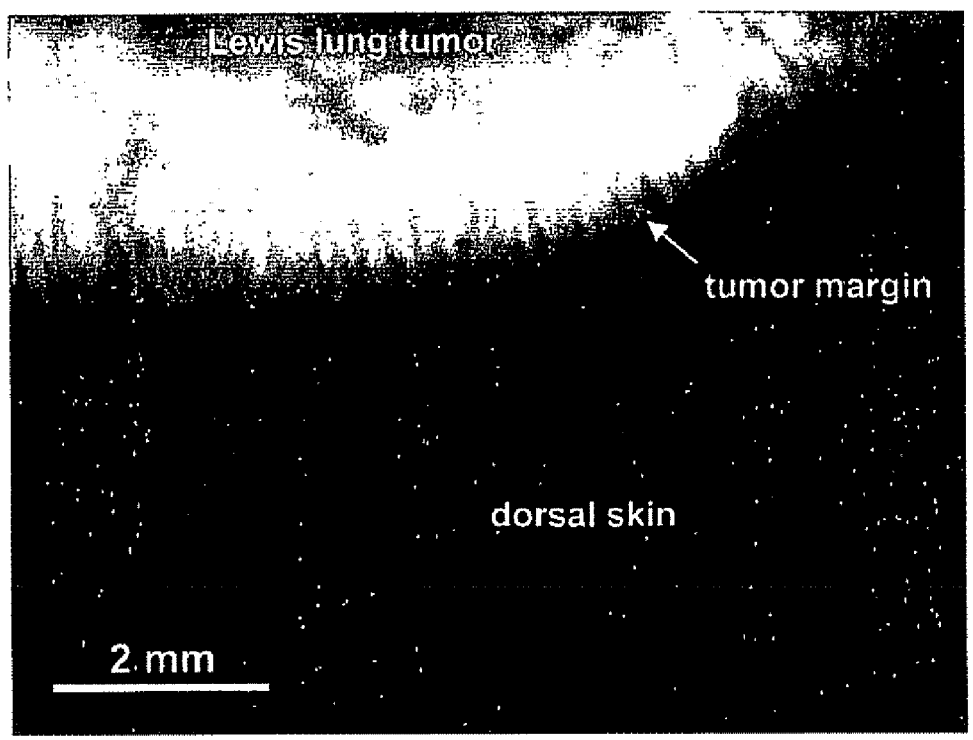

There was a striking accumulation of GSAO-Cy5.5 in the tumour (FIG. 29B). Importantly, there was no obvious accumulation of GSAO-Cy5.5 elsewhere in the mouse (not shown).

EXAMPLE 4

Effect of GSAO on HIV Infection

EXAMPLE 4(a)

Labelling of Cell Surface CD4 with MPB

CEM-T4 cells were obtained from the NIH AIDS Research and Reference Reagent Program, Rockville, Mass. CEM-T4 (1 mL of $5 \times 10^6$ per mL in Hanks balanced salt solution) were incubated with either sulfosuccinimidobiotin (SSB), 3-(N-maleimidylpropionyl)biocytin (MPB), or GSAO-B (100 μM) for 30 min at room temperature SSB was from Pierce, Rockford, Ill. while MPB was from Molecular Probes, Eugene, Oreg. Unreacted SSB was quenched with glycine (200 μM), while unreacted MPB was quenched with reduced glutathione (GSH, 200 μM) for 30 min at room temperature. The labelled cells were washed twice with PBS and sonicated in 1 mL of 50 mM Tris-HCl, 0.5 M NaCl, 1% (v/v) Triton X-100, 10 μM leupeptin, 10 μM aprotinin, 2 mM phenylmethylsulfonyl fluoride, 5 mM EDTA, pH 8.0 buffer at 4° C. Streptavidin-agarose beads (25 μl of packed beads) were incubated with the cell lysates for 1 h at 4° C. on a rotating wheel to isolate the biotin-labelled proteins. The streptavidin-agarose beads were washed 5 times with 50 mM Tris HCl, 0.15 M NaCl, 0.05% Triton X-100, pH 8.0 buffer. The biotin-labelled proteins were released from the beads by boiling in 50 μl of SDS-.Laemmli buffer for 2 minutes, resolved on 10% SDS-PAGE, transferred to PVDF membrane, and Western blotted using the CD4 monoclonal antibody, Leu3a (Becton Dickinson, Bedford, Mass.). On one occasion the MPB was preblocked with GSH prior to incubation with cells. On another occasion cells were labeled with GSAO-B in the presence of DMP (400 μM)

It was hypothesised that CD4 on the T cell surface contains a redox active disulfide bond which is important for CD4 function. To test this hypothesis, the CD4+ T cell line, CEM-T4, was labelled with either sulfosuccinimidobiotin (SSB) or 3-(N-maleimidylpropionyl)biocytin (MPB) SSB labels primary amines while MPB labels free thiols, and both reagents are membrane impermeable. The labelled proteins were collected on streptavidin agarose, resolved on SOS-PAGE and transferred to PVDF membrane. Labelled CD4 was detected by blotting with the CD4 monoclonal antibody, Leu3a (FIG. 30A). SSB-labelled CD4 is a measure of total cell surface CD4, while MPB-labelled CD4 is a measure of reduced cell surface CD4. Labelling with MPB was thiol specific as preblocking of the MPB with reduced glutathione (GSH) ablated labelling CD4 on human blood T cells was also labelled with MPB and it was found that mitogenic activation of the T cells increases the fraction of cell surface CD4 that contains a free thiol (not shown). These observations indicate that T cell activation changes the redox state of CD4.

Also, another Ig fold receptor, Thy-1, was not labelled with MPB on the TIB-47 cell line (not shown). In addition, MPB labeled serum albumin, which contains a free thiol, but not the plasma proteins plasminogen and prothrombin, which do not contain free thiols (not shown).

To demonstrate specific incorporation of MPB into CD4, T cells were labelled with MPB and the CD4 immunoprecipitated with Leu3a. CEM-T4 cells were labelled with MPB as described above, incubated with Leu3a monoclonal antibody (5 µl) for 30 minutes, washed three times, and sonicated in 1 mL of 50 mM Trs-HCl, 05 M NaCl, 1% (v/v) Triton X-100, 10 µM leupeptin, 10 µM aprotinin, 2 mM phenylmethylsulfonyl fluoride, 5 mM EDTA, pH 8.0 buffer. The detergent insoluble material was removed by centrifugation at 12000 g for 30 minutes, and the supernatant incubated with $1 \times 10^7$ goat anti-mouse IgG coated Dynabeads (Dynal, Carlton South, VIC) for 60 minutes. All incubations were at 4° C. The beads were washed and the bound CD4 released by boiling the beads in 50 µl of SDS-Laemmli buffer for 2 minutes. The CD4 was resolved on 10% SDS-PAGE, transferred to PVDF membrane, and blotted with streptavidin peroxidase to detect the biotin label. The purified CD4 was resolved on SDS-PAGE, transferred to PVDF membrane and blotted with streptavidin peroxidase to detect the MPB label (FIG. 30B).

EXAMPLE 4(b)

Reduction of Cell Surface CD4 with Thioredoxin

Figure 30:
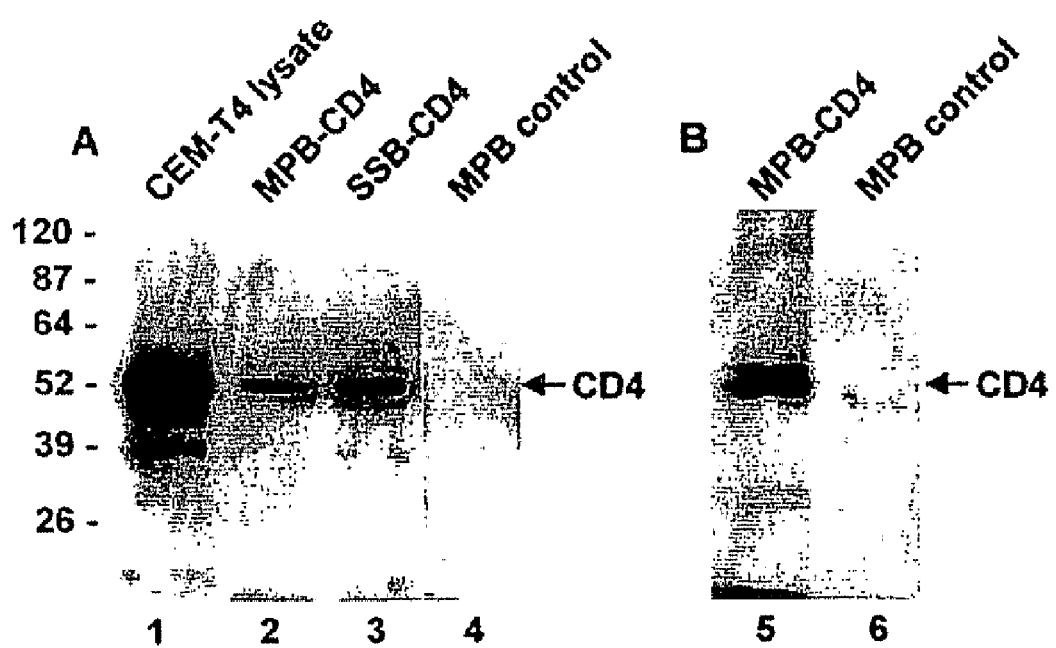
FIG. 30. Labelling of cell surface CD4 with MPB. A CEM-T4 cells were labelled with either SSB or MPB. The biotin-labelled proteins were collected on streptavidin-agarose beads, resolved on 10% SDS-PAGE and Western blotted using the CD4 monoclonal antibody, Leu3a. Lane 1 is CEM-T4 lysate (from 1×10⁶ cells), lane 2 is SSB-labelled CEM-T4 CD4, while lane 3 is MPB-labelled CEM-T4 CD4. Biotin-labelled proteins were from 2×10⁶ cells. Lane 4 is a control experiment Is where MPB was pre-blocked with GSH prior to incubation with CEM-T4 cells (from 2×10⁶ cells). The positions of $M_r$ markers in kDa are shown at left. B CEM-T4 cells were labelled with MPB and the CD4 immunoprecipitated with Leu3a monoclonal antibody and goat anti-mouse IgG coated Dynabeads The CD4 was resolved on 10% SDS-PAGE and blotted with streptavidin peroxidase to detect the biotin label. Lane 5 is MPB-labelled 0D4 (from 2×10⁶ cells). Lane 6 is a control experiment where MPB was pre-blocked with GSH prior to incubation with CEM-T4 cells (from 2×10⁶ cells). The positions of $M_r$ markers in kDa are shown at left.
Figure 31:
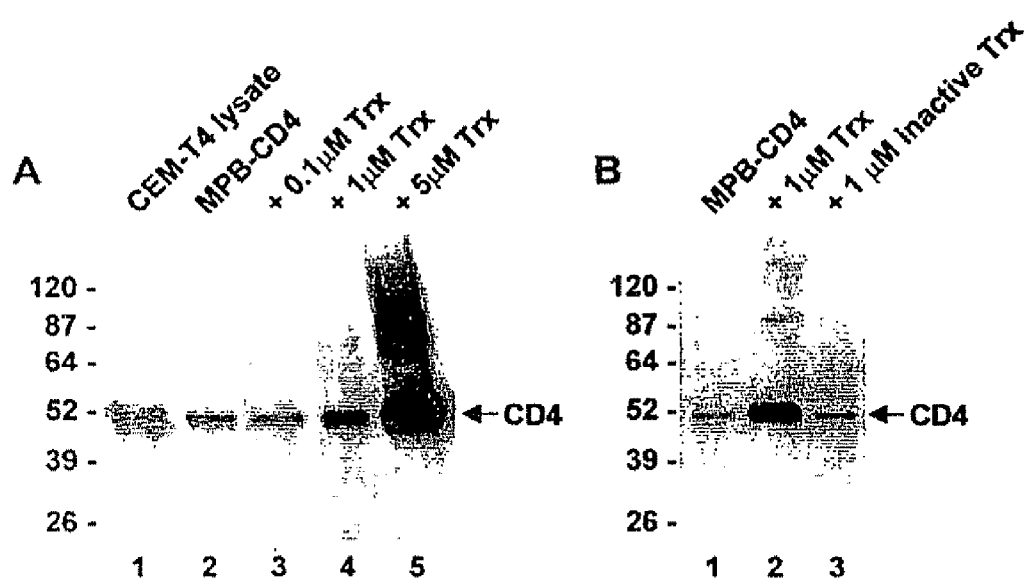
FIG. 31. Reduction of cell surface CD4 with thioredoxin. A CEM-T4 cells were incubated without or with increasing concentrations of thioredoxin for 1 hr at 37° C. and then labelled with MPB. The biotin-labelled proteins were resolved on 5-15% SDS-PAGE and Western blotted using Leu3a monoclonal antibody. Lane 1 is CEM-T4 lysate and lanes 2-5 are MPB-labelled CD4 on CEM-T4 cells incubated with 0 μM (lane 2), 0.1 MM (lane 3), 1 μM (lane 4), or 5 μM Trx (lane 5). The positions of $M_r$ markers in kDa are shown at left. B CEM-T4 cells were incubated with either 1 μM thioredoxin or a redox inactive mutant of thioredoxin for 1 hr at 37° C. The biotin-labelled proteins were resolved on 5-15% SDS-PAGE and Western blotted using Leu3a monoclonal antibody. Lane 1 is untreated CEM-T4 cells, while lanes 2 and 3 are cells incubated with either redox active or inactive thioredoxin. The positions of $M_r$ markers in kDa are shown at left.

The labelling experiments shown in FIG. 30 demonstrate that one or more of the 3 disulfide bonds in cell surface CD4 are redox active. Disulfide bond reduction/oxidation in a protein is usually very specific and quite slow, unless catalysed. It was hypothesised that the oxidation state of the CD4 disulfide bond(s) would be controlled by an enzyme secreted by CD4+ cells, Thioredoxin is secreted by CD4+ T lymphocytes (Rosen et al., 1995). Incubation of CEM-T4 cells with increasing concentrations of thioredoxin resulted in increasing labelling of CD4 with MPB (FIG. 31A). As a control, incubation with a redox inactive thioredoxin mutant did not cause increased MPB labelling (FIG. 31B). Incubation of CEM-T4 cells with another disulfide reductase, PDI, did not result in increased labelling of CD4 with MPB (not shown).

EXAMPLE 4(c)

Labelling of Cell Surface CD4 With GSAO-B

Figure 32:
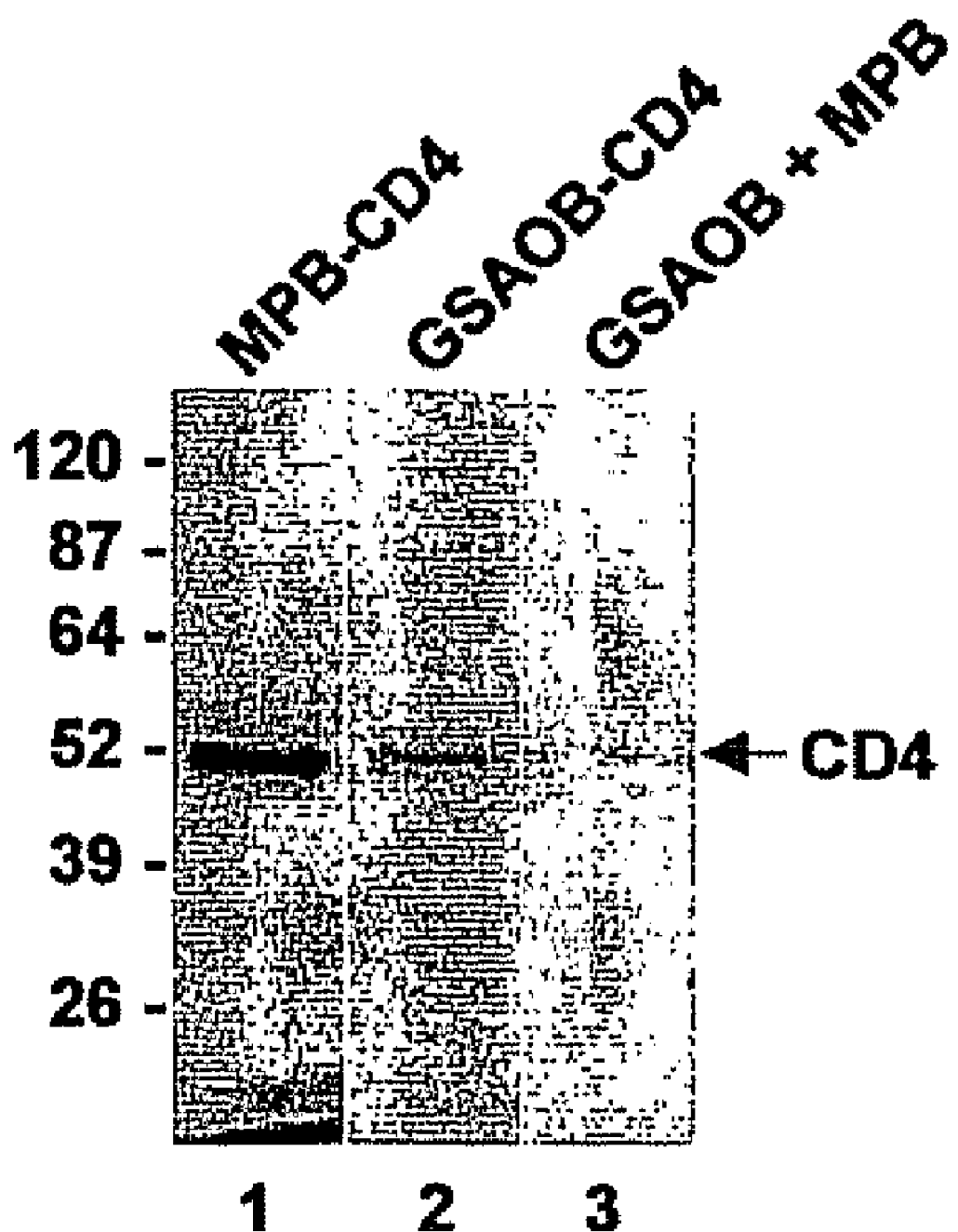
FIG. 32. Labelling of cell surface CD4 with GSAO-B. CEM-T4 were labelled with either MPB or GSAO-B. The biotin-labelled proteins were collected on streptavidin-agarose beads, resolved on 5-15% SDS-PAGE and Western blotted using Leu3a monoclonal antibody. Lane 1 is MPB-labelled CEM-T4 CD4 and lane 2 is GSAO-B-labelled CEM-T4 CD4. Lane 3 is a control experiment where GSAO-B was incubated with CEM-T4 cells in the presence of 400 μM DMP. Biotin-labelled proteins were from $2\times10^6$ cells. The positions of $M_r$ markers in kDa are shown at left.
Figure 33:
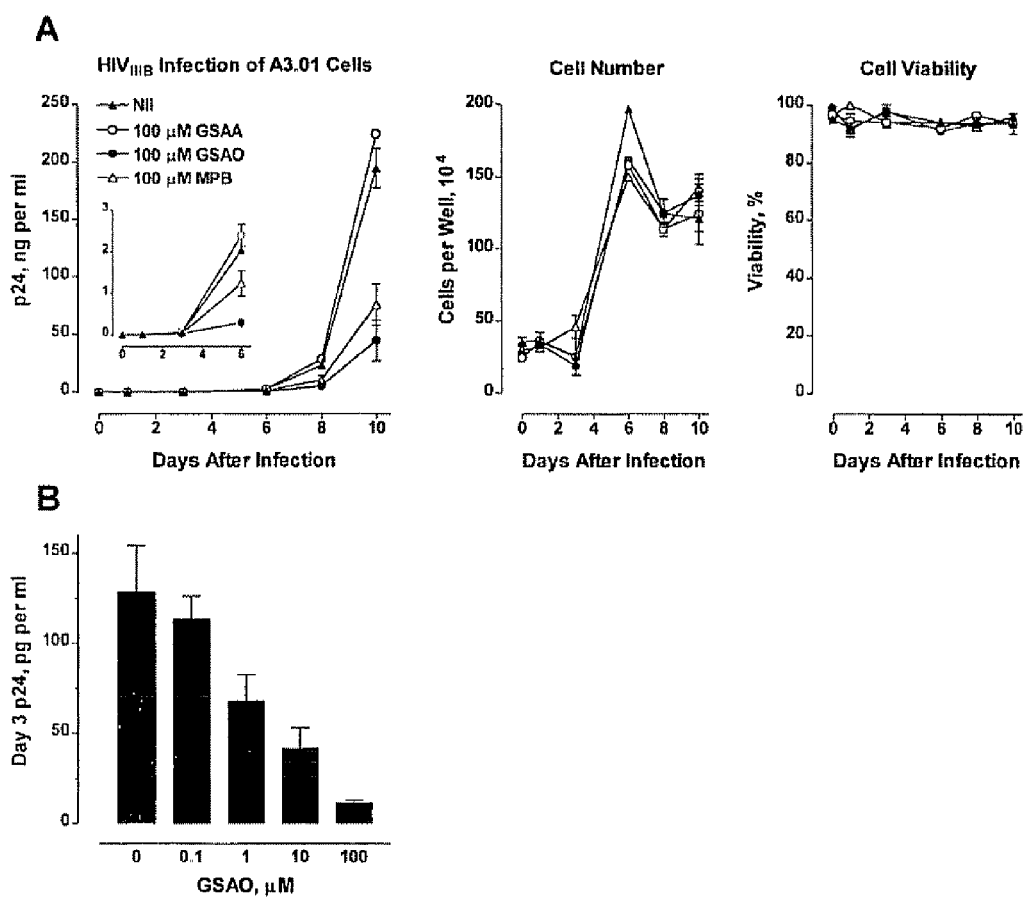
FIG. 33. Inhibition of $HIV_{IIIB}$ entry into A3.01 cells by MPB and GSAO. A A3.01 bells ($1\times10^6$ per mL) were incubated with GSM, GSAO or MPB (100 μM) for 30 minutes at 37° C. and then with $HIV_{IIIB}$ (50 $TCID_{50}$ per $10^6$ cells) for 2 hours at 37° C. Cells were washed and incubated in complete medium at 5% $CO_2$ and 37° C. for up to 10 days. At the indicated times the conditioned medium was collected and assayed for p24 antigen and cell number and cell viability was determined B Concentration dependence of GSAC. A3.01 cells ($1\times10^6$ per mL) were incubated with GSAO (0-100 μM) for 30 minutes at 37° C. and then with $HIV_{IIIB}$ (50 $TCID_{50}$ per $10^6$ cells) for 2 hours at 37° C. Cells were washed, incubated in complete medium at 5% $CO_2$ and 37° C. for 3 days and the conditioned medium collected and assayed for p24 antigen.

T cell surface CD4 also incorporated GSAO-B. CEM-T4 cells were labeled with GSAO-B, the labelled proteins collected on streptavidin agarose, resolved on SDS-PAGE and transferred to PVDF membrane. Labelled CD4 was detected by blotting with the Leu3a monoclonal antibody (FIG. 32). This result indicated that the two thiols of the reduced form of CD4 were sufficiently close to complex with the trivalent arsenical of GSAO.

EXAMPLE 4(d)

Inhibition of HIV Infection of CD4+ Cells by GSAO

A3.01 human T cells were exposed to GSAO for 30 minutes and then to $HTLV_{IIIB}$ virus for 2 hours after which the cells were washed and then cultured for up to 10 days. $HTLV_{IIIB}$ and A3.01 cells were obtained from the NIH AIDS Research and Reference Reagent Program, Rockville, Mass. Virus stocks were made and infectivity titer determined using A3.01 cells and the p24 antigen assay (Coulter, Miami, Fla.). A3.01 cells were cultured in RPMI medium containing 10% fetal calf serum. A3.01 cells were incubated with GSAO (0-100 µM), GSM (100 µM) or MPB (100 µM) for minutes at 37° C. in serum-free media. Virus was added at 50 $TCID_{50}$ per $10^6$ cells for 2 hours at 37° C. Cells were washed three times, resuspended in 0.25 mL of complete medium without or with GSAO or GSAA (10 µM) and incubated in 96 well tissue culture plates. Samples were removed at discrete time points and assayed for p24 antigen using the Coulter HIV-1 p24 Antigen Assay (Coulter, Miami, Fla.). Fresh media without or-with GSAO or GSM (10 µM) was added to the wells on the days of sampling. Cell numbers and cell viability were determined at the times specified by staining cells with trypan blue and counting using a Neubauer haemacytometer. Cell viability was measured as a percentage of live cells to total cells.

Figure 34:
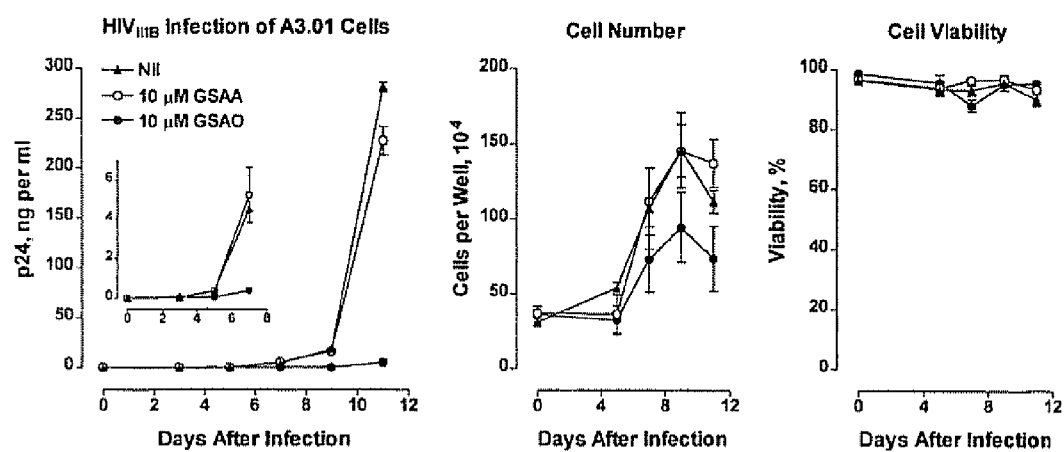
FIG. 34. Inhibition of $HIV_{IIIB}$ infection of A3.01 cells by GSAO. A3.01 cells ($1\times10^6$ per mL) were incubated with GSAA or GSAO (10 μM) for 30 minutes at 37° C. and then with $HIV_{IIIB}$ (50 $TCID_{50}$ per $10^6$ cells) for 2 hours at 37° C. Cells were washed and incubated in complete medium containing GSAA or GSAO (10 μM) at 5% $CO_2$ and 37° C. for tip to 10 days. At the indicated times the conditioned medium was collected and assayed for p24 antigen and cell number and cell viability was determined.

GSAO inhibited entry of $HIV_{IIIB}$ into the T cell line, A3.01 (FIG. 33A). The half-maximal effect of GSAO was ~1 µM (FIG. 33B). GSAO had no effect on cell proliferation or cell viability up to 100 µM concentration (FIG. 33A). Moreover, GSAO at 10 µM effectively blocked $HIV_{IIB}$ infection of A3.01 cells for 11 days (FIG. 34). GSAO had a small inhibitory effect on cell proliferation and no effect on cell viability (FIG. 34).

Figure 35:
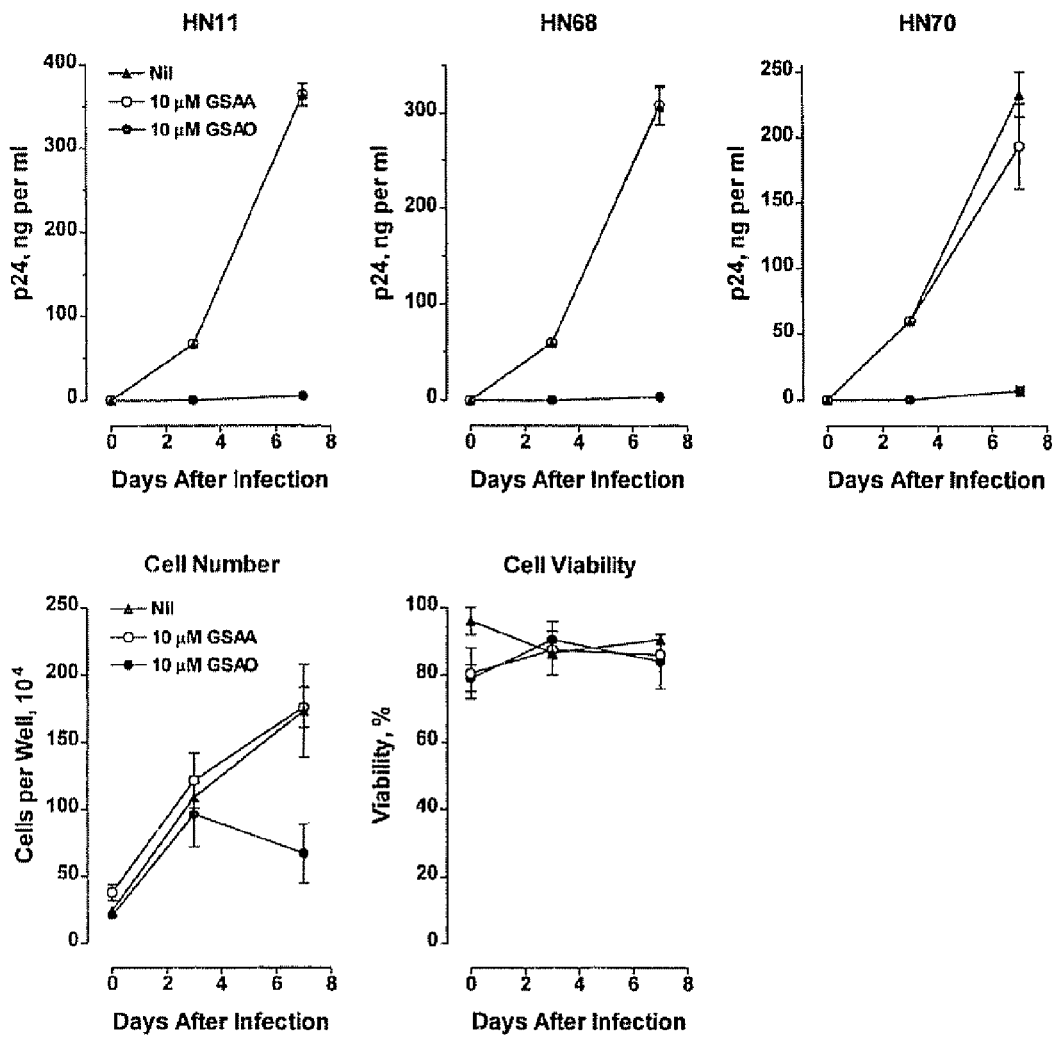
FIG. 35. Inhibition of HIV infection of PBMC's by GSAO. PBMC's ($1\times10^6$ per mL) were incubated with GSAA or GSAO (10 μM) for 30 minutes at 37° C. and then with primary HIV isolates (HN11, HN68 or HN70 at 50 $TCID_{50}$ per $10^6$ cells) for 2 hours at 37° C. Cells were washed and incubated in complete medium containing GSM or GSAO (10 μM) at 5% $CO_2$ and 37° C. for up to 7 days. At the indicated times the conditioned medium was collected and assayed for p24 antigen and cell number and cell viability was determined.

GSAO also inhibited infection of peripheral blood mononuclear cells (PBMC) by primary HIV isolates. The primary HIV isolates, HN11, HN68 and HN70, were provided by Dr Hassan Naif, Centre for Virus Research, Westmead Millennium Institute, NSW, Australia, PBMC's were prepared from 400 mL of fresh citrated blood by Ficoll-Hypaque separation (Pharmacia Biotech, Upsalia, Sweden). The blood was diluted 1:2 with PBS, layered onto Ficoll-Hypaque (35 mL blood onto 15 mL Ficoll-Hypaque) in 50 mL Falcon tubes and centrifuged at 400 g for 20 minutes at 20° C. The PBMC's were collected and pelleted at 1200 rpm for 10 minutes to remove platelets, s resuspended at $2 \times 10^6$ cells per mL in RPMI containing 20% horse serum (Gibco BRL, Gaithersburg, Md.), 10 µg per mL phytohemagglutinin-M (PHA-M, Boehringer Mannheim Biochemica, Mannheim, Germany) and 50 U per mL interleukin-2 (Sigma, St. Louis, Mo.) and incubated for 2 days at 5% $CO_2$ and 37° C. PBMC ($1 \times 10^6$ per mL) were incubated with GSAO or GSAA (10 μM) for 30 minutes at 37° C. in serum-free media. Virus was added at 50 TCID$_{50}$ per 10$^6$ cells for 2 hours at 37° C. Cells were washed three times, resuspended in 0.25 mL of complete medium with GSAO or GSAA (10 μM) and incubated in 96 well tissue culture plates. Samples were removed at discrete time points and assayed for p24 antigen. Fresh media with GSAO or GSM (10 μM) was added to the wells on the days of sampling. GSAO blocked infection of PBMC's by three different primary HIV isolates for 7 days (FIG. 35). GSAO inhibited proliferation of is PBMC's after 3 days culture but had no effect of cell viability over the 7 days (FIG. 35).

EXAMPLE 5

Pharmaceutical Formulations

The compounds of the present invention may be administered alone, although it is preferable that they be administered as a pharmaceutical formulation. The active ingredient may comprise, for topical administration, from 0.001% to 10% by weight, and more typically from 1% to 5% by weight of the formulation, although it may comprise as much as 10% by weight.

In accordance with the best mode of performing the invention provided herein, specific preferred pharmaceutical compositions of the present invention are outlined below. The following are to be construed as merely illustrative examples of formulations and not as a limitation of the scope of the present invention in any way.

EXAMPLE 5(a)

Topical Cream Composition

A typical composition for delivery as a topical cream is outlined below:
GSAO 1.0 g
Polawax GP 200 25.0 g
Lanolin Anhydrous 3.0 g
White Beeswax 4.5 g
Methyl hydroxybenzoate 0.1 g
Deionised & sterilised Water to 100.0 g The polawax, beeswax and lanolin are heated together at 60° C., a solution of methyl hydroxybenzoate is added and homogenisation achieved using high speed stirring. The temperature is then allowed to fall to 50° C. The compound of the present invention, in this example being GSAO, is then added and dispersed throughout, and the composition is allowed to cool with slow speed stirring.

EXAMPLE 5(b)

Topical Lotion Composition

A typical composition for delivery as a topical lotion is outlined below:
GSAO 1.2 g
Sorbitan Monolaurate 0.8 g
Polysorbate 20 0.7 g
Cetostearyl Alcohol 1.5 g
Glycerin 7.0 g
Methyl Hydroxybenzoate 0.4 g
Sterilised Water about to 100.00 ml Is The methyl hydroxybenzoate and glycerin are dissolved in 70 ml of the water at 75° C. The sorbitan monolaurate, polysorbate 20 and cetostearyl alcohol are melted together at 75° C. and added to the aqueous solution. The resulting emulsion is homogenised, allowed to cool with continuous stirring and the GSAO is added as a suspension in the remaining water. The whole suspension is stirred until homogenised.

EXAMPLE 5(c)

Eye Drop Composition

A typical composition for delivery as an eye drop is outlined below,
GSAO 0.3 g
Methyl Hydroxybenzoate 0.005 g
Propyl Hydroxybenzoate 0.06 g
Purified Water about to 100.00 ml.

The methyl and propyl hydroxybenzoates are dissolved in 70 ml purified water at 75° C., and the resulting solution is allowed to cool. GSAO is then added, and the solution sterilised by filtration through a membrane filter (0.22 μm pore size), and aseptically packed into sterile containers.

EXAMPLE 5(d)

Composition for Inhalation Administration

For an aerosol container with a capacity of 20-30 ml: a mixture of 10 mg of GSAO with 0.5-0.8% by weight of a lubricating agent, such as polysorbate 85 or oleic acid, is dispersed in a propellant, such as freon, and put into an appropriate aerosol container for either intranasal or oral inhalation administration.

EXAMPLE 5(e)

Composition for Parenteral Administration

A pharmaceutical composition of the present invention for intramuscular injection could be prepared to contain 1 mL sterile buffered water, and 1 mg of GSAO.

Similarly, a pharmaceutical composition for intravenous infusion may comprise 250 ml of sterile Ringer's solution, and 5 mg of GSAO.

EXAMPLE 5(f)

Capsule Composition

A pharmaceutical composition of GSAO in the form of a capsule may be prepared by filling a standard two-piece hard gelatin capsule with 50 mg of GSAO, in powdered form, 100 mg of lactose, 35 mg of talc and 10 mg of magnesium stearate.

EXAMPLE 5(g)

Injectable Parenteral Composition

A pharmaceutical composition of this invention in a form suitable for administration by injection may be prepared by mixing 1% by weight of GSAO in 10% by volume propylene glycol and water. The solution is sterilised by filtration.

EXAMPLE 5(h)

Ointment Composition

A typical composition for delivery as an ointment includes 1.0 g of GSAO, together with white soft paraffin to 100.0 g, dispersed to produce a smooth, homogeneous product.

INDUSTRIAL APPLICABILITY

The present invention relates to substantially cell-membrane impermeable compounds having the ability to inhibit redox active proteins and to methods for their synthesis. In particular, the invention relates to substantially cell-membrane impermeable trivalent organoarsenical compounds and to methods for their synthesis. The invention also relates to pharmaceutical compositions and to methods of treatment of inflammatory disorders, autoimmune diseases, blood vessel diseases, thrombosis, viral infections, and haematological and solid tumours.

REFERENCES

Adams E, Jeter D, Cordes A W, Kolis J W. 1990. Chemistry of organometalloid complexes with potential antidotes: structure of an organoarsenic(III) dithiolate rings. Inorg Chem 29:1500-1503.

Ades E W, Candal F J, Swerlick R A, George V G, Summers S, Bosse D C, Lawley T J. 1992. HMEC-1: establishment of an immortalised human microvascular endothelial cell line. J Invest Dermatol 99:683-690.

Ausbel, F. M., Brent, R., Kingston, R. E., Moore, D. D., Seidman. J. G., Smith, J. A., Struhl, D. "Current Protocols in Molecular Biology, Supplement 29—Overview of Genetic Reporter Systems" John Wiley and Sons Inc., New York, 2000

Doak G O, Freedman L D. 1970. In: Seyferth D, ed. Organometallic compounds of Arsenic, Antimony, and Bismuth. New York, N.Y.: Wiley-Interscience.

Fleury S G, Croteau G, Sekaly R P. 1991. CD4 and CD8 recognition of class II and class I molecules of the major histocompatibility complex. Semin Immunol 3:177-185.

Folkman J. 1985. Angiogenesis and its inhibitors. in Important Advances in Oncology, eds: DeVita, V. T., Hellman, S., Rosenberg, S. 42-62 (J.B. Lippincoft Company, Philadelphia).

Folkman J. 1995. Angiogenesis in cancer, vascular, rheumatoid and other disease, Nature Med 1:27-30.

Folkman J, Haundenschild C C, Zetter B R. 1979. Long-term culture of capillary endothelial cells, Proc Natl Acad Sci USA 76:5217-5221.

Gavrieli Y, Sherman Y, Ben-Sasson S A. 1992. Identification of programmed cell death in situ via specific labeling of nuclear DNA fragmentation. J Cell Biol 119:493-501.

Gilbert H F. 1997. Protein disulfide isomerase and assisted protein folding. J Biol Chem 272:29399-29402.

Hogg P J, Stathakis P, Jimenez B M, Chesterman C N. 1997. Interaction of platelet-derived growth factor with thrombospondin 1: Dependence on the disulfide-bond arrangement in thrombospondin 1. Biochem J 326:709-716.

Hanahan D, Folkman J. 1996. Patterns and emerging mechanisms of the angiogenic switch during tumoungenesis. Cell 86:353-364.

Holmgren A. 1989. Thioredoxin and glutaredoxin systems, J Biol Chem 264:13963-13966.

Holmgren L, O'Reilly M S, Folkman J. 1995. Dormancy of micrometastases: balanced proliferation and apoptosis in the presence of angiogenesis suppression. Nature Med 1:149-153.

Hotchkiss K A, Matthias L J, Hogg P J. 1998. Exposure of the cryptic Arg-Gly-Asp sequence in thrombospondin 1 by protein disulfide isomerase. Biochim Biophys Acta 1388: 478-488.

Huppa J B, Ploegh H L. 1998. The eS-Sence of —SH in the ER. Cell 92:145-148.

Jauhiainen M, Stevenson K J, Dolphin P J. 1988. Human plasma lecithin-cholesterol acyltransferase. The vicinal nature of cysteine 31 and cysteine 184 in the catalytic site. J Biol Chem 263:6525-6533.

Jiang X-M, Fitzgerald M, Grant C M, Hogg P J. 1999. Redox control of exofacial protein thiolsidisulfides by protein disulfide isomerase. J Biol Chem 274:2416-2423.

Knoch F, Schmachtel T, Ullrich V. 1995. Crystal structure of 4-amino-1-arsenoso-benzene dihydrate, $H_2NC_6H_4As(OH)_2(H_2O)$. Z Krist 210:642.

Laemmli UK. 1970. Cleavage of structural proteins during the assembly of the head of bacteriophage T4. Nature 227: 680-685.

Littman D R. 1998. Chemokine receptors: keys to AIDS pathogenesis? Cell 93:677-680.

Metcalf D. 1977. Hemopoietic colonies: in vitro cloning of normal and leukemic cells. Recent Results Cancer Res 61:12-31.

Nakashima I, Pu M-Y, Nishizaki A, Rosila I, Ma L, Katano Y, Ohkusu K, Rahman S M J, Isobe K-I, Hamaguchi M, Saga K. 1994. Redox mechanism as alternative to ligand binding for receptor activation delivering disregulated cellular signals. J Immunol 152:1064-1071.

Nguyen M, Shing Y, Folkman J. 1994. Quantitation of angiogenesis and antiangiogenesis in the chick embryo chorioallantoic membrane. Microvascular Res 47:31-40.

Oliver M H, Harrison N K, Bishop J E, Cole P J, Laurent G J. 1989. A rapid and convenient assay for counting cells cultured in microwell plates: application for assessment of growth factors. J Cell Sci 92:513-518.

Riddles P W, Blakeley R L, Zemer B. 1983. Reassessment of Ellman's reagent. Methods Enzymol 91:49-60.

Risau W. 1997. Mechanisms of angiogenesis. Nature 386: 671-674.

Rosen A, Lundman P. Carlsson M, Bhavani K, Srinivasa B R, Kiellström G, Nilsson K, Holmgren A. 1995. A CD4+ T cell line-secreted factor, growth promoting for normal and leukemic B cells, identified as thioredoxin. Int Immunol 7:625-33.

Stathakis P, Fitzgerald M, Matthias L J, Chesterman C N, Hogg P J. 1997. Generation of angiostatin by reduction and proteolysis of plasmin: catalysis by a plasmin reductase secreted by cultured cells. J Biol Chem 272: 20641-20645.

Stocken L A, Thompson R H S. 1946. British Anti-Lewisite 2. Dithiol compounds as antidotes for arsenic. Biochem J 40:535-548.

Täger M, Kröning H. Thiel U, Ansorage S. 1997. Membrane-bound proteindisulfide isomerase (PDI) is involved in regulation of surface expression of thiols and drug sensitivity of B-CLL cells. Exp Hematol 25:601-607.

Wall R T, Marker L A, Quadracci L J, Striker G E. 1978. Factors influencing endothelial cell proliferation in vitro. J Cell Physiol 96: 203-213.

Weidner N, Semple J P, Welch W R, Folkman J. 1991. Tumour angiogenesis and metastasis: correlation in invasive breast carcinoma. N Engl J Med 324:1-8.

Weissleder R, Tung C-H, Mahmood U, Bogdanov A Jr, 1999. In vivo imaging of tumours with protease-activated near-infrared fluorescent probes. Nature Biotech 17:375-378.

The invention claimed is:

1. A method of treatment of cancer in a vertebrate in need of said treatment, wherein said method comprises administering to the vertebrate a therapeutically effective amount of a compound according to the Formula (I) or salt thereof, each alone or together with a pharmaceutically acceptable carrier, adjuvant and/or diluent:

    (I)

wherein
A is selected from the group consisting of glutathione, glucosamine, cysteinylglycine, cysteic acid, aspartic acid, glutamic acid, lysine, and arginine, and wherein the sulfur atom of each sulfur containing compound may be optionally oxidised to form a sulfoxide or sulfone;
X is selected from the group consisting of: NR—, S(O)—, —S(O)O—, —S(O)$_2$—, —S(O)$_2$O—, —C(O)—, —C(S)—, —C(O)O—, C(S)O—, —C(S)S—, —P(O)(R$_1$)—, —P(O)(R$_1$)O—, or is absent;
B is selected from $C_1$-$C_{10}$ alkylene, $C_2$-$C_{10}$ alkenylene, $C_2$-$C_{10}$ alkynylene, $C_3$-$C_{10}$ cycloalkylene, $C_5$-$C_{10}$ cycloalkenylene, $C_3$-$C_{10}$ heterocycloalkylene, $C_5$-$C_{10}$ heterocycloalkenylene, $C_6$-$C_{12}$arylene, heteroarylene or $C_2$-$C_{10}$acyl;
X' is selected from NR—, —O—, —S—, —Se—, —S—S—, S(O)—, —OS(O)—, OS(O)O—, —OS(O)$_2$, —OS(O)$_2$O—, —S(O)O—, —S(O)$_2$—, —S(O)$_2$O—, —OP(O)(R$_1$)—, —OP(O)(R$_1$)O—, —OP(O)(R$_1$)OP(O)(R$_1$)O—, —C(O)—, —C(S)—, —C(O)O—, C(S)O—, —C(S)S—, —P(O)(R$_1$)—, —P(O)(R$_1$)O—,

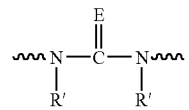

or is absent; wherein E is O, S, Se, NR or NR$_2^+$; and
B' is $C_1$-$C_{10}$ alkylene, $C_2$-$C_{10}$ alkenylene, $C_2$-$C_{10}$ alkynylene, $C_3$-$C_{10}$ cycloalkylene, $C_5$-$C_{10}$ cycloalkenylene, $C_3$-$C_{10}$ heterocycloalkylene, $C_5$-$C_{10}$ heterocycloalkenylene, $C_6$-$C_{12}$ arylene, and heteroarylene, or is absent; and wherein
each R is independently selected from hydrogen, $C_1$-$C_{10}$ alkyl, $C_2$-$C_{10}$ alkenyl, $C_2$-$C_{10}$ alkynyl, $C_3$-$C_{10}$ cycloalkyl, $C_5$-$C_{10}$ cycloalkenyl, $C_3$-$C_{10}$ heterocycloalkyl, $C_5$-$C_{10}$ heterocycloalkenyl, $C_6$-$C_{12}$ aryl, heteroaryl, OR$_2$ or $C_2$-$C_{10}$ acyl;
R' is the same as R or two R' may be taken together with the nitrogen atoms to which they are attached to form a 5 or 6-membered saturated or unsaturated heterocyclic ring;
each R$_1$ is independently selected from hydrogen, $C_1$-$C_{10}$ alkyl, $C_2$-$C_{10}$ alkenyl, $C_2$-$C_{10}$ alkynyl, $C_3$-$C_{10}$ cycloalkyl, $C_5$-$C_{10}$ cycloalkenyl, $C_3$-$C_{10}$ heterocycloalkyl, $C_5$-$C_{10}$ heterocycloalkenyl, $C_6$-$C_{12}$ aryl, heteroaryl, halo, OR$_2$ or N(R)$_2$;
each R$_2$ is independently selected from hydrogen, $C_1$-$C_{10}$ alkyl, $C_2$-$C_{10}$ alkenyl, $C_2$-$C_{10}$ alkynyl, $C_3$-$C_{10}$ cycloalkyl, $C_5$-$C_{10}$ cycloalkenyl, $C_3$-$C_{10}$ heterocycloalkyl, $C_5$-$C_{10}$ heterocycloalkenyl, $C_6$-$C_{12}$ aryl, heteroaryl or —C(O)R$_5$;
each R$_5$ is independently selected from hydrogen, $C_1$-$C_{10}$ alkyl, $C_2$-$C_{10}$ alkenyl, $C_2$-$C_{10}$ alkynyl, $C_3$-$C_{10}$ cycloalkyl, $C_5$-$C_{10}$ cycloalkenyl, $C_3$-$C_{10}$ heterocycloalkyl, $C_5$-$C_{10}$ heterocycloalkenyl, $C_6$-$C_{12}$ aryl, heteroaryl, $C_1$-$C_{10}$ alkoxy, $C_3$-$C_{10}$ alkenyloxy, $C_3$-$C_{10}$ alkynyloxy, $C_3$-$C_{10}$ cycloalkyloxy, $C_5$-$C_{10}$ cycloalkenyloxy, $C_3$-$C_{10}$ heterocycloalkyloxy, $C_5$-$C_{10}$ heterocycloalkenyloxy, $C_6$-$C_{12}$ aryloxy, heteroaryloxy, $C_1$-$C_{10}$ alkylthio, $C_3$-$C_{10}$ alkenylthio, $C_3$-$C_{10}$ alkynylthio, $C_3$-$C_{10}$ cycloalkylthio, $C_5$-$C_{10}$ cycloalkenylthio, $C_3$-$C_{10}$ heterocycloalkylthio, $C_5$-$C_{10}$ heterocycloalkenylthio, $C_6$-$C_{12}$ arylthio, heteroarylthio, OH, SH or N(R)$_2$;
wherein for each instance that B and/or B' is arylene, the substituents directly attached to the respective arylene rings (including arsenoxide) may be in a para, meta or ortho relationship, and
wherein each alkylene, alkenylene, alkynylene, cycloalkylene, cycloalkenylene, heterocycloalkylene, heterocycloalkenylene, arylene, heteroarylene and acyl may be independently substituted with hydrogen, $C_1$-$C_{10}$ alkyl, $C_2$-$C_{10}$ alkenyl, $C_2$-$C_{10}$ alkynyl, $C_3$-$C_{10}$ cycloalkyl, $C_5$-$C_{10}$ cycloalkenyl, $C_3$-$C_{10}$ heterocycloalkyl, $C_5$-$C_{10}$ heterocycloalkenyl, $C_6$-$C_{12}$ aryl, heteroaryl, halo, cyano, cyanate, isocyanate, OR$_{2a}$, SR$_6$, nitro, arsenoxide, —S(O)R$_3$, —OS(O)R$_3$, —S(O)$_2$R$_3$, —OS(O)$_2$R$_3$, —P(O)R$_4$R$_4$, —OP(O)R$_4$R$_4$, —N(R")$_2$, —NRC(O)(CH$_2$)$_m$Q, —C(O)R$_5$,

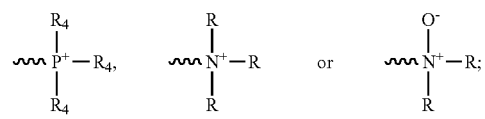

wherein R, R$_1$ and R$_5$ are as defined above; and
R$_{2a}$ is selected from hydrogen, $C_1$-$C_5$ alkyl, $C_2$-$C_5$ alkenyl, $C_2$-$C_5$ alkynyl, $C_3$-$C_{10}$ cycloalkyl, $C_5$-$C_{10}$ cycloalkenyl, $C_6$-$C_{12}$ aryl, —S(O)R$_3$, —S(O)$_2$R$_3$, —P(O)(R$_4$)$_2$, N(R)$_2$ or —C(O)R$_5$;
each R$_3$ is independently selected from hydrogen, $C_1$-$C_{10}$ alkyl, $C_2$-$C_{10}$ alkenyl, $C_2$-$C_{10}$ alkynyl, $C_3$-$C_{10}$ cycloalkyl, $C_5$-$C_{10}$ cycloalkenyl, $C_3$-$C_{10}$ heterocycloalkyl, $C_5$-$C_{10}$ heterocycloalkenyl, $C_6$-$C_{12}$ aryl, heteroaryl, $C_1$-$C_{10}$ alkoxy, $C_3$-$C_{10}$ alkenyloxy, $C_3$-$C_{10}$ alkynyloxy, $C_3$-$C_{10}$ cycloalkyloxy, $C_5$-$C_{10}$ cycloalkenyloxy, $C_3$-$C_{10}$ heterocycloalkyloxy, $C_5$-$C_{10}$ heterocycloalkenyloxy, $C_6$-$C_{12}$ aryloxy, heteroaryloxy, $C_1$-$C_{10}$ alkylthio, $C_3$-$C_{10}$ alkenylthio, $C_3$-$C_{10}$ alkynylthio, $C_3$-$C_{10}$ cycloalkylthio, $C_5$-$C_{10}$ cycloalkenylthio, $C_3$-$C_{10}$ heterocycloalkylthio, $C_5$-$C_{10}$ heterocycloalkenylthio, $C_6$-$C_{12}$ arylthio, heteroarylthio or N(R)$_2$;
each R$_4$ is independently selected from hydrogen, $C_1$-$C_{10}$ alkyl, $C_2$-$C_{10}$ alkenyl, $C_2$-$C_{10}$ alkynyl, $C_3$-$C_{10}$ cycloalkyl, $C_5$-$C_{10}$ cycloalkenyl, $C_3$-$C_{10}$ heterocycloalkyl, $C_5$-$C_{10}$ heterocycloalkenyl, $C_6$-$C_{12}$ aryl, heteroaryl, $C_1$-$C_{10}$ alkoxy, $C_3$-$C_{10}$ alkenyloxy, $C_3$-$C_{10}$ alkynyloxy, $C_3$-$C_{10}$ cycloalkyloxy, $C_5$-$C_{10}$ cycloalkenyloxy, $C_3$-$C_{10}$ heterocycloalkyloxy, $C_5$-$C_{10}$ heterocycloalkenyloxy, $C_6$-$C_{12}$ aryloxy, heteroaryloxy, $C_1$-$C_{10}$ alkylthio, $C_3$-$C_{10}$ alkenylthio, $C_3$-$C_{10}$ alkynylthio, $C_3$-$C_{10}$ cycloalkylthio, $C_5$-$C_{10}$ cycloalkenylthio, $C_5$-$C_{10}$ heterocycloalkylthio, $C_5$-$C_{10}$ heterocycloalkenylthio, $C_6$-$C_{12}$ arylthio, heteroarylthio, halo or N(R)$_2$;
R$_6$ is selected from $C_1$-$C_{10}$ alkyl, $C_2$-$C_{10}$ alkenyl, $C_2$-$C_{10}$ alkynyl, $C_3$-$C_{10}$ cycloalkyl, $C_5$-$C_{10}$ cycloalkenyl, $C_3$-$C_{10}$ heterocycloalkyl, $C_5$-$C_{10}$ heterocycloalkenyl, $C_6$-$C_{12}$ aryl, heteroaryl, $C_1$-$C_{10}$ alkylthio, $C_3$-$C_{10}$ alkenylthio, $C_3$-$C_{10}$ alkynylthio, $C_3$-$C_{10}$ cycloalkylthio, $C_5$-$C_{10}$ cycloalkenylthio, $C_3$-$C_{10}$ heterocycloalkylthio, $C_5$-$C_{10}$ heterocycloalkenylthio, $C_6$-$C_{12}$ arylthio, heteroarylthio, —S(O)R$_3$, —S(O)$_2$R$_3$ or —C(O)R$_5$,
R" is the same as R or two R" taken together with the N atom to which they are attached may form a saturated, unsaturated or aromatic heterocyclic ring system;

Q is selected from halogen and —OS(O)$_2$Q$_1$; wherein Q$_1$ is selected from C$_1$-C$_4$ alkyl, C$_1$-C$_4$ perfluoroalkyl, phenyl, p-methylphenyl;

M is an integer selected from 1 to 5,

Y comprises at least one arsenoxide group;

p is an integer from 1 to 10; and wherein the sum total of carbon atoms in A and (XBX')$_n$B' together, is greater than 6; and wherein the cancer is a solid tumor.

2. The method according to claim 1, wherein

X is selected from the group consisting of NR—, —C(O)—, —C(S)—, —C(O)O—, —C(S)O—, —C(S)S—, or is absent;

B is selected from C$_1$-C$_5$ alkylene, C$_2$-C$_5$ alkenylene, C$_2$-C$_5$ alkynylene, C$_3$-C$_{10}$ cycloalkylene, C$_5$-C$_{10}$ cycloalkenylene, C$_6$-C$_{12}$ arylene or C$_2$-C$_5$ acyl;

X' is selected from —O—, —S—, —NR—, —S—S—, —S(O)—, —S(O)$_2$—, —P(O)(R$_1$)—, —OP(O)(R$_1$)—, OP(O)(R$_1$)O—, —OP(O)(R$_1$)OP(O)(R$_1$)O—, —C(O)—, —C(S)—, —C(O)O—, —C(S)O—, —C(S)S—, —Se—,

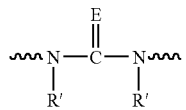

or is absent; wherein E is O, S or N(R)$_2^+$;

n is 0, 1 or 2; and

B' is C$_1$-C$_5$ alkylene, C$_2$-C$_5$ alkenylene, C$_2$-C$_5$ alkynylene, C$_3$-C$_{10}$ cycloalkylene, C$_5$-C$_{10}$ cycloalkenylene, C$_6$-C$_{12}$ arylene or is absent; and wherein each R is independently selected from hydrogen, C$_1$-C$_5$ alkyl, C$_2$-C$_5$ alkenyl, C$_2$-C$_5$ alkynyl, C$_3$-C$_{10}$ cycloalkyl, C$_5$-C$_{10}$ cycloalkenyl, C$_6$-C$_{12}$ aryl, OR$_2$ or C$_2$-C$_{10}$ acyl;

R' is the same as R;

each R$_1$ is independently selected from hydrogen, C$_1$-C$_5$ alkyl, C$_2$-C$_5$ alkenyl, C$_2$-C$_5$ alkynyl, C$_3$-C$_{10}$ cycloalkyl, C$_5$-C$_{10}$ cycloalkenyl, C$_6$-C$_{12}$ aryl, halo, OR$_2$ or N(R)$_2$;

each R$_2$ is independently selected from hydrogen, C$_1$-C$_5$ alkyl, C$_2$-C$_5$ alkenyl, C$_2$-C$_5$ alkynyl, C$_3$-C$_{10}$ cycloalkyl, C$_5$-C$_{10}$ cycloalkenyl, C$_6$-C$_{12}$ aryl or —C(O)R$_5$;

each R$_5$ is independently selected from hydrogen, C$_1$-C$_5$ alkyl, C$_2$-C$_5$ alkenyl, C$_2$-C$_5$ alkynyl, C$_3$-C$_{10}$ cycloalkyl, C$_5$-C$_{10}$ cycloalkenyl, C$_6$-C$_{12}$ aryl, C$_1$-C$_5$ alkoxy, C$_3$-C$_5$ alkenyloxy, C$_3$-C$_5$ alkynyloxy, C$_3$-C$_{10}$ cycloalkyloxy, C$_5$-C$_{10}$ cycloalkenyloxy, C$_6$-C$_{12}$ aryloxy, C$_1$-C$_5$ alkylthio, C$_3$-C$_5$ alkenylthio, C$_3$-C$_5$ alkynylthio, C$_3$-C$_{10}$ cycloalkylthio, C$_5$-C$_{10}$ cycloalkenylthio, C$_6$-C$_{12}$ arylthio, OH, SH or N(R)$_2$;

wherein each instance of arylene may have substituents A and X or X and Y in a para, meta or ortho relationship, and wherein each alkylene, alkenylene, alkynylene, cycloalkylene, cycloalkenylene, arylene, and acyl may be independently substituted with hydrogen, C$_1$-C$_5$ alkyl, C$_2$-C$_5$ alkenyl, C$_2$-C$_5$ alkynyl, C$_3$-C$_{10}$ cycloalkyl, C$_5$-C$_{10}$ cycloalkenyl, C$_6$-C$_{12}$ aryl, halo, cyanate, isocyanate, OR$_{2a}$, SR$_6$, nitro, arsenoxide, —S(O)R$_3$, —OS(O)R$_3$, —S(O)$_2$R$_3$, —OS(O)$_2$R$_3$, —P(O)R$_4$R$_4$, —OP(O)R$_4$R$_4$, —N(R'')$_2$, NRC(O)(CH$_2$)$_m$Q, —C(O)R$_5$,

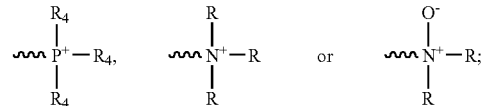

wherein R, R$_1$ and R$_5$ are as defined above; and

R$_{2a}$ selected from hydrogen, C$_1$-C$_5$ alkyl, C$_2$-C$_5$ alkenyl, C$_2$-C$_5$ alkynyl, C$_3$-C$_{10}$ cycloalkyl, C$_5$-C$_{10}$ cycloalkenyl, C$_6$-C$_{12}$ aryl, —S(O)R$_3$, —S(O)$_2$R$_3$, —P(O)(R$_4$)$_2$, N(R)$_2$ or —C(O)R$_5$;

each R$_3$ is independently selected from hydrogen, C$_1$-C$_5$ alkyl, C$_2$-C$_5$ alkenyl, C$_2$-C$_5$ alkynyl, C$_3$-C$_{10}$ cycloalkyl, C$_5$-C$_{10}$ cycloalkenyl, C$_6$-C$_{12}$ aryl, C$_1$-C$_5$ alkoxy, C$_3$-C$_5$ alkenyloxy, C$_3$-C$_5$ alkynyloxy, C$_3$-C$_{10}$ cycloalkyloxy, C$_5$-C$_{10}$ cycloalkenyloxy, C$_6$-C$_{12}$ aryloxy, C$_1$-C$_5$ alkylthio, C$_3$-C$_5$ alkenylthio, C$_3$-C$_5$ alkynylthio, C$_3$-C$_{10}$ cycloalkylthio, C$_5$-C$_{10}$ cycloalkenylthio, C$_6$-C$_{12}$ arylthio or N(R)$_2$;

each R$_4$ is independently selected from hydrogen, C$_1$-C$_5$ alkyl, C$_2$-C$_5$ alkenyl, C$_2$-C$_5$ alkynyl, C$_3$-C$_{10}$ cycloalkyl, C$_5$-C$_{10}$ cycloalkenyl, C$_6$-C$_{12}$ aryl, C$_1$-C$_5$ alkoxy, C$_3$-C$_5$ alkenyloxy, C$_3$-C$_5$ alkynyloxy, C$_3$-C$_{10}$ cycloalkyloxy, C$_5$-C$_{10}$ cycloalkenyloxy, C$_6$-C$_{12}$ aryloxy, C$_1$-C$_5$ alkylthio, C$_3$-C$_5$ alkenylthio, C$_3$-C$_5$ alkynylthio, C$_3$-C$_5$ cycloalkylthio, C$_5$-C$_5$ cycloalkenylthio, C$_6$-C$_{12}$ arylthio, halo or N(R)$_2$;

R$_6$ is independently selected from C$_1$-C$_5$ alkyl, C$_2$-C$_5$ alkenyl, C$_2$-C$_5$ alkynyl, C$_3$-C$_{10}$ cycloalkyl, C$_5$-C$_{10}$ cycloalkenyl, C$_6$-C$_{12}$ aryl, C$_1$-C$_5$ alkylthio, C$_3$-C$_5$ alkenylthio, C$_3$-C$_5$ alkynylthio, C$_3$-C$_{10}$ cycloalkylthio, C$_5$-C$_{10}$ cycloalkenylthio, C$_6$-C$_{12}$ arylthio, —S(O)R$_3$, —S(O)$_2$R$_3$ or —C(O)R$_5$;

R'' is the same as R;

Q is selected from halogen and —OS(O)$_2$Q$_1$; wherein Q$_1$ is selected from C$_1$-C$_4$ alkyl, C$_1$-C$_4$ perfluoroalkyl, phenyl, p-methylphenyl; and m is 1 to 5.

3. The method according to claim 1, wherein

X is absent;

B is selected from C$_1$-C$_5$ alkylene, C$_6$-C$_{12}$ arylene or C$_2$-C$_5$ acyl;

X' is selected from —O—, —S—, —NR—, —S—S—, —S(O)—, —S(O)$_2$—, —P(O)(R$_1$)—, —C(O)—, —C(S)—, —C(O)O—, —C(S)O—, —Se—,

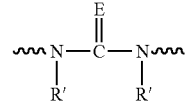

or absent; wherein E is O, S or N(R)$_2^+$;

n is 0, 1 or 2; and

B' is C$_1$-C$_5$ alkylene, C$_6$-C$_{12}$ arylene or is absent; and wherein each R is independently selected from hydrogen, C$_1$-C$_5$ alkyl, C$_3$-C$_{10}$ cycloalkyl, C$_6$-C$_{12}$ aryl, OR$_2$ or C$_2$-C$_5$ acyl;

R' is the same as R;

each R$_1$ is independently selected from hydrogen, C$_1$-C$_5$ alkyl, C$_3$-C$_{10}$ cycloalkyl, C$_6$-C$_{12}$ aryl, halo, OR$_2$ or N(R)$_2$;

each $R_2$ is independently selected from hydrogen, $C_1$-$C_5$ alkyl, $C_3$-$C_{10}$ cycloalkyl, $C_6$-$C_{12}$ aryl or —C(O)$R_5$;

each $R_5$ is independently selected from hydrogen, $C_1$-$C_5$ alkyl, $C_2$-$C_5$ alkenyl, $C_3$-$C_{10}$ cycloalkyl, $C_5$-$C_{10}$ cycloalkenyl, $C_6$-$C_{12}$ aryl, $C_1$-$C_5$ alkoxy, $C_3$-$C_5$ alkenyloxy, $C_3$-$C_{10}$ cycloalkyloxy, $C_5$-$C_{10}$ cycloalkenyloxy, $C_6$-$C_{12}$ aryloxy, $C_1$-$C_5$ alkylthio, $C_3$-$C_5$ alkenylthio, $C_3$-$C_{10}$ cycloalkylthio, $C_5$-$C_{10}$ cycloalkenylthio, $C_6$-$C_{12}$ arylthio, OH, SH or N(R)$_2$;

wherein for each instance that B and/or B' is arylene, the substituents directly attached to the respective arylene rings (including arsenoxide), may be in a para, meta or ortho relationship, and wherein each alkylene, alkenylene, alkynylene, cycloalkylene, cycloalkenylene, arylene, and acyl may be independently substituted with hydrogen, $C_1$-$C_5$ alkyl, $C_2$-$C_5$ alkenyl, $C_2$-$C_5$ alkynyl, $C_3$-$C_{10}$ cycloalkyl, $C_5$-$C_{10}$ cycloalkenyl, $C_6$-$C_{12}$ aryl, halo, cyano, cyanate, isocyanate, OR$_{2a}$, SR$_6$, nitro, arsenoxide, —S(O)R$_3$, —OS(O)R$_3$, —S(O)$_2$R$_3$, —OS(O)$_2$R$_3$, —P(O)R$_4$R$_4$, —OP(O)R$_4$R$_4$, —N(R")$_2$, —NRC(O)(CH$_2$)$_m$Q, —C(O)R$_5$,

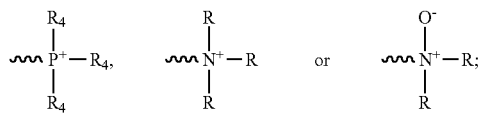

wherein R, $R_1$ and $R_5$ are as defined above; and $R_{2a}$ is selected from hydrogen, $C_1$-$C_5$ alkyl, $C_3$-$C_{10}$ cycloalkyl, $C_6$-$C_{12}$ aryl, —S(O)R$_3$, —S(O)$_2$R$_3$, —P(O)(R$_4$)$_2$ and —C(O)R$_5$;

each $R_3$ is independently selected from hydrogen, $C_1$-$C_5$ alkyl, $C_3$-$C_{10}$ cycloalkyl, $C_6$-$C_{12}$ aryl, $C_1$-$C_5$ alkoxy, $C_3$-$C_{10}$ cycloalkyloxy, $C_6$-$C_{12}$ aryloxy, $C_1$-$C_5$ alkylthio, $C_3$-$C_{10}$ cycloalkylthio, $C_6$-$C_{12}$ arylthio or N(R)$_2$;

each $R_4$ is independently selected from hydrogen, $C_1$-$C_5$ alkyl, $C_3$-$C_{10}$ cycloalkyl, $C_6$-$C_{12}$ aryl, $C_1$-$C_5$ alkoxy, $C_3$-$C_{10}$ cycloalkyloxy, $C_6$-$C_{12}$ aryloxy, halo or N(R)$_2$;

$R_6$ is selected from $C_1$-$C_5$ alkyl, $C_3$-$C_{10}$ cycloalkyl, $C_6$-$C_{12}$ aryl, $C_1$-$C_5$ alkylthio, $C_3$-$C_{10}$ cycloalkylthio, $C_6$-$C_{12}$ arylthio, —S(O)R$_3$, —S(O)$_2$R$_3$ or —C(O)R$_5$;

R" is the same as R;

Q is selected from halogen and —OS(O)$_2$Q$_1$; wherein Q$_1$ is selected from $C_1$-$C_4$ alkyl, $C_1$-$C_4$ perfluoroalkyl, phenyl, p-methylphenyl; and m is 1 to 5.

4. The method according to claim 1, wherein

X is absent;

B is selected from $C_1$-$C_5$ alkylene, $C_6$-$C_{12}$ arylene or $C_2$-$C_5$ acyl;

X' is selected from —O—, —S—, —NR—, —C(O)—, —C(O)O—, or is absent;

n is 1; and

B' is $C_1$-$C_5$ alkylene, $C_6$-$C_{12}$ arylene or is absent; and

R is selected from hydrogen, $C_1$-$C_5$ alkyl, $C_6$-$C_{12}$ aryl or $C_2$-$C_5$ acyl;

wherein for each instance that B and/or B' is arylene, the substituents directly attached to the respective arylene rings (including arsenoxide), may be in a para, meta or ortho relationship, and wherein each alkylene, arylene, and acyl may be independently substituted with hydrogen, $C_1$-$C_5$ alkyl, $C_2$-$C_5$ alkenyl, $C_2$-$C_5$ alkynyl, $C_3$-$C_{10}$ cycloalkyl, $C_5$-$C_{10}$ cycloalkenyl, $C_6$-$C_{12}$ aryl, halo, cyano, cyanate, isocyanate, OR$_{2a}$, SR$_6$, nitro, arsenoxide, —S(O)R$_3$, —S(O)$_2$R$_3$, —P(O)R$_4$R$_4$, —N(R")$_2$, —NRC(O)(CH$_2$)$_m$Q, —C(O)R$_5$,

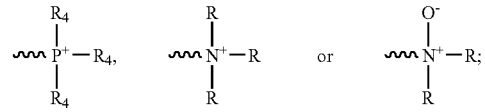

wherein each R is independently selected from hydrogen, $C_1$-$C_5$ alkyl, $C_6$-$C_{12}$ aryl or $C_2$-$C_5$ acyl;

$R_{2a}$ is selected from hydrogen, $C_1$-$C_5$ alkyl, $C_6$-$C_{12}$ aryl, —S(O)R$_3$, —S(O)$_2$R$_3$, —P(O)(R$_4$)$_2$ or —C(O)R$_5$;

each $R_3$ is independently selected from hydrogen, $C_1$-$C_5$ alkyl, $C_6$-$C_{12}$ aryl, $C_1$-$C_5$ alkoxy, $C_6$-$C_{12}$ aryloxy, $C_1$-$C_5$ alkylthio, or $C_6$-$C_{12}$ arylthio;

each $R_4$ is independently selected from hydrogen, $C_1$-$C_5$ alkyl, $C_6$-$C_{12}$ aryl, $C_1$-$C_5$ alkoxy, $C_6$-$C_{12}$ aryloxy, $C_1$-$C_5$ alkylthio, $C_6$-$C_{12}$ arylthio, halo or N(R)$_2$;

each $R_5$ is independently selected from hydrogen, $C_1$-$C_5$ alkyl, $C_6$-$C_{12}$ aryl, $C_1$-$C_5$ alkoxy, $C_6$-$C_{12}$ aryloxy, $C_1$-$C_5$ alkylthio, $C_6$-$C_{12}$ arylthio, OH, SH or N(R)$_2$;

$R_6$ is selected from $C_1$-$C_5$ alkyl, $C_6$-$C_{12}$ aryl, $C_1$-$C_5$ alkylthio, $C_6$-$C_{12}$ arylthio, —S(O)R$_3$, R" is the same as R above;

Q is selected from halogen and —OS(O)$_2$Q$_1$; wherein Q$_1$ is selected from $C_1$-$C_4$ alkyl, $C_1$-$C_4$ perfluoroalkyl, phenyl, p-methylphenyl; and m is 1 to 5.

5. The method according to claim 1, wherein

X is absent;

B is $C_2$-$C_5$ acyl;

X' is NR;

n is 1;

B' is phenylene; and

R is H;

wherein for each instance that B and/or B' is arylene, the substituents directly attached to the respective arylene rings (including arsenoxide), may be in a para-, meta- or ortho-relationship.

6. The method according to claim 1 wherein the compound of structural formula I is of structural Formula III:

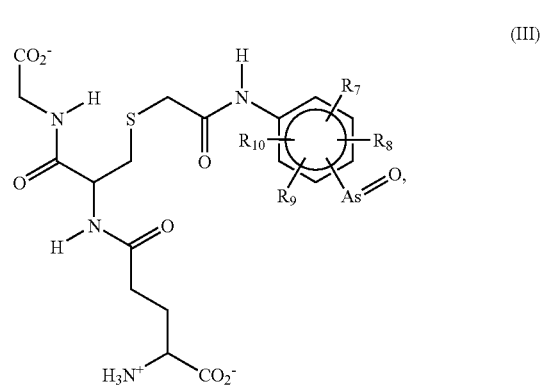

and wherein $R_7$ to $R_{10}$ are independently selected from the group consisting of: hydrogen, $C_1$-$C_5$ alkyl, $C_6$-$C_{12}$ aryl, halogen, hydroxy, amino, nitro, carboxy, $C_1$-$C_5$ alkoxy, —OS(O)$_2$ R$_3$ or —NHC(O)CH$_2$Q wherein Q is halogen, —OS(O)$_2$CH$_3$, —OS(O)$_2$C$_6$H$_5$ or —OS(O)$_2$-p tolyl.

7. The method according to claim 6, wherein $R_7$ to $R_{10}$ are independently selected from the group consisting of: hydrogen, halogen, hydroxy, amino, nitro, carboxy, $C_1$-$C_5$ alkoxy, methyl, ethyl, iso-propyl, tert-butyl, phenyl and —NHC(O)CH$_2$Q wherein Q is halogen, —OS(O)$_2$CH$_3$, —OS(O)$_2$C$_6$H$_5$ or —OS(O)$_2$-p tolyl.

8. The method according to claim 6, wherein the arsenoxide (—As=O) group is at the 4-position of the phenylene ring.

9. The method according to claim 1 wherein the compound is 4-(N-(S -glutathionylacetyl)amino)phenylarsenoxide (GSAO) and is represented by Formula V:

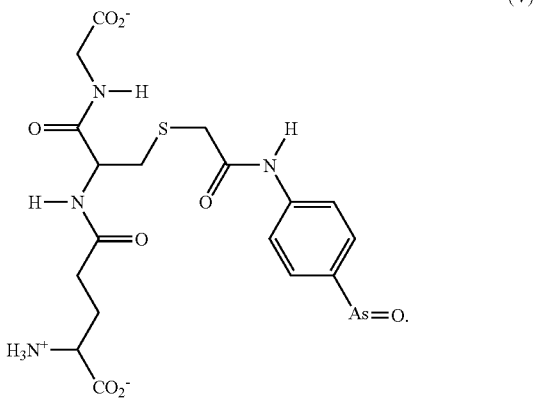

(V)

10. The method according to claim 1 wherein the compound is represented by Formula VI:

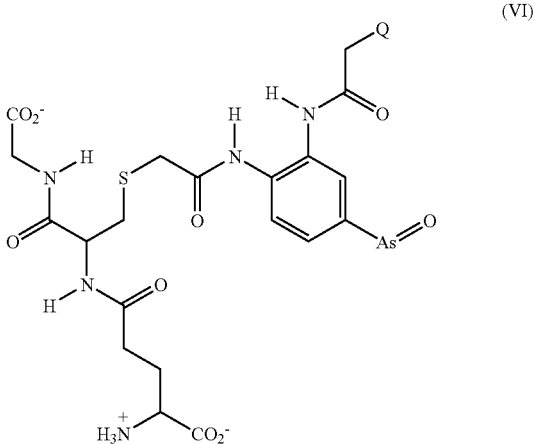

(VI)

wherein Q is any halogen.

11. The method according to claim 1 wherein the compound is represented by Formula VII:

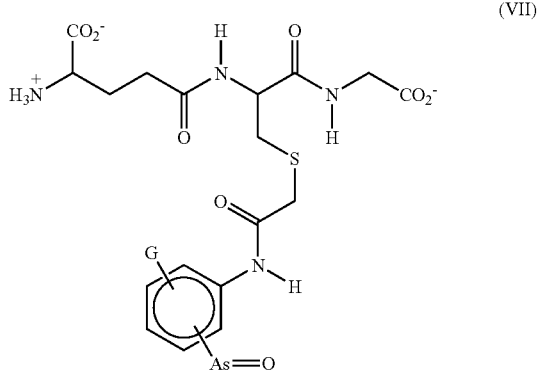

(VII)

wherein G is selected from the group consisting of: hydrogen, halogen, hydroxy, amino, nitro, carboxy, $C_1$-$C_5$ alkoxy, $C_1$-$C_5$ alkyl and $C_6$-$C_{12}$ aryl and —NHC(O)CH$_2$Q wherein Q is halogen, —OS(O)$_2$CH$_3$, —OS(O)$_2$C$_6$H$_5$ or —OS(O)$_2$-p tolyl.

12. The method according to claim 11, wherein G is selected from the group consisting of: hydrogen, halogen, hydroxy, amino, nitro, carboxy, $C_1$-$C_5$ alkoxy, methyl, ethyl, iso-propyl, tert-butyl, phenyl, and —NHC(O)CH$_2$Q wherein Q is halogen, —OS(O)$_2$CH$_3$, —OS(O)$_2$C$_6$H$_5$ or —OS(O)$_2$-p tolyl.

13. The method according to claim 11, wherein G is selected from the group consisting of hydroxy, fluorine, amino, and nitro.

14. The method according to claim 11 wherein the activity of the arsenic atom may be modified by the group G, when G and the arsenic atom are in an ortho- or para-relationship to one another.

15. The method according to claim 1, wherein the arsenoxide group (—As=O) is replaced by an arsenoxide equivalent.

16. The method according to claim 15, wherein said arsenoxide equivalent is in the form of -D(Z$_1$)(Z$_2$), wherein D is As Sn, Sb, Ge, and Z$_1$ and Z$_2$ are labile groups, and wherein Z$_1$ and Z$_2$, may be identical or different, and may either be connected or independent from each other (bound only to the arsenic atom).

17. The method according to claim 16, wherein Z$_1$ and Z$_2$ are selected from OH, $C_1$-$C_{10}$ alkoxy, $C_6$-$C_{10}$ aryloxy, $C_1$-$C_{10}$ alkylthio, $C_6$-$C_{10}$ arylthio, $C_1$-$C_{10}$ alkylseleno, $C_6$-$C_{10}$ arylseleno, OH, OR, SR, SeR, F, Cl, Br and I, and wherein R is an alkyl or an aryl group.

18. The method according to claim 1 wherein the compound is linked to a detector group.

19. The method of claim 18 wherein said detector group is selected from the group consisting of fluorophore, biotin, radionucleotide, biotin, fluorescein, and a group comprising a transition element.

20. The method according to claim 18 wherein the detector group is biotin.

21. The method according to claim 19 wherein the radionucleotide is selected from the group consisting of $^3$H, $^{14}$C, $^{32}$P, $^{33}$P, $^{35}$S, $^{125}$I, $^{131}$I, $^{123}$I, $^{111}$In, [105]Rh, [153]Sm, [67]Cu, $^{67}$Ga, [166]Ho, $^{177}$Lu, [186]Re, [188]Re, and [99m]Tc.

22. The method of claim 1 wherein the cancer is pancreatic or lung cancer.

* * * * *